United States Patent
Miller et al.

(10) Patent No.: US 10,724,023 B2
(45) Date of Patent: *Jul. 28, 2020

(54) MICROORGANISMS EXPRESSING MODIFIED GLUCOAMYLASE ENZYMES

(71) Applicant: CARGILL, INCORPORATED, Wayzata, MN (US)

(72) Inventors: Christopher K. Miller, Andover, MN (US); Ana Negrete-Raymond, Chanhassen, MN (US); Jonathan Dwight Veldhouse, Plymouth, MN (US); Amit Vas, Minneapolis, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/511,319

(22) Filed: Jul. 15, 2019

(65) Prior Publication Data

US 2020/0048623 A1    Feb. 13, 2020

Related U.S. Application Data

(63) Continuation of application No. 15/548,812, filed as application No. PCT/US2016/016822 on Feb. 5, 2016, now Pat. No. 10,364,421.

(60) Provisional application No. 62/112,807, filed on Feb. 6, 2015.

(51) Int. Cl.
| | |
|---|---|
| C12N 9/34 | (2006.01) |
| C07K 14/395 | (2006.01) |
| C12P 19/14 | (2006.01) |
| C12N 9/16 | (2006.01) |

(52) U.S. Cl.
CPC .......... *C12N 9/2428* (2013.01); *C07K 14/395* (2013.01); *C12N 9/16* (2013.01); *C12P 19/14* (2013.01); *C12Y 301/03002* (2013.01); *C07K 2319/02* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 4,546,082 A | 10/1985 | Kurjan et al. | |
| 4,870,008 A | 9/1989 | Brake | |
| 5,024,941 A | 6/1991 | Maine et al. | |
| 5,422,267 A | 6/1995 | Yocum et al. | |
| 5,521,086 A | 5/1996 | Scott et al. | |
| 5,587,290 A | 12/1996 | Klionsky et al. | |
| 6,214,577 B1 | 4/2001 | Yocum | |
| 7,785,872 B2 | 8/2010 | Chang et al. | |
| 8,394,622 B2 | 3/2013 | Haefele et al. | |
| 8,664,475 B2 | 3/2014 | Puzio et al. | |
| 8,733,149 B2 | 5/2014 | Yu et al. | |
| 8,733,321 B2 | 5/2014 | Cohn et al. | |
| 8,735,544 B1 | 5/2014 | Hammond et al. | |
| 10,344,288 B2 * | 7/2019 | Miller | C12N 15/81 |
| 10,364,421 B2 * | 7/2019 | Miller | C07K 14/395 |
| 2007/0065905 A1 | 3/2007 | Branduardi et al. | |
| 2007/0117186 A1 | 5/2007 | Sahara et al. | |
| 2007/0166788 A1 | 7/2007 | Jin et al. | |
| 2010/0317078 A1 | 12/2010 | Villa-Garcia et al. | |
| 2011/0033907 A1 | 2/2011 | Forrester et al. | |
| 2011/0229968 A1 | 9/2011 | Sohn et al. | |
| 2012/0064591 A1 | 3/2012 | Gasch et al. | |
| 2013/0137181 A1 | 5/2013 | Choi et al. | |
| 2013/0149760 A1 | 6/2013 | Forrester et al. | |
| 2013/0323822 A1 | 12/2013 | Brevnova et al. | |

FOREIGN PATENT DOCUMENTS

| | | |
|---|---|---|
| EP | 123544 A2 | 10/1984 |
| EP | 228254 A2 | 7/1987 |
| EP | 2734490 A1 | 5/2014 |
| EP | 2735301 A1 | 5/2014 |
| WO | 03105889 A1 | 12/2003 |
| WO | 2004/042036 A2 | 5/2004 |
| WO | 2009037279 A1 | 3/2009 |
| WO | 2011153516 A2 | 12/2011 |
| WO | 2013011208 A1 | 1/2013 |
| WO | 2013092840 A1 | 6/2013 |
| WO | 2014029808 A1 | 2/2014 |
| WO | 2014078920 A1 | 5/2014 |
| WO | 2014081803 A1 | 5/2014 |
| WO | 2015023989 A1 | 2/2015 |
| WO | 2016127083 A1 | 8/2016 |
| WO | 2016160584 A1 | 10/2016 |

OTHER PUBLICATIONS

Accession E9P9V2. Apr. 5, 2011 (Year: 2011).
Accession Q8TFE5. Jun. 1, 2002 (Year: 2002).
Accession U3N160. Dec. 11, 2013 (Year: 2013).
Brake, Anthony J., et al., "a-Factor-directed synthesis and secretion of mature foreign proteins in *Saccharomyces cerevisiae*", Prov. Natl. Acad. Sci., vol. 81, pp. 4642-4646, Aug. 1984 Biochemistry.
Chica, Roberto A., et al., "Semi-rational approaches to engineering enzyme activity: combining the benefits of directed evolution and rational design", Curr Opin Biotechnol. 16(4), Aug. 2005, 378-84.
Das R C , et al., "Chapter 10: Host cell control of heterologous protein production in *Saccharomycescerevisiae*", Marcel Dekker, Inc., New York / Basel, XP008179956, 1990, 311-342.

(Continued)

*Primary Examiner* — Christian L Fronda

(57) ABSTRACT

The invention is directed to non-natural yeast able to secrete significant amounts of glucoamylase into a fermentation media. The glucoamylase can promote degradation of starch material generating glucose for fermentation to a desired bioproduct, such as ethanol. The glucoamylase can be provided in the form of a glucoamylase fusion protein having a *S. cerevisiae* mating factor alpha 2 (Sc MFα2) or repressible acid phosphatase (Sc PHO5) secretion signal.

9 Claims, 1 Drawing Sheet
Specification includes a Sequence Listing.

(56) References Cited

OTHER PUBLICATIONS

Eva Hostinová, et al., "Molecular cloning and 3D structure prediction of the first raw-starch-degrading glucoamylase without a separate starch-binding domain", XP055266201, Archives of Biochemistry and Biophysics, Mar. 1, 2003 Academic Press, US—ISSN 0003-9861, vol. 411, Issue 2, Mar. 15, 2003, 189-195.

Eva Hostinová, et al., "Yeast glucoamylases: molecular-genetic and structural characterization", Biologia, SAP—Slovak Academic Press, Bratislava, SK, vol. 65 No. 4, Aug. 1, 2010, 559-568.

Flessel, Monica C., et al., "The MFa1 Gene of *Saccharomyces cerevisiae*: Genetic Mapping and Mutational Analysis of Promoter Elements", Genetics 121: 223-236 (Feb. 1989).

I. Ballesteros, , et al., "Optimization of the simultaneous saccharification and fermentation process using thermotolerant yeasts", Applied Biochemistry and Biotechnology, Spring 1993, vol. 39-40, Issue 1,, 1993, 201-211.

Lau, W.T. Walter, et al., "A Genetic Study of Signaling Processes for Repression of PH05 Transcription in *Saccharomyces cerevisiae*", Genetics Society of America 150: 1349-1359 (Dec. 1998).

Li, Jincai , et al. "Impediments to Secretion of Green Fluorescent Protein and Its Fusion from *Saccharomyces cerevisiae*", Biotechnol. Prog. 2002, 18, 831-838.

Liu, Zengran , et al., "Integrative Expression of Glucoamylase Gene in a Brewer's Yeast *Saccharomyces pastorianus* Strain", Food Technol. Biotechnol. 46 (1) 32-37 (2008.

Luo Jinxian , et al., "Expression and secretion of alpha-amylase and glucoamylase in *Saccharomyces cerevisiae*", Chinese Journal of Biotechnology, Allerton Press, vol. 10, No. 4, 1994, 241-248.

Nakamura , et al., "Alcohol fermentation of starch by a genetic recombinant yeast having glucoamylase activity", Biotechnology and Bioengineering, Wiley etc—ISSN 0006-3592, DOI: http://dx.doi.org/10.1002/(SICI)1097-0290(19970105)53:1<21::AID-BIT4>3.0.CO;2-0, vol. 53, Jan. 1, 1997, 21-25.

Punt P J , et al., "Intracellular and extracellular production of proteins in Aspergillus under the control of expression signals of the highly expressed Aspergillus nidulans gpdA gene", Journal of Biotechnology, Elsevier Science Publishers, Amsterdam, NL—ISSN 0168-1656, vol. 17, Nr:1, Jan. 1, 1991, 19-33.

Shi-Hwei Liu , et al., "Improved secretory production of glucoamylase in Pichia pastoris by combination of genetic manipulations", Biochemical and Biophysical Research Communications, Elsevier, 2005, 817-824.

Sidhu, Rajinder Singh, et al., "Selection of secretory protein-enoding genes by fusion with PH05 in *Saccharomyces cerevisiae*", Gene, 107 (1991) 111-118.

Singh, Raushan Kumar, et al., "Protein Engineering Approaches in the Post-Genomic Era", Curr Protein Pept Sci. 18, 2017, 1-11.

Tang Guomin , et al., "Integration of glucoamylase gene from Aspergillus niger into *Saccharomyces cerevisiae* genome and its stable expression", Chinese Journal of Biotechnology, Allerton Press, vol. 11 (4), 1995, 237-241.

Tetsuya Itoh , et al., "Nucleotide sequence of the glucoamylase gene GLU1 in the yeast *Saccharomycopsis fibuligera*", Journal of Bacteriology, Sep. 1987 vol. 169 No. 9, Sep. 1, 1987, 4171-4176.

\* cited by examiner

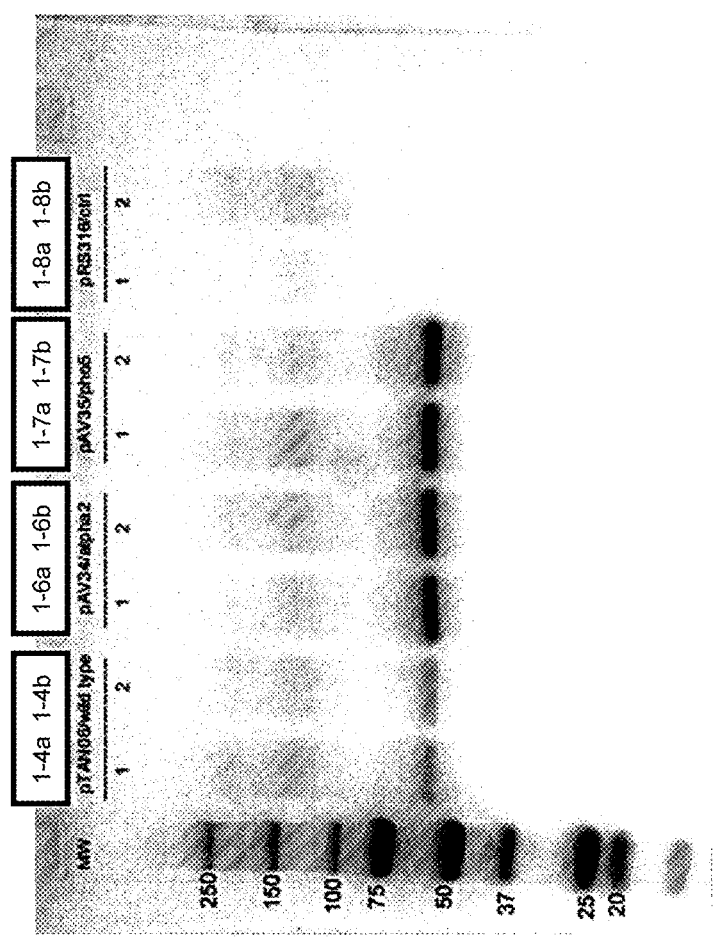

SEQUENCE LISTING

```
<160> NUMBER OF SEQ ID NOS: 15

<210> SEQ ID NO 1
<211> LENGTH: 3182
<212> TYPE: DNA
<213> ORGANISM: Artificial Sequence
<220> FEATURE:
<223> OTHER INFORMATION: pAV18 transformation fragment

<400> SEQUENCE: 1
cctactgcgc caattgatga caatacagac gatgataaca aaccgaagtt atctgatgta      60
gaaaaggatt aaagatgcta agagatagtg atgatatttc ataaataatg taattctata     120
tatgttaatt acctttttg cgaggcatat ttatggtgaa ggataagttt tgaccatcaa      180
agaaggttaa tgtggctgtg gtttcagggt ccataaagct tttcaattca tcttttttt     240 ttttgttctt tttttgatt ccggtttctt tgaaattttt ttgattcggt aatctccgag      300
cagaaggaag aacgaaggaa ggagcacaga cttagattgg tatatatacg catatgtggt     360
gttgaagaaa catgaaattg cccagtattc ttaacccaac tgcacagaac aaaaacctgc     420
aggaaacgaa gataaagcgg ccgcataact tcgtataatg tatgctatac gaagttatct     480
gccagtatac agctagcctt gaaagtgatg gaaaacattg tcatcggcac ataaataaaa     540
aaattatgaa tcacgtgatc aacagcaaat tatgtactcg tatatatgca agcgcattcc     600
ttatattgac actctttcat tgggcatgag gctgtgtaaa cataagctgt aacggtctca     660
cggaacactg tgtagttgca ttactgtcag gcagttatgt tgcttaatat aaaggcaaag     720
gcatggcaga atcactttaa aacgtggccc cacccgctgc accctgtgca tttgtacgt     780 tactgcgaaa tgactcaacg atgaaatgaa aaaattttgc ttgaaatttt gaaaaaaga     840 tgtgcgggac gcattgttag ctcattgaat acatcgtgat cgaatccaat caatgtttaa     900
tttcatatta atacagaaac tttttctcat actttcttct tcttttcatt ggtatattat     960
ctatatatcg tgttaattcc tctttcgtca tttttagcat cgttataaga gtaattaaga    1020
ataactagaa gagtctctct ttatattcgt ttattttata tatttaaccg ctaaatttag    1080
taaacaaaag aatctatcag aaatgagtga atctccaatg ttcgctgcca acggcatgcc    1140
aaaggtaaat caaggtgctg aagaagatgt cagaatttta ggttacgacc cattagcttc    1200
tccagctctc cttcaagtgc aaatcccagc cacaccaact tcttggaaa ctgccaagag    1260 aggtagaaga gaagctatag atattattac cggtaaagac gacagagttc ttgtcattgt    1320
cggtccttgt tccatccatg atctagaagc cgctcaagaa tacgctttga gattaaagaa    1380
```

```
attgtcagat gaattaaaag gtgatttatc catcattatg agagcatact tggagaagcc      1440
aagaacaacc gtcggctgga aaggtctaat taatgaccct gatgttaaca acactttcaa      1500
catcaacaag ggtttgcaat ccgctagaca attgtttgtc aacttgacaa atatcggttt      1560
gccaattggt tctgaaatgc ttgataccat ttctcctaaa tacttggctg atttggtctc      1620
cttcggtgcc attggtgcca gaaccaccga atctcaactg cacagagaat tggcctccgg      1680
tttgtctttc ccagttggtt tcaagaacgg taccgatggt accttaaatg ttgctgtgga      1740
tgcttgtcaa gccgctgctc attctcacca tttcatgggt gttactaagc atggtgttgc      1800
tgctatcacc actactaagg gtaacgaaca ctgcttcgtt attctaagag gtggtaaaaa      1860
gggtaccaac tacgacgcta agtccgttgc agaagctaag gctcaattgc ctgccggttc      1920
caacggtcta atgattgact actctcacgg taactccaat aaggatttca gaaaccaacc      1980
aaaggtcaat gacgttgttt gtgagcaaat cgctaacggt gaaaacgcca ttaccggtgt      2040
catgattgaa tcaaacatca acgaaggtaa ccaaggcatc ccagccgaag gtaaagccgg      2100
cttgaaatat ggtgtttcca tcactgatgc ttgtataggt tgggaaacta ctgaagacgt      2160
cttgaggaaa ttggctgctg ctgtcagaca agaagagaa gttaacaaga aatagatgtt       2220
tttttaatga tatatgtaac gtacattctt tcctctacca ctgccaattc ggtattattt      2280
aattgtgttt agcgctattt actaattaac tagaaactca atttttaaag gcaaagctcg      2340 ctgaccttc actgatttcg tggatgttat actatcagtt actcttctgc aaaaaaaat       2400 tgagtcatat cgtagctttg ggattatttt tctctctctc cacggctaat taggtgatca      2460
tgaaaaaatg aaaaattcat gagaaaagag tcagacatcg aaacatacat aagttgatat      2520
tcctttgata tcgacgacta ctcaatcagg ttttaaaaga aaagaggcag ctattgaagt      2580
agcagtatcc agtttaggtt ttttaattat ttacaagtaa agaaaaagag aatgccggtc      2640
gttcacgata acttcgtata atgtatgcta tacgaagtta tgcggccgcg agaagatgcg      2700
gccagcaaaa ctaaaaaact gtattataag taaatgcatg tatactaaac tcacaaatta      2760
gagcttcaat ttaattatat cagttattac ccgggaatct cggtcgtaat gatttctata      2820
atgacgaaaa aaaaaaatt ggaaagaaaa agcttcatgg cctttataaa aaggaactat       2880
ccaatacctc gccagaacca agtaacagta ttttacgggg cacaaatcaa gaacaataag      2940
acaggactgt aaagatggac gcattgaact ccaaagaaca acaagagttc aaaaagtag      3000 tggaacaaaa gcaaatgaag gatttcatgc gtttgtactc taatctggta gaaagatgtt      3060
tcacagactg tgtcaatgac ttcacaacat caaagctaac caataaggaa caaacatgca      3120
tcatgaagtg ctcagaaaag ttcttgaagc atagcgaacg tgtagggcag cgtttccaag      3180
ag                                                                    3182

<210> SEQ ID NO 2
<211> LENGTH: 3275
<212> TYPE: DNA
<213> ORGANISM: Artificial Sequence
<220> FEATURE:
<223> OTHER INFORMATION: pCM520 transformation fragment

<400> SEQUENCE: 2
cctactgcgc caattgatga caatacagac gatgataaca aaccgaagtt atctgatgta        60
gaaaaggatt aaagatgcta agagatagtg atgatatttc ataaataatg taattctata       120
tatgttaatt acctttttg cgaggcatat ttatggtgaa gaataagttt tgaccatcaa        180
```

```
agaaggttaa tgtggctgtg gtttcagggt ccataaagct tttcaattca tcattttttt    240
tttattcttt tttttgattc cggtttcctt gaaattttt tgattcggta atctccgaac    300
agaaggaaga acgaaggaag gagcacagac ttagattggt atatatacgc atatgtagtg    360
ttgaagaaac atgaaattgc ccagtattct taacccaact gcacagaaca aaaatctgca    420
ggaaacgaag ataaagcggc cgcataactt cgtatagcat acattatacg aagttatcgc    480
ctgttaagat ataactgaaa aaagagggga atttttagat actgaaatga tattttagaa    540
taaccagact atatataagg ataaattaca aaaattaac taatagataa gatttaaata    600
taaaagatat gcaactagaa aagtcttatc aatctcctta tggagtgacg acgttaccca    660
acaatttacc gacttcttcg gcgatagcca aagttctctc ttcggacaat cttctaccaa    720
taacttgaac agcaacagga gcaccgtgat aagcctctgg gtcgtattct tcttgaacca    780
aagcatccaa ttcggaaaca gctttaaaag attcgttctt cttatcaata ttcttatcag    840
cgaaagtgac tgggacgaca acagaggtga atccaataa gttaataacg gaggcgtaac    900
cgtagtatct gaattgatcg tgtctgacag cggcggtagg agtaattgga gcgataatag    960
cgtccaattc cttaccagct ttttcttcag cttcacgcca cttttccaag tattccattt    1020
gatagttcca cttttgtaaa tgagtgtccc acaattcgtt catgttaaca gccttaatat    1080
ttgggttcaa caagtcctta atgttaggga tggctggctc accagaggca gaaatgtctc    1140
tcatgacgtc ggcagaacca tcagcagcat agatgtggga aatcaagtca tgaccgaaat    1200
catgcttgta tggagtccat ggagtaacgg tgtgaccagc cttggccaaa gcggcaacgg    1260
tagtttcgac accacgtaaa attggtgggt gtggcaagac gttaccgtcg aaattgtaat    1320
aaccaatgtt caaaccacca ttcttaatct tagaggcaat gatgtcagat tcagattgtc    1380
tccatggcat tgggatgacc ttagagtcgt acttccaagg ttcttgaccc aagacagatt    1440
tggtgaacaa tctcaagtct tcgacggagt gagtgatagg accaacgacg gagtgaacgg    1500
tttcttgacc ttccatagag ttagccattt tagcatatgg caatctaccg tgagatggtc    1560
tcaaaccgta taaaaagttg aaagcagctg ggactctaat ggaaccacca atgtcagtac    1620
cgacaccaat aacaccacct ctaataccaa caatagcacc ttcaccacca gaagaaccac    1680
cacaggacca atttttgttt cttggattga cagttctacc aatgatgttg ttgacggttt    1740
cacagaccat caaggtttgt gggacagagg tcttaacgta gaaaacagca ccagcttttc    1800
tcaacatggt ggttaagacg gaatcacctt catcgtattt gtttaaccag gaaatgtaac    1860
ccatggaggt ttcgtaaccc ttaacacgca attggtcctt taaagagatt ggtaaaccgt    1920
gtaatggacc aactggtctc ttatgcttag cgtagtattc atctaattct ctagcttgag    1980
ctaaagcagc atctgggaag aattcgtgag cacagttggt taattgttga gcaatagcag    2040
ctctcttaca aaaagccaaa gtgacttcaa cagaagtcaa ctcaccagcg gccaacttgg    2100
agaccaaatc agcagcagag gcttcggtaa tcttcaattc agcctcagac aaaataccgg    2160
acttctttgg gaaatcaata acggaatctt cggcaggcaa gtttgaacc ttccattcgt    2220 caggaatggt tttagccaaa cgggcacgtt tgtcggcggc caattcttcc caggattgtg    2280
gcatttgtta attaaaactt agattagatt gctatgcttt ctttctaatg agcaagaagt    2340
aaaaaaagtt gtaatagaac aagaaaaacg aaactgaaac ttgagaaatt gaagaccatt    2400
tattaactta aatatcaatg ggaggtcatc gaaagagaaa aaaatcaaaa aaaaattttt    2460
tcaagaaaaa gaaacgtgat aaaaattttt attgcctttt tcgacgaaga aaagaaacg    2520 aggcggtctc ttttttcttt tccaaacctt tagtacgggt aattaacgcc accctagagg    2580
```

```
aagaaagagg ggaaatttag tatgctgtgc ttgggtgttt tgaagtggta cggcgatgcg      2640
cggagtccga gaaatctgg aagagtaaaa aaggagtaga acattttga agctatggtg       2700 tgtgggggat cacttgtggg ggattgggtg tgatgtaagg ataacttcgt atagcataca     2760
ttatacgaag ttatgcggcc gcgagaagat gcggccagca aaactaaaaa actgtattat    2820
aagtaaatgc atgtatacta aactcacaaa ttagagcttc aatttaatta tatcagttat    2880
tacccgggaa tctcggtcgt aatgattttt ataatgacga aaaaaaaaa attggaaaga     2940 aaaagcttca tggcctttat aaaaaggaac catccaatac ctcgccagaa ccaagtaaca    3000
gtattttacg gggcacaaat caagaacaat aagacaggac tgtaaagatg gacgcattga    3060
actccaaaga acaacaagag ttccaaaaag tagtggaaca aaagcaaatg aaggatttca    3120 tgcgttgta ctctaatctg gtagaaagat gttttacaga ctgtgtcaat gacttcacaa     3180
catcaaagct aaccaataag gaacaaacat gcatcatgaa gtgctcagaa aagttcttga    3240
agcatagcga acgtgtaggg cagcgtttcc aagag                                3275
```

<210> SEQ ID NO 3
<211> LENGTH: 1132
<212> TYPE: DNA
<213> ORGANISM: Artificial Sequence
<220> FEATURE:
<223> OTHER INFORMATION: cre PCR fragment

<400> SEQUENCE: 3

```
ctcttttta cagatcatca aggaagtaat tatctacttt ttacaagaat tcatgtctaa        60
tttacttact gttcaccaaa acttgcctgc attaccagtt gacgcaacct ccgatgaagt     120
cagaaagaac cttatggata tgtttagaga tagacaagct ttctccgaac atacttggaa    180
aatgttatta tccgtttgta gatcctgggc cgcttggtgt aaacttaaca atagaaaatg    240
gtttcctgct gaaccagaag acgtcagaga ttacttactt tacttacaag ctagaggttt    300
ggctgttaaa actatccaac aacacttagg tcaattgaat atgttacaca gaagatccgg    360
tttaccaaga ccatccgatt ccaacgcagt ttcccttgtt atgagaagaa ttagaaaaga    420
aaatgttgac gctggtgaaa gagctaaaca agcattagca tttgaaagaa ccgatttcga    480
tcaagttaga tccttaatgg aaaattccga tagatgtcaa gatattgaaa acttagcttt    540
cttaggtatt gcttacaaca cattattaag aatcgctgaa attgctagaa ttagagttaa    600
agatatttca agaaccgatg gcggtagaat gttaatccac attggcagaa caaaaaccttt   660 agtctccaca gcaggcgtcg aaaaagcatt atcattaggt gttactaaat tagttgaacg    720
ttggatttcc gtttccggtg ttgcagatga cccaaacaac tacttattct gtcgtgttag    780
aaaaaatggt gttgccgctc cttccgctac ctcacaatta tccacaagag cattagaagg    840 cattttgaa gctacccaca gacttattta tggtgcaaaa gacgattccg gtcaaagata     900
tttagcttgg tctggtcatt ccgctagagt tggtgccgca agagacatgg caagagctgg    960
tgtttctatt cctgaaatta tgcaagccgg tggttggact aatgttaaca ttgttatgaa   1020
ctatatcaga aacttagatt ccgaaacagg tgctatggtt agattacttg aagacggtga   1080
ttaagctagc taagatccgc tctaaccgaa aaggaaggag ttagacaacc tg            1132
```

<210> SEQ ID NO 4
<211> LENGTH: 6376
<212> TYPE: DNA
<213> ORGANISM: Artificial Sequence
<220> FEATURE:

<223> OTHER INFORMATION: pGP52 fragment

<400> SEQUENCE: 4

```
ctagctaaga tccgctctaa ccgaaaagga aggagttaga caacctgaag tctaggtccc      60
tatttatttt tttatagtta tgttagtatt aagaacgtta tttatatttc aaattttttct    120
ttttttttctg tacagacgcg tgtacgcatg taacattata ctgaaaacct tgcttgagaa    180
ggttttggga cgctcgaaga tccagctgca ttaatgaatc ggccaacgcg cggggagagg    240
cggtttgcgt attgggcgct cttccgcttc ctcgctcact gactcgctgc gctcggtcgt    300
tcggctgcgg cgagcggtat cagctcactc aaaggcggta atacggttat ccacagaatc    360
aggggataac gcaggaaaga acatgtgagc aaaaggccag caaaaggcca ggaaccgtaa    420
aaaggccgcg ttgctggcgt ttttccatag gctccgcccc cctgacgagc atcacaaaaa    480
tcgacgctca agtcagaggt ggcgaaaccc gacaggacta taaagatacc aggcgtttcc    540
ccctggaagc tccctcgtgc gctctcctgt tccgaccctg ccgcttaccg gatacctgtc    600
cgcctttctc ccttcgggaa gcgtggcgct ttctcatagc tcacgctgta ggtatctcag    660
ttcggtgtag tcgttcgct ccaagctggg ctgtgtgcac gaaccccccg ttcagcccga    720
ccgctgcgcc ttatccggta actatcgtct gagtccaac ccggtaagac acgacttatc    780
gccactggca gcagccactg gtaacaggat tagcagagcg aggtatgtag gcggtgctac    840
agagttcttg aagtggtggc ctaactacgg ctacactaga aggacagtat ttggtatctg    900
cgctctgctg aagccagtta ccttcggaaa aagagttggt agctcttgat ccggcaaaca    960
aaccaccgct ggtagcggtg gtttttttgt ttgcaagcag cagattacgc gcagaaaaaa  1020
aggatctcaa gaagatcctt tgatctttc tacggggtct gacgctcagt ggaacgaaaa  1080
ctcacgttaa gggattttgg tcatgagatt atcaaaaagg atcttcacct agatcctttt  1140
aaattaaaaa tgaagtttta atcaatcta agtatatat gagtaaactt ggtctgacag    1200
ttaccaatgc ttaatcagtg aggcaccat ctcagcgatc tgtctatttc gttcatccat    1260
agttgcctga ctccccgtcg tgtagataac tacgatacgg gagggcttac catctggccc  1320
cagtgctgca atgataccgc gagacccacg ctcaccggct ccagatttat cagcaataaa  1380
ccagccagcc ggaagggccg agcgcagaag tggtcctgca actttatccg cctccatcca  1440
gtctattaat tgttgccggg aagctagagt aagtagttcg ccagttaata gtttgcgcaa  1500
cgttgttgcc attgctacag gcatcgtggt gtcacgctcg tcgtttggta tggcttcatt  1560
cagctccggt tcccaacgat caaggcgagt tacatgatcc cccatgttgt gcaaaaaagc  1620
ggttagctcc ttcggtcctc cgatcgttgt cagaagtaag ttggccgcag tgttatcact  1680
catggttatg gcagcactgc ataattctct tactgtcatg ccatccgtaa gatgcttttc  1740
tgtgactggt gagtactcaa ccaagtcatt ctgagaatag tgtatgcggc gaccgagttg  1800
ctcttgcccg gcgtcaatac gggataatac cgcgccacat agcagaactt aaaagtgct  1860
catcattgga aaacgttctt cggggcgaaa actctcaagg atcttaccgc tgttgagatc  1920
cagttcgatg taacccactc gtgcacccaa ctgatcttca gcatctttta ctttcaccag  1980
cgtttctggg tgagcaaaaa caggaaggca aaatgccgca aaaagggaa taagggcgac  2040
acggaaatgt tgaatactca tactcttcct ttttcaatat tattgaagca tttatcaggg  2100
ttattgtctc atgagcggat acatatttga atgtatttag aaaaataaac aaataggggt  2160
tccgcgcaca tttccccgaa aagtgccacc tgaacgaagc atctgtgctt cattttgtag  2220
aacaaaaatg caacgcgaga gcgctaattt ttcaaacaaa gaatctgagc tgcatttta  2280
```

```
cagaacagaa atgcaacgcg aaagcgctat tttaccaacg aagaatctgt gcttcatttt    2340
tgtaaaacaa aaatgcaacg cgagagcgct aattttcaa acaaagaatc tgagctgcat     2400
ttttacagaa cagaaatgca acgcgagagc gctattttac caacaaagaa tctatacttc    2460 tttttgttc tacaaaaatg catcccgaga gcgctatttt tctaacaaag catcttagat     2520 tactttttt ctcctttgtg cgctctataa tgcagtctct tgataacttt ttgcactgta     2580
ggtccgttaa ggttagaaga aggctacttt ggtgtctatt ttctcttcca taaaaaaagc    2640
ctgactccac ttcccgcgtt tactgattac tagcgaagct gcgggtgcat ttttcaaga    2700 taaaggcatc cccgattata ttctataccg atgtggattg cgcatacttt gtgaacagaa    2760
agtgatagcg ttgatgattc ttcattggtc agaaaattat gaacggtttc ttctattttg    2820
tctctatata ctacgtatag gaatgtttta cattttcgta ttgttttcga ttcactctat    2880
gaatagttct tactacaatt ttttgtcta aagagtaata ctagagataa acataaaaaa     2940
tgtagaggtc gagtttagat gcaagttcaa ggagcgaaag gtggatgggt aggttatata    3000
gggatatagc acagagatat atagcaaaga gatactttg agcaatgttt gtggaagcgg     3060
tattcgcaat attttagtag ctcgttacag tccggtgcgt ttttggtttt ttgaaagtgc    3120
gtcttcagag cgcttttggt tttcaaaagc gctctgaagt tcctatactt tctagagaat    3180
aggaacttcg gaataggaac ttcaaagcgt ttccgaaaac gagcgcttcc gaaaatgcaa    3240
cgcgagctgc gcacatacag ctcactgttc acgtcgcacc tatatctgcg tgttgcctgt    3300
atatatatat acatgagaag aacggcatag tgcgtgttta tgcttaaatg cgtacttata    3360
tgcgtctatt tatgtaggat gaaaggtagt ctagtacctc ctgtgatatt atcccattcc    3420
atgcggggta tcgtatgctt ccttcagcac tacccttag ctgttctata tgctgccact     3480
cctcaattgg attagtctca tccttcaatg ctatcatttc ctttgatatt ggatcatact    3540
aagaaaccat tattatcatg acattaacct ataaaaatag gcgtatcacg aggccctttc    3600
gtctcgcgcg tttcggtgat gacggtgaaa acctctgaca catgcagctc ccggagacgg    3660
tcacagcttg tctgtaagcg gatgccggga gcagacaagc ccgtcagggc gcgtcagcgg    3720
gtgttggcgg gtgtcgggc tggcttaact atgcggcatc agagcagatt gtactgagag    3780
tgcaccatac cacagctttt caattcaatt catcattttt tttttattct ttttttgat    3840 ttcggtttct ttgaattttt tttgattcgg taatctccga acagaaggaa gaacgaagga    3900
aggagcacag acttagattg gtatatatac gcatatgtag tgttgaagaa acatgaaatt    3960
gcccagtatt cttaacccaa ctgcacagaa caaaaacctg caggaaacga agataaatca    4020
tgtcgaaagc tacatataag gaacgtgctg ctactcatcc tagtcctgtt gctgccaagc    4080
tatttaatat catgcacgaa aagcaaacaa acttgtgtgc ttcattggat gttcgtacca    4140
ccaaggaatt actggagtta gttgaagcat taggtcccaa aatttgttta ctaaaaacac    4200
atgtggatat cttgactgat ttttccatgg agggcacagt taagccgcta aaggcattat    4260
ccgccaagta caatttttta ctcttcgaag acagaaaatt tgctgacatt ggtaatacag    4320
tcaaattgca gtactctgcg ggtgtataca gaatagcaga atgggcagac attacgaatg    4380
cacacggtgt ggtgggccca ggtattgtta gcggtttgaa gcaggcggca gaagaagtaa    4440
caaaggaacc tagaggcctt ttgatgttag cagaattgtc atgcaagggc tccctatcta    4500
ctggagaata tactaagggt actgttgaca ttgcgaagag cgacaaagat tttgttatcg    4560
gctttattgc tcaaagagac atgggtggaa gagatgaagg ttacgattgg ttgattatga    4620
```

```
cacccggtgt gggtttagat gacaagggag acgcattggg tcaacagtat agaaccgtgg    4680
atgatgtggt ctctacagga tctgacatta ttattgttgg aagaggacta tttgcaaagg    4740
gaagggatgc taaggtagag ggtgaacgtt acagaaaagc aggctgggaa gcatatttga    4800
gaagatgcgg ccagcaaaac taaaaaactg tattataagt aaatgcatgt atactaaact    4860
cacaaattag agcttcaatt taattatatc agttattacc ctatgcggtg tgaaataccg    4920
cacagatgcg taaggagaaa ataccgcatc aggaaattgt aaacgttaat attttgttaa    4980
aattcgcgtt aaattttgt taaatcagct catttttaa ccaataggcc gaaatcggca    5040 aaatcccta taaatcaaaa gaatagaccg ataggggtt gagtgttgtt ccagtttgga    5100
acaagagtcc actattaaag aacgtggact ccaacgtcaa agggcgaaaa accgtctatc    5160
agggcgatgg cccactacgt gaaccatcac cctaatcaag ttttttgggg tcgaggtgcc    5220
gtaaagcact aaatcggaac cctaaaggga gcccccgatt tagagcttga cggggaaagc    5280
cggcgaacgt ggcgagaaag gaagggaaga aagcgaaagg agcgggcgct agggcgctgg    5340
caagtgtagc ggtcacgctg cgcgtaacca ccacacccgc cgcgcttaat gcgccgctac    5400
agggcgcgtc cattcgccat tcaggctgcg caactgttgg gaagggcgat cggtgcgggc    5460
ctcttcgcta ttacgccagc tgaattggag cgacctcatg ctatacctga aaagcaacc    5520 tgacctacag gaaagagtta ctcaagaata agaatttcg ttttaaaacc taagagtcac    5580
tttaaaattt gtatacactt attttttta aacttatt aataataaaa atcataaatc    5640
ataagaaatt cgcttattta gaagtgtcaa caacgtatct accaacgatt tgaccctttt    5700
ccatcttttc gtaaatttct ggcaaggtag acaagccgac aaccttgatt ggagacttga    5760
ccaaacctct ggcgaagaat tgttaattaa gccagaaaaa ggaagtgttt ccctccttct    5820
tgaattgatg ttaccctcat aaagcacgtg gcctcttatc gagaaagaaa ttaccgtcgc    5880
tcgtgatttg tttgcaaaaa gaacaaaact gaaaaaaccc agacacgctc gacttcctgt    5940
cttcctattg attgcagctt ccaatttcgt cacacaacaa ggtcctagcg acggctcaca    6000
ggttttgtaa caagcaatcg aaggttctgg aatggcggga aagggtttag taccacatgc    6060
tatgatgccc actgtgatct ccagagcaaa gttcgttcga tcgtactgtt actctctctc    6120
tttcaaacag aattgtccga atcgtgtgac aacaacagcc tgttctcaca cactcttttc    6180
ttctaaccaa gggggtggtt tagtttagta gaacctcgtg aaacttacat ttacatatat    6240
ataaacttgc ataaattggt caatgcaaga aatacatatt tggtcttttc taattcgtag    6300
tttttcaagt tcttagatgc tttcttttc tcttttttac agatcatcaa ggaagtaatt    6360
atctactttt tacaag                                                   6376
```

<210> SEQ ID NO 5
<211> LENGTH: 7380
<212> TYPE: DNA
<213> ORGANISM: Artificial Sequence
<220> FEATURE:
<223> OTHER INFORMATION: pTAN06

<400> SEQUENCE: 5

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc ttttttttga tttcggtttc     240
tttgaaattt ttttgattcg gtaatctccg aacagaagga agaacgaagg aaggagcaca     300
```

-continued

```
gacttagatt ggtatatata cgcatatgta gtgttgaaga acatgaaat tgcccagtat      360 tcttaaccca actgcacaga acaaaaacct gcaggaaacg aagataaatc atgtcgaaag      420
ctacatataa ggaacgtgct gctactcatc ctagtcctgt tgctgccaag ctatttaata      480
tcatgcacga aaagcaaaca aacttgtgtg cttcattgga tgttcgtacc accaaggaat      540
tactggagtt agttgaagca ttaggtccca aaatttgttt actaaaaaca catgtggata      600
tcttgactga tttttccatg gagggcacag ttaagccgct aaaggcatta tccgccaagt      660
acaatttttt actcttcgaa gacagaaaat ttgctgacat tggtaataca gtcaaattgc      720
agtactctgc gggtgtatac agaatagcag aatgggcaga cattacgaat gcacacggtg      780
tggtgggccc aggtattgtt agcggtttga agcaggcggc agaagaagta acaaaggaac      840
ctagaggcct tttgatgtta gcagaattgt catgcaaggg ctccctatct actggagaat      900
atactaaggg tactgttgac attgcgaaga gcgacaaaga ttttgttatc ggctttattg      960
ctcaaagaga catgggtgga agagatgaag gttacgattg gttgattatg acacccggtg     1020
tgggtttaga tgacaaggga gacgcattgg gtcaacagta tagaaccgtg gatgatgtgg     1080
tctctacagg atctgacatt attattgttg aagaggact atttgcaaag ggaagggatg      1140
ctaaggtaga gggtgaacgt tacagaaaag caggctggga agcatatttg agaagatgcg     1200
gccagcaaaa ctaaaaaact gtattataag taaatgcatg tatactaaac tcacaaatta     1260
gagcttcaat ttaattatat cagttattac cctgcggtgt gaaataccgc acagatgcgt     1320
aaggagaaaa taccgcatca ggaaattgta aacgttaata ttttgttaaa attcgcgtta     1380 aattttgtt aaatcagctc attttttaac caataggccg aaatcggcaa atcccttat      1440 aaatcaaaag aatagaccga gatagggttg agtgttgttc cagtttggaa caagagtcca     1500
ctattaaaga acgtggactc caacgtcaaa gggcgaaaaa ccgtctatca gggcgatggc     1560
ccactacgtg aaccatcacc ctaatcaagt ttttggggt cgaggtgccg taaagcacta      1620
aatcggaacc ctaaagggag ccccgattt agagcttgac ggggaaagcc ggcgaacgtg      1680
gcgagaaagg aagggaagaa agcgaaagga gcgggcgcta gggcgctggc aagtgtagcg     1740
gtcacgctgc gcgtaaccac cacacccgcc gcgcttaatg cgccgctaca gggcgcgtcg     1800
cgccattcgc cattcaggct gcgcaactgt tgggaagggc gatcggtgcg ggcctcttcg     1860
ctattacgcc agctggcgaa ggggggatgt gctgcaaggc gattaagttg ggtaacgcca     1920
gggttttccc agtcacgacg ttgtaaaacg acggccagtg aattgtaata cgactcacta     1980
tagggcgaat tggagctcca ccgcggtggc ggccgcctcg agatctcccc taaaccgtgg     2040
aatatttcgg atatccttt gttgtttccg ggtgtacaat atggacttcc tcttttctgg      2100
caaccaaacc catacatcgg gattcctata ataccttcgt tggtctccct aacatgtagg     2160
tggcggaggg gagatataca atagaacaga taccagacaa gacataatgg gctaaacaag     2220
actacaccaa ttcactgcc tcattgatgg tggtacataa cgaactaata ctgtagccct      2280
agacttgata gccatcatca tatcgaagtt tcactaccct ttttccattt gccatctatt     2340
gaagtaataa taggcgcatg caacttcttt tctttttttt tcttttctct ctccccgtt      2400 gttgtctcac catatccgca atgacaaaaa aatgatggaa gacactaaag gaaaaaatta     2460
acgacaaaga cagcaccaac agatgtcgtt gttccagagc tgatgggggg tatctcgaag     2520
cacacgaaac ttttttcctc cttcattcac gcacactact ctctaatgag caacggtata     2580
cggccttcct tccagttact tgaatttgaa ataaaaaaag tttgctgtct tgctatcaag     2640
```

-continued

```
tataaataga cctgcaatta ttaatctttt gtttcctcgt cattgttctc gttcccttc    2700
ttccttgttt cttttttctgc acaatatttc aagctatacc aagcatacaa tcaactatct   2760
catatacaat gatcagattg accgttttct tgaccgctgt ttttgctgct gttgcttctt    2820
gtgttccagt tgaattggat aagagaaaca ccggtcattt ccaagcttat tctggttata    2880
ccgttgctag atctaacttc acccaatgga ttcatgaaca accagctgtt tcttggtact    2940
acttgttgca aaacatcgat tacccagaag gtcaattcaa atctgctaaa ccaggtgttg    3000
ttgttgcttc tccatctaca tctgaaccag attacttcta ccaatggact agagataccg    3060
ctattacctt cttgtccttg attgctgaag ttgaagatca ttctttctcc aacactacct    3120
tggctaaggt tgtcgaatat tacatttcca acacctacac cttgcaaaga gtttctaatc    3180
catccggtaa cttcgattct ccaaatcatg atggtttggg tgaacctaag ttcaacgttg    3240
atgatactgc ttatacagct tcttggggta gaccacaaaa tgatggtcca gctttgagag    3300
cttacgctat ttctagatac ttgaacgctg ttgctaagca caacaacggt aaattattat    3360
tggccggtca aaacggtatt ccttattctt ctgcttccga tatctactgg aagattatta    3420
agccagactt gcaacatgtt tctactcatt ggtctacctc tggttttgat ttgtgggaag    3480
aaaatcaagg tactcatttc ttcaccgctt tggttcaatt gaaggctttg tcttacggta    3540
ttccattgtc taagacctac aatgatccag gtttcacttc ttggttggaa aaacaaaagg    3600
atgccttgaa ctcctacatt aactcttccg gtttcgttaa ctctggtaaa aagcacatcg    3660
ttgaatctcc acaattgtca tctagaggtg gtttggattc tgctacttat attgctgcct    3720
tgatcaccca tgatatcggt gatgatgata cttacacccc attcaatgtt gataactcct    3780
acgttttgaa ctccttgtat tacctattgg tcgacaacaa gaacagatac aagatcaacg    3840
gtaactacaa agctggtgct gctgttggta gatatcctga agatgtttac aacggtgttg    3900
gtacttctga aggtaatcca tggcaattgg ctactgctta tgctggtcaa acttttttaca    3960
ccttggccta caattccttg aagaacaaga agaacttggt catcgaaaag ttgaactacg    4020
acttgtacaa ctccttcatt gctgatttgt ccaagattga ttcttcctac gcttctaagg    4080
attctttgac tttgacctac ggttccgata actacaagaa cgttatcaag tccttgttgc    4140
aattcggtga ctcattcttg aaggttttgt tggatcacat cgatgacaac ggtcaattga    4200
ctgaagaaat caacagatac accgttttc aagctggtgc agtttctttg acttggtcat    4260
ctggttcttt gttgtctgct aatagagcca gaaacaagtt gatcgaatta ttgtaaacag    4320
gccccttttc ctttgtcgat atcatgtaat tagttatgtc acgcttacat tcacgccctc    4380
ctcccacatc cgctctaacc gaaaaggaag gagttagaca acctgaagtc taggtcccta    4440
tttattttt tatagttatg ttagtattaa gaacgttatt tatatttcaa attttctttt     4500
ttttttctgta caaacgcgtg tacgcatgta acgggcagac gaattcgata tcaagcttat    4560
cgataccgtc gacctcgagg gggggcccgg taccagcttt tgttcccttt agtgagggtt    4620
aattccgagc ttggcgtaat catggtcata gctgtttcct gtgtgaaatt gttatccgct    4680
cacaattcca cacaacatag gagccggaag cataaagtgt aaagcctggg gtgcctaatg    4740
agtgaggtaa ctcacattaa ttgcgttgcg ctcactgccc gctttccagt cgggaaacct    4800
gtcgtgccag ctgcattaat gaatcggcca acgcgcgggg agaggcggtt tgcgtattgg    4860
gcgctcttcc gcttcctcgc tcactgactc gctgcgctcg gtcgttcggc tcggcgagc    4920
ggtatcagct cactcaaagg cggtaatacg gttatccaca gaatcagggg ataacgcagg    4980
aaagaacatg tgagcaaaag gccagcaaaa ggccaggaac cgtaaaaagg ccgcgttgct    5040
```

```
ggcgttttc  cataggctcg  gccccccctga  cgagcatcac  aaaaatcgac  gctcaagtca   5100
gaggtggcga  aacccgacag  gactataaag  ataccaggcg  ttccccctg   gaagctccct   5160
cgtgcgctct  cctgttccga  ccctgccgct  taccggatac  ctgtccgcct  ttctcccttc   5220
gggaagcgtg  gcgctttctc  aatgctcacg  ctgtaggtat  ctcagttcgg  tgtaggtcgt   5280
tcgctccaag  ctgggctgtg  tgcacgaacc  ccccgttcag  cccgaccgct  gcgccttatc   5340
cggtaactat  cgtcttgagt  ccaacccggt  aagacacgac  ttatcgccac  tggcagcagc   5400
cactggtaac  aggattagca  gagcgaggta  tgtaggcggt  gctacagagt  tcttgaagtg   5460
gtggcctaac  tacggctaca  ctagaaggac  agtatttggt  atctgcgctc  tgctgaagcc   5520
agttaccttc  ggaaaaagag  ttggtagctc  ttgatccggc  aaacaaacca  ccgctggtag   5580
cggtggtttt  tttgtttgca  agcagcagat  tacgcgcaga  aaaaaaggat  ctcaagaaga   5640
tcctttgatc  ttttctacgg  ggtctgacgc  tcagtggaac  gaaaactcac  gttaagggat   5700
tttggtcatg  agattatcaa  aaaggatctt  cacctagatc  cttttaaatt  aaaaatgaag   5760
ttttaaatca  atctaaagta  tatatgagta  aacttggtct  gacagttacc  aatgcttaat   5820
cagtgaggca  cctatctcag  cgatctgtct  atttcgttca  tccatagttg  cctgactgcc   5880
cgtcgtgtag  ataactacga  tacgggaggg  cttaccatct  ggccccagtg  ctgcaatgat   5940
accgcgagac  ccacgctcac  cggctccaga  tttatcagca  ataaaccagc  cagccggaag   6000
ggccgagcgc  agaagtggtc  ctgcaacttt  atccgcctcc  atccagtcta  ttaattgttg   6060
ccgggaagct  agagtaagta  gttcgccagt  taatagtttg  cgcaacgttg  ttgccattgc   6120
tacaggcatc  gtggtgtcac  gctcgtcgtt  tggtatggct  tcattcagct  ccggttccca   6180
acgatcaagg  cgagttacat  gatcccccat  gttgtgaaaa  aaagcggtta  gctccttcgg   6240
tcctccgatc  gttgtcagaa  gtaagttggc  cgcagtgtta  tcactcatgg  ttatggcagc   6300
actgcataat  tctcttactg  tcatgccatc  cgtaagatgc  ttttctgtga  ctggtgagta   6360
ctcaaccaag  tcattctgag  aatagtgtat  gcggcgaccg  agttgctctt  gcccggcgtc   6420
aatacgggat  aataccgcgc  cacatagcag  aactttaaaa  gtgctcatca  ttggaaaacg   6480
ttcttcgggg  cgaaaactct  caaggatctt  accgctgttg  agatccagtt  cgatgtaacc   6540
cactcgtgca  cccaactgat  cttcagcatc  ttttactttc  accagcgttt  ctgggtgagc   6600
aaaaacagga  aggcaaaatg  ccgcaaaaaa  gggaataagg  gcgacacgga  aatgttgaat   6660
actcatactc  ttcctttttc  aatattattg  aagcatttat  cagggttatt  gtctcatgag   6720
cggatacata  tttgaatgta  tttagaaaaa  taaacaaata  ggggttccgc  gcacatttcc   6780
ccgaaaagtg  ccacctgggt  cctttcatc   acgtgctata  aaataatta   taatttaaat   6840
tttttaatat  aaatatataa  attaaaaata  gaaagtaaaa  aaagaaatta  agaaaaaat   6900
agttttgtt   ttccgaagat  gtaaaagact  ctagggggat  cgccaacaaa  tactaccttt   6960
tatcttgctc  ttcctgctct  caggtattaa  tgccgaattg  tttcatcttg  tctgtgtaga   7020
agaccacaca  cgaaaatcct  gtgattttac  attttactta  tcgttaatcg  aatgtatatc   7080
tatttaatct  gcttttcttg  tctaataaat  atatatgtaa  agtacgcttt  ttgttgaaat   7140
tttttaaacc  tttgttatt   ttttttcct   cattccgtaa  ctcttctacc  ttctttattt   7200
actttctaaa  atccaaatac  aaaacataaa  aataaataaa  cacagagtaa  attcccaaat   7260
tattccatca  ttaaaagata  cgaggcgcgt  gtaagttaca  ggcaagcgat  ccgtcctaag   7320
aaaccattat  tatcatgaca  ttaacctata  aaaataggcg  tatcacgagg  cccttcgtc   7380
```

<210> SEQ ID NO 6
<211> LENGTH: 7383
<212> TYPE: DNA
<213> ORGANISM: Artificial Sequence
<220> FEATURE:
<223> OTHER INFORMATION: pAV33

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt tttttattc tttttttga tttcggtttc       240
tttgaaattt ttttgattcg gtaatctccg aacagaagga agaacgaagg aaggagcaca     300
gacttagatt ggtatatata cgcatatgta gtgttgaaga acatgaaat tgcccagtat      360
tcttaaccca actgcacaga acaaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aaatttgttt actaaaaaca catgtggata     600
tcttgactga ttttccatg gagggcacag ttaagccgct aaaggcatta tccgccaagt     660
acaatttttt actcttcgaa gacagaaaat ttgctgacat tggtaataca gtcaaattgc     720
agtactctgc gggtgtatac agaatagcag aatgggcaga cattacgaat gcacacggtg     780
tggtgggccc aggtattgtt agcggtttga agcaggcggc agaagaagta acaaaggaac     840
ctagaggcct tttgatgtta gcagaattgt catgcaaggg ctccctatct actggagaat     900
atactaaggg tactgttgac attgcgaaga gcgacaaaga ttttgttatc ggctttattg     960
ctcaaagaga catgggtgga agagatgaag gttacgattg gttgattatg acacccggtg    1020
tgggtttaga tgacaaggga gacgcattgg gtcaacagta tagaaccgtg gatgatgtgg    1080
tctctacagg atctgacatt attattgttg gaagaggact atttgcaaag ggaagggatg    1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta acgttaata ttttgttaaa attcgcgtta    1380
aattttgtt aaatcagctc attttttaac caataggccg aaatcggcaa atcccttat    1440
aaatcaaaag aatagaccga gatagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttggggt cgaggtgccg taaagcacta    1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
gggttttccc agtcacgacg ttgtaaaacg acggccagtg aattgtaata cgactcacta    1980
tagggcgaat tggagctcca ccgcggtggc ggccgctcg agatctcccc taaaccgtgg    2040
aatatttcgg atatcctttt gttgtttccg ggtgtacaat atggacttcc tcttttctgg    2100
```

```
caaccaaacc catacatcgg gattcctata ataccttcgt tggtctccct aacatgtagg    2160
tggcggaggg gagatataca atagaacaga taccagacaa gacataatgg gctaaacaag    2220
actacaccaa ttacactgcc tcattgatgg tggtacataa cgaactaata ctgtagccct    2280
agacttgata gccatcatca tatcgaagtt tcactaccct ttttccattt gccatctatt    2340
gaagtaataa taggcgcatg caacttcttt tctttttttt tcttttctct ctccccgtt    2400 gttgtctcac catatccgca atgacaaaaa aatgatggaa gacactaaag gaaaaaatta    2460
acgacaaaga cagcaccaac agatgtcgtt gttccagagc tgatgggggg tatctcgaag    2520
cacacgaaac ttttccttc cttcattcac gcacactact ctctaatgag caacggtata    2580
cggccttcct tccagttact tgaatttgaa ataaaaaaag tttgctgtct tgctatcaag    2640
tataaataga cctgcaatta ttaatctttt gtttcctcgt cattgttctc gttccctttc    2700
ttccttgttt cttttttctgc acaatatttc aagctatacc aagcatacaa tcaactatct    2760
catatacaat gagattccca tctatcttca ctgccgtctt gttcgctgct tcttctgctt    2820
tagctgttcc agttgaattg gataagagaa acaccggtca tttccaagct tattctggtt    2880
ataccgttgc tagatctaac ttcacccaat ggattcatga caaccagct gtttcttggt    2940 actacttgtt gcaaaacatc gattacccag aaggtcaatt caaatctgct aaaccaggtg    3000
ttgttgttgc ttctccatct acatctgaac cagattactt ctaccaatgg actagagata    3060
ccgctattac cttcttgtcc ttgattgctg aagttgaaga tcattcttc tccaacacta    3120 ccttggctaa ggttgtcgaa tattacattt ccaacaccta caccttgcaa agagtttcta    3180
atccatccgg taacttcgat tctccaaatc atgatggttt gggtgaacct aagttcaacg    3240
ttgatgatac tgcttataca gcttcttggg gtagaccaca aaatgatggt ccagctttga    3300
gagcttacgc tatttctaga tacttgaacg ctgttgctaa gcacaacaac ggtaaattat    3360
tattggccgg tcaaaacggt attccttatt cttctgcttc cgatatctac tggaagatta    3420
ttaagccaga cttgcaacat gtttctactc attggtctac ctctggtttt gatttgtggg    3480
aagaaaatca aggtactcat ttcttcaccg cttttggttca attgaaggct ttgtcttacg    3540
gtattccatt gtctaagacc tacaatgatc caggtttcac ttcttggttg gaaaaacaaa    3600
aggatgcctt gaactcctac attaactctt ccggtttcgt taactctggt aaaaagcaca    3660
tcgttgaatc tccacaattg tcatctagag gtggtttgga ttctgctact tatattgctg    3720
ccttgatcac ccatgatatc ggtgatgatg atacttacac cccattcaat gttgataact    3780
cctacgtttt gaactccttg tattacctat tggtcgacaa caagaacaga tacaagatca    3840
acggtaacta caaagctggt gctgctgttg gtagatatcc tgaagatgtt tacaacggtg    3900
ttggtacttc tgaaggtaat ccatggcaat tggctactgc ttatgctggt caaactttt    3960 acaccttggc ctacaattcc ttgaagaaca agaagaactt ggtcatcgaa aagttgaact    4020
acgacttgta caactccttc attgctgatt tgtccaagat tgattcttcc tacgcttcta    4080
aggattcttt gactttgacc tacggttccg ataactacaa gaacgttatc aagtccttgt    4140
tgcaattcgg tgactcattc ttgaaggttt tgttggatca catcgatgac aacggtcaat    4200
tgactgaaga aatcaacaga tacaccggtt ttcaagctgg tgcagttcct ttgacttggt    4260
catctggttc tttgttgtct gctaatagag ccagaaacaa gttgatcgaa ttattgtaaa    4320
caggccccct ttcctttgtc gatatcatgt aattagttat gtcacgctta cattcacgcc    4380
ctcctcccac atccgctcta accgaaaagg aaggagttag acaacctgaa gtctaggtcc    4440
```

```
ctatttatttt ttttatagtt atgttagtat taagaacgtt atttatattt caaattttc      4500 ttttttttct gtacaaacgc gtgtacgcat gtaacgggca gacgaattcg atatcaagct      4560
tatcgatacc gtcgacctcg agggggggcc cggtaccagc ttttgttccc tttagtgagg      4620
gttaattccg agcttggcgt aatcatggtc atagctgttt cctgtgtgaa attgttatcc      4680
gctcacaatt ccacacaaca taggagccgg aagcataaag tgtaaagcct ggggtgccta      4740
atgagtgagg taactcacat taattgcgtt gcgctcactg cccgctttcc agtcgggaaa      4800
cctgtcgtgc cagctgcatt aatgaatcgg ccaacgcgcg gggagaggcg gtttgcgtat      4860
tgggcgctct tccgcttcct cgctcactga ctcgctgcgc tcggtcgttc ggctgcggcg      4920
agcggtatca gctcactcaa aggcggtaat acggttatcc acagaatcag gggataacgc      4980
aggaaagaac atgtgagcaa aaggccagca aaaggccagg aaccgtaaaa aggccgcgtt      5040
gctggcgttt ttccataggc tcggcccccc tgacgagcat cacaaaaatc gacgctcaag      5100
tcagaggtgg cgaaacccga caggactata aagataccag gcgttccccc tggaagctc       5160 cctcgtgcgc tctcctgttc cgaccctgcc gcttaccgga tacctgtccg cctttctccc      5220
ttcgggaagc gtggcgcttt ctcaatgctc acgctgtagg tatctcagtt cggtgtaggt      5280
cgttcgctcc aagctgggct gtgtgcacga accccccgtt cagcccgacc gctgcgcctt      5340
atccggtaac tatcgtcttg agtccaaccc ggtaagacac gacttatcgc cactggcagc      5400
agccactggt aacaggatta gcagagcgag gtatgtaggc ggtgctacag agttcttgaa      5460
gtggtggcct aactacggct acactagaag gacagtattt ggtatctgcg ctctgctgaa      5520
gccagttacc ttcggaaaaa gagttggtag ctcttgatcc ggcaaacaaa ccaccgctgg      5580
tagcggtggt ttttttgttt gcaagcagca gattacgcgc agaaaaaaag gatctcaaga      5640
agatcctttg atcttttcta cggggtctga cgctcagtgg aacgaaaact cacgttaagg      5700
gattttggtc atgagattat caaaaaggat cttcacctag atccttttaa attaaaaatg      5760
aagttttaaa tcaatctaaa gtatatatga gtaaacttgg tctgacagtt accaatgctt      5820
aatcagtgag gcacctatct cagcgatctg tctatttcgt tcatccatag ttgcctgact      5880
gcccgtcgtg tagataacta cgatacggga gggcttacca tctggcccca gtgctgcaat      5940
gataccgcga gacccacgct caccggctcc agatttatca gcaataaacc agccagccgg      6000
aagggccgag cgcagaagtg gtcctgcaac tttatccgcc tccatccagt ctattaattg      6060
ttgccgggaa gctagagtaa gtagttcgcc agttaatagt ttgcgcaacg ttgttgccat      6120
tgctacaggc atcgtggtgt cacgctcgtc gtttggtatg gcttcattca gctccggttc      6180
ccaacgatca aggcgagtta catgatcccc catgttgtga aaaaaagcgg ttagctcctt      6240
cggtcctccg atcgttgtca gaagtaagtt ggccgcagtg ttatcactca tggttatggc      6300
agcactgcat aattctctta ctgtcatgcc atccgtaaga tgcttttctg tgactggtga      6360
gtactcaacc aagtcattct gagaatagtg tatgcggcga ccgagttgct cttgcccggc      6420
gtcaatacgg gataataccg cgccacatag cagaacttta aaagtgctca tcattggaaa      6480
acgttcttcg gggcgaaaac tctcaaggat cttaccgctg ttgagatcca gttcgatgta      6540
acccactcgt gcacccaact gatcttcagc atcttttact ttcaccagcg tttctgggtg      6600
agcaaaaaca ggaaggcaaa atgccgcaaa aaagggaata agggcgacac ggaaatgttg      6660
aatactcata ctcttccttt ttcaatatta ttgaagcatt tatcagggtt attgtctcat      6720
gagcggatac atatttgaat gtatttagaa aaataaacaa ataggggttc cgcgcacatt      6780
tccccgaaaa gtgccacctg gtcctttttc atcacgtgct ataaaaataa ttataattta      6840
```

```
aattttttaa tataaatata taaattaaaa atagaaagta aaaaaagaaa ttaaagaaaa    6900
aatagttttt gttttccgaa gatgtaaaag actctagggg gatcgccaac aaatactacc    6960
ttttatcttg ctcttcctgc tctcaggtat taatgccgaa ttgtttcatc ttgtctgtgt    7020
agaagaccac acacgaaaat cctgtgattt tacattttac ttatcgttaa tcgaatgtat    7080
atctatttaa tctgcttttc ttgtctaata aatatatatg taaagtacgc tttttgttga    7140
aattttttaa acctttgttt attttttttt cttcattccg taactcttct accttcttta    7200
tttactttct aaaatccaaa tacaaaacat aaaaataaat aaacacagag taaattccca    7260
aattattcca tcattaaaag atacgaggcg cgtgtaagtt acaggcaagc gatccgtcct    7320
aagaaaccat tattatcatg acattaacct ataaaatag gcgtatcacg aggcccttt     7380
gtc                                                                 7383
```

<210> SEQ ID NO 7
<211> LENGTH: 7383
<212> TYPE: DNA
<213> ORGANISM: Artificial Sequence
<220> FEATURE:
<223> OTHER INFORMATION: pAV34

<400> SEQUENCE: 7

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accacgcttt tcaattcaat tcatcatttt tttttttattc tttttttttga tttcggtttc    240
tttgaaattt ttttgattcg gtaatctccg aacagaagga agaacgaagg aaggagcaca    300
gacttagatt ggtatatata cgcatatgta gtgttgaaga acatgaaat tgcccagtat     360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg    1020
tgggtttaga tgacaaggga gacgcattgg gtcaacagta tagaaccgtg gatgatgtgg    1080
tctctacagg atctgacatt attattgttg gaagaggact atttgcaaag ggaagggatg    1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta acgttaata ttttgttaaa attcgcgtta     1380
aattttttgtt aaatcagctc attttttaac caataggccg aaatcggcaa aatcccttat    1440
```

-continued

```
aaatcaaaag aatagaccga gatagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttggggt cgaggtgccg taaagcacta    1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa gggggatgt gctgcaaggc gattaagttg ggtaacgcca    1920
gggttttccc agtcacgacg ttgtaaaacg acggccagtg aattgtaata cgactcacta    1980
tagggcgaat ggagctcca ccgcggtggc ggccgcctcg agatctcccc taaaccgtgg    2040
aatatttcgg atatccttt gttgtttccg ggtgtacaat atggacttcc tcttttctgg    2100
caaccaaacc catacatcgg gattcctata ataccttcgt tggtctccct aacatgtagg    2160
tggcggaggg gagatataca atagaacaga taccagacaa gacataatgg gctaaacaag    2220
actacaccaa ttacactgcc tcattgatgg tggtacataa cgaactaata ctgtagccct    2280
agacttgata gccatcatca tatcgaagtt tcactaccct ttttccattt gccatctatt    2340
gaagtaataa taggcgcatg caacttcttt tcttttttt tcttttctct ctccccgtt     2400 gttgtctcac catatccgca atgacaaaaa aatgatggaa gacactaaag gaaaaaatta    2460
acgacaaaga cagcaccaac agatgtcgtt gttccagagc tgatgggggg tatctcgaag    2520
cacacgaaac ttttccttc cttcattcac gcacactact ctctaatgag caacggtata    2580
cggccttcct tccagttact tgaatttgaa ataaaaaag tttgctgtct tgctatcaag    2640
tataaataga cctgcaatta ttaatctttt gtttcctcgt cattgttctc gttccctttc    2700
ttccttgttt ctttttctgc acaatattc aagctatacc aagcatacaa tcaactatct    2760
catatacaat gaagttcatt tccactttct tgaccttcat tttggctgct gtctctgtca    2820
ccgctgttcc agttgaattg gataagagaa acaccggtca tttccaagct tattctggtt    2880
ataccgttgc tagatctaac ttcacccaat ggattcatga caaccagct gtttcttggt     2940 actacttgtt gcaaaacatc gattacccag aaggtcaatt caaatctgct aaaccaggtg    3000
ttgttgttgc ttctccatct acatctgaac cagattactt ctaccaatgg actagagata    3060
ccgctattac cttcttgtcc ttgattgctg aagttgaaga tcattctttc tccaacacta    3120
ccttggctaa ggttgtcgaa tattacattt ccaacaccta caccttgcaa agagtttcta    3180
atccatccgg taacttcgat tctccaaatc atgatggttt gggtgaacct aagttcaacg    3240
ttgatgatac tgcttataca gcttcttggg gtagaccaca aaatgatggt ccagctttga    3300
gagcttacgc tatttctaga tacttgaacg ctgttgctaa gcacaacaac ggtaaattat    3360
tattggccgg tcaaaacggt attccttatt cttctgcttc cgatatctac tggaagatta    3420
ttaagccaga cttgcaacat gtttctactc attggtctac ctctggtttt gatttgtggg    3480
aagaaaatca aggtactcat ttcttcaccg ctttggttca attgaaggct ttgtcttacg    3540
gtattccatt gtctaagacc tacaatgatc caggtttcac ttcttggttg gaaaaacaaa    3600
aggatgcctt gaactcctac attaactctt ccggtttcgt taactctggt aaaaagcaca    3660
tcgttgaatc tccacaattg tcatctagag gtggtttgga ttctgctact tatattgctg    3720
ccttgatcac ccatgatatc ggtgatgatg ataatcttacac cccattcaat gttgataact    3780
cctacgtttt gaactccttg tattacctat tggtcgacaa caagaacaga tacaagatca    3840
```

```
acggtaacta caaagctggt gctgctgttg gtagatatcc tgaagatgtt tacaacggtg    3900
ttggtacttc tgaaggtaat ccatggcaat tggctactgc ttatgctggt caaacttttt    3960
acaccttggc ctacaattcc ttgaagaaca agaagaactt ggtcatcgaa aagttgaact    4020
acgacttgta caactccttc attgctgatt tgtccaagat tgattcttcc tacgcttcta    4080
aggattcttt gactttgacc tacggttccg ataactacaa gaacgttatc aagtccttgt    4140
tgcaattcgg tgactcattc ttgaaggttt tgttggatca catcgatgac aacggtcaat    4200
tgactgaaga aatcaacaga tacaccggtt tcaagctggt gcagtttct ttgacttggt    4260 catctggttc tttgttgtct gctaatagag ccagaaacaa gttgatcgaa ttattgtaaa    4320
caggccccct tttcctttgtc gatatcatgt aattagttat gtcacgctta cattcacgcc    4380
ctcctcccac atccgctcta accgaaaagg aaggagttag acaacctgaa gtctaggtcc    4440
ctatttattt ttttatagtt atgttagtat taagaacgtt atttatattt caaattttc    4500 ttttttttct gtacaaacgc gtgtacgcat gtaacgggca gacgaattcg atatcaagct    4560
tatcgatacc gtcgacctcg agggggggcc cggtaccagc ttttgttccc tttagtgagg    4620
gttaattccg agcttggcgt aatcatggtc atagctgttt cctgtgtgaa attgttatcc    4680
gctcacaatt ccacacaaca taggagccgg aagcataaag tgtaaagcct ggggtgccta    4740
atgagtgagg taactcacat taattgcgtt gcgctcactg cccgctttcc agtcgggaaa    4800
cctgtcgtgc cagctgcatt aatgaatcgg ccaacgcgcg gggagaggcg gtttgcgtat    4860
tgggcgctct tccgcttcct cgctcactga ctcgctgcgc tcggtcgttc ggctgcggcg    4920
agcggtatca gctcactcaa aggcggtaat acggttatcc acagaatcag gggataacgc    4980
aggaaagaac atgtgagcaa aaggccagca aaaggccagg aaccgtaaaa aggccgcgtt    5040
gctggcgttt ttccataggc tccgcccccc tgacgagcat cacaaaaatc gacgctcaag    5100
tcagaggtgg cgaaacccga caggactata aagataccag gcgttccccc ctggaagctc    5160
cctcgtgcgc tctcctgttc cgaccctgcc gcttaccgga tacctgtccg cctttctccc    5220
ttcgggaagc gtggcgcttt ctcaatgctc acgctgtagg tatctcagtt cggtgtaggt    5280
cgttcgctcc aagctgggct gtgtgcacga acccccgtt cagcccgacc gctgcgcctt    5340
atccggtaac tatcgtcttg agtccaaccc ggtaagacac gacttatcgc cactggcagc    5400
agccactggt aacaggatta gcagagcgag gtatgtaggc ggtgctacag agttcttgaa    5460
gtggtggcct aactacggct acactagaag gacagtattt ggtatctgcg ctctgctgaa    5520
gccagttacc ttcggaaaaa gagttggtag ctcttgatcc ggcaaacaaa ccaccgctgg    5580
tagcggtggt ttttttgttt gcaagcagca gattacgcgc agaaaaaaag gatctcaaga    5640
agatcctttg atcttttcta cggggtctga cgctcagtgg aacgaaaact cacgttaagg    5700
gattttggtc atgagattat caaaaaggat cttcacctag atccttttaa attaaaaatg    5760
aagttttaaa tcaatctaaa gtatatatga gtaaacttgg tctgacagtt accaatgctt    5820
aatcagtgag gcacctatct cagcgatctg tctatttcgt tcatccatag ttgcctgact    5880
gcccgtcgtg tagataacta cgatacggga gggcttacca tctggcccca gtgctgcaat    5940
gataccgcga gacccacgct caccggctcc agatttatca gcaataaacc agccagccgg    6000
aagggccgag cgcagaagtg gtcctgcaac tttatccgcc tccatccagt ctattaattg    6060
ttgccgggaa gctagagtaa gtagttcgcc agttaatagt ttgcgcaacg ttgttgccat    6120
tgctacaggc atcgtggtgt cacgctcgtc gtttggtatg gcttcattca gctccggttc    6180
```

```
ccaacgatca aggcgagtta catgatcccc catgttgtga aaaaaagcgg ttagctcctt    6240
cggtcctccg atcgttgtca gaagtaagtt ggccgcagtg ttatcactca tggttatggc    6300
agcactgcat aattctctta ctgtcatgcc atccgtaaga tgcttttctg tgactggtga    6360
gtactcaacc aagtcattct gagaatagtg tatgcggcga ccgagttgct cttgcccggc    6420
gtcaatacgg gataataccg cgccacatag cagaacttta aaagtgctca tcattggaaa    6480
acgttcttcg gggcgaaaac tctcaaggat cttaccgctg ttgagatcca gttcgatgta    6540
acccactcgt gcacccaact gatcttcagc atcttttact ttcaccagcg tttctgggtg    6600
agcaaaaaca ggaaggcaaa atgccgcaaa aaagggaata agggcgacac ggaaatgttg    6660
aatactcata ctcttccttt tcaatatta ttgaagcatt tatcagggtt attgtctcat    6720
gagcggatac atatttgaat gtatttagaa aaataaacaa ataggggttc cgcgcacatt    6780
tccccgaaaa gtgccacctg ggtccttttc atcacgtgct ataaaaataa ttataattta    6840
aattttttaa tataaatata taaattaaaa atagaaagta aaaaaagaaa ttaagaaaaa    6900
aatagttttt gttttccgaa gatgtaaaag actctagggg gatcgccaac aaatactacc    6960
ttttatcttg ctcttcctgc tctcaggtat taatgccgaa ttgtttcatc ttgtctgtgt    7020
agaagaccac acacgaaaat cctgtgattt tacatttac ttatcgttaa tcgaatgtat    7080
atctatttaa tctgcttttc ttgtctaata aatatatatg taaagtacgc ttttgttga    7140
aattttttaa acctttgttt atttttttttt cttcattccg taactcttct accttcttta    7200
tttactttct aaaatccaaa tacaaaacat aaaaataaat aaacacagag taaattccca    7260
aattattcca tcattaaaag atacgaggcg cgtgtaagtt acaggcaagc gatccgtcct    7320
aagaaaccat tattatcatg acattaacct ataaaaatag gcgtatcacg aggcccttttc    7380
gtc                                                                  7383

<210> SEQ ID NO 8
<211> LENGTH: 7377
<212> TYPE: DNA
<213> ORGANISM: Artificial Sequence
<220> FEATURE:
<223> OTHER INFORMATION: pTAN35

<400> SEQUENCE: 8
tcgcgcgttt cggtgatgac ggtgaaaacc tctgacacat gcagctcccg gagacggtca     60
cagcttgtct gtaagcggat gccggagcaa gacaagcccg tcagggcgcg tcagcgggtg    120
ttggcgggtg tcggggctgg cttaactatg cggcatcaga gcagattgta ctgagagtgc    180
accacgcttt tcaattcaat tcatcatttt ttttttattc tttttttga tttcggtttc    240
tttgaaattt ttttgattcg gtaatctccg aacagaagga agaacgaagg aaggagcaca    300
gacttagatt ggtatatata cgcatatgta gtgttgaaga acatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
```

```
ctagaggcct tttgatgtta gcagaattgt catgcaaggg ctccctatct actggagaat      900
atactaaggg tactgttgac attgcgaaga gcgacaaaga ttttgttatc ggctttattg      960
ctcaaagaga catgggtgga agagatgaag gttacgattg gttgattatg cacccggtg      1020
tgggtttaga tgacaaggga gacgcattgg gtcaacagta tagaaccgtg gatgatgtgg     1080
tctctacagg atctgacatt attattgttg gaagaggact atttgcaaag ggaagggatg     1140
ctaaggtaga gggtgaacgt tacagaaaag caggctggga agcatatttg agaagatgcg     1200
gccagcaaaa ctaaaaaact gtattataag taaatgcatg tatactaaac tcacaaatta     1260
gagcttcaat ttaattatat cagttattac cctgcggtgt gaaataccgc acagatgcgt     1320
aaggagaaaa taccgcatca ggaaattgta acgttaata ttttgttaaa attcgcgtta     1380
aatttttgtt aaatcagctc attttttaac caataggccg aaatcggcaa aatcccttat     1440
aaatcaaaag aatagaccga datagggttg agtgttgttc cagtttggaa caagagtcca     1500
ctattaaaga acgtggactc caacgtcaaa gggcgaaaaa ccgtctatca gggcgatggc     1560
ccactacgtg aaccatcacc ctaatcaagt tttttgggt cgaggtgccg taaagcacta     1620
aatcggaacc ctaaagggag ccccgatt agagcttgac ggggaaagcc ggcgaacgtg     1680
gcgagaaagg aagggaagaa agcgaaagga gcgggcgcta gggcgctggc aagtgtagcg     1740
gtcacgctgc gcgtaaccac cacacccgcc gcgcttaatg cgccgctaca gggcgcgtcg     1800
cgccattcgc cattcaggct gcgcaactgt tgggaagggc gatcggtgcg ggcctcttcg     1860
ctattacgcc agctggcgaa ggggggatgt gctgcaaggc gattaagttg ggtaacgcca     1920
gggttttccc agtcacgacg ttgtaaaacg acggccagtg aattgtaata cgactcacta     1980
tagggcgaat tggagctcca ccgcggtggc ggccgcctcg agatctcccc taaaccgtgg     2040
aatatttcgg atatcctttt gttgtttccg ggtgtacaat atggacttcc tcttttctgg     2100
caaccaaacc catacatcgg gattcctata ataccttcgt tggtctccct aacatgtagg     2160
tggcggaggg gagatataca atagaacaga taccagacaa gacataatgg gctaaacaag     2220
actacaccaa ttacactgcc tcattgatgg tggtacataa cgaactaata ctgtagccct     2280
agacttgata gccatcatca tatcgaagtt tcactaccct ttttccattt gccatctatt     2340
gaagtaataa taggcgcatg caacttcttt tctttttttt tcttttctct ctccccgtt      2400
gttgtctcac catatccgca atgacaaaaa aatgatggaa gacactaaag gaaaaaatta     2460
acgacaaaga cagcaccaac agatgtcgtt gttccagagc tgatgggggg tatctcgaag     2520
cacacgaaac ttttccttc cttcattcac gcacactact ctctaatgag caacggtata     2580
cggccttcct tccagttact tgaatttgaa ataaaaaaag tttgctgtct tgctatcaag     2640
tataaataga cctgcaatta ttaatctttt gtttcctcgt cattgttctc gttccctttc     2700
ttccttgttt ctttttctgc acaatatttc aagctatacc aagcatacaa tcaactatct     2760
catatacaat gttcaagtct gttgtttact ctatttggc tgcctctttg gctaacgctg      2820
ttccagttga attggataag agaaacaccg gtcatttcca agcttattct ggttataccg     2880
ttgctagatc taacttcacc caatggattc atgaacaacc agctgtttct tggtactact     2940
tgttgcaaaa catcgattac ccagaaggtc aattcaaatc tgctaaacca ggtgttgttg     3000
ttgcttctcc atctacatct gaaccagatt acttctacca atggactaga gataccgcta     3060
ttaccttctt gtccttgatt gctgaagttg aagatcattc tttctccaac actaccttgg     3120
ctaaggttgt cgaatattac atttccaaca cctacacctt gcaaagagtt tctaatccat     3180
```

```
ccggtaactt cgattctcca aatcatgatg gtttgggtga acctaagttc aacgttgatg   3240
atactgctta tacagcttct tggggtagac cacaaaatga tggtccagct ttgagagctt   3300
acgctatttc tagatacttg aacgctgttg ctaagcacaa caacggtaaa ttattattgg   3360
ccggtcaaaa cggtattcct tattcttctg cttccgatat ctactggaag attattaagc   3420
cagacttgca acatgtttct actcattggt ctacctctgg ttttgatttg tgggaagaaa   3480
atcaaggtac tcatttcttc accgctttgg ttcaattgaa ggctttgtct tacggtattc   3540
cattgtctaa gacctacaat gatccaggtt tcacttcttg gttggaaaaa caaaaggatg   3600
ccttgaactc ctacattaac tcttccggtt tcgttaactc tggtaaaaag cacatcgttg   3660
aatctccaca attgtcatct agaggtggtt tggattctgc tacttatatt gctgccttga   3720
tcacccatga tatcggtgat gatgatactt acaccccatt caatgttgat aactcctacg   3780
ttttgaactc cttgtattac ctattggtcg acaacaagaa cagatacaag atcaacggta   3840
actacaaagc tggtgctgct gttggtagat atcctgaaga tgtttacaac ggtgttggta   3900
cttctgaagg taatccatgg caattggcta ctgcttatgc tggtcaaact ttttacacct   3960
tggcctacaa ttccttgaag aacaagaaga acttggtcat cgaaaagttg aactacgact   4020
tgtacaactc cttcattgct gatttgtcca agattgattc ttcctacgct tctaaggatt   4080
ctttgacttt gacctacggt tccgataact acaagaacgt tatcaagtcc ttgttgcaat   4140
tcggtgactc attcttgaag gttttgttgg atcacatcga tgcaacggt caattgactg   4200 aagaaatcaa cagatacacc ggttttcaag ctggtgcagt ttctttgact tggtcatctg   4260
gttctttgtt gtctgctaat agagccagaa acaagttgat cgaattattg taaacaggcc   4320
ccttttcctt tgtcgatatc atgtaattag ttatgtcacg cttacattca cgccctcctc   4380
ccacatccgc tctaaccgaa aaggaaggag ttagacaacc tgaagtctag gtccctatt   4440 atttttttat agttatgtta gtattaagaa cgttatttat atttcaaatt tttctttttt   4500
ttctgtacaa acgcgtgtac gcatgtaacg ggcagacgaa ttcgatatca agcttatcga   4560
taccgtcgac ctcgaggggg ggcccggtac cagcttttgt tccctttagt gagggttaat   4620
tccgagcttg gcgtaatcat ggtcatagct gtttcctgtg tgaaattgtt atccgctcac   4680
aattccacac aacataggag ccggaagcat aaagtgtaaa gcctggggtg cctaatgagt   4740
gaggtaactc acattaattg cgttgcgctc actgcccgct ttccagtcgg gaaacctgtc   4800
gtgccagctg cattaatgaa tcggccaacg cgcggggaga ggcggtttgc gtattgggcg   4860
ctcttccgct tcctcgctca ctgactcgct gcgctcggtc gttcggctgc ggcgagcggt   4920
atcagctcac tcaaaggcgg taatacggtt atccacagaa tcaggggata acgcaggaaa   4980
gaacatgtga gcaaaaggcc agcaaaaggc caggaaccgt aaaaaggccg cgttgctggc   5040 gttttccat aggctcggcc cccctgacga gcatcacaaa aatcgacgct caagtcagag   5100
gtggcgaaac ccgacaggac tataaagata ccaggcgttc ccccctggaa gctccctcgt   5160
gcgctctcct gttccgaccc tgccgcttac cggatacctg tccgcctttc tcccttcggg   5220
aagcgtggcg ctttctcaat gctcacgctg taggtatctc agttcggtgt aggtcgttcg   5280
ctccaagctg ggctgtgtgc acgaaccccc cgttcagccc gaccgctgcg ccttatccgg   5340
taactatcgt cttgagtcca acccggtaag acacgactta tcgccactgg cagcagccac   5400
tggtaacagg attagcagag cgaggtatgt aggcggtgct acagagttct tgaagtggtg   5460
gcctaactac ggctacacta aaggacagt atttggtatc tgcgctctgc tgaagccagt   5520
taccttcgga aaaagagttg gtagctcttg atccggcaaa caaaccaccg ctggtagcgg   5580
```

```
tggttttttt gtttgcaagc agcagattac gcgcagaaaa aaaggatctc aagaagatcc    5640
tttgatcttt tctacggggt ctgacgctca gtggaacgaa aactcacgtt aagggatttt    5700
ggtcatgaga ttatcaaaaa ggatcttcac ctagatcctt ttaaattaaa aatgaagttt    5760
taaatcaatc taaagtatat atgagtaaac ttggtctgac agttaccaat gcttaatcag    5820
tgaggcacct atctcagcga tctgtctatt tcgttcatcc atagttgcct gactgcccgt    5880
cgtgtagata actacgatac gggagggctt accatctggc cccagtgctg caatgatacc    5940
gcgagaccca cgctcaccgg ctccagattt atcagcaata aaccagccag ccggaagggc    6000
cgagcgcaga agtggtcctg caactttatc cgcctccatc cagtctatta attgttgccg    6060
ggaagctaga gtaagtagtt cgccagttaa tagtttgcgc aacgttgttg ccattgctac    6120
aggcatcgtg gtgtcacgct cgtcgtttgg tatggcttca ttcagctccg gttcccaacg    6180
atcaaggcga gttacatgat cccccatgtt gtgaaaaaaa gcggttagct ccttcggtcc    6240
tccgatcgtt gtcagaagta agttggccgc agtgttatca ctcatggtta tggcagcact    6300
gcataattct cttactgtca tgccatccgt aagatgcttt tctgtgactg gtgagtactc    6360
aaccaagtca ttctgagaat agtgtatgcg gcgaccgagt tgctcttgcc cggcgtcaat    6420
acgggataat accgcgccac atagcagaac tttaaaagtg ctcatcattg gaaaacgttc    6480
ttcggggcga aaactctcaa ggatcttacc gctgttgaga tccagttcga tgtaacccac    6540
tcgtgcaccc aactgatctt cagcatcttt tactttcacc agcgtttctg ggtgagcaaa    6600
aacaggaagg caaaatgccg caaaaaaggg aataagggcg acacggaaat gttgaatact    6660
catactcttc ctttttcaat attattgaag catttatcag ggttattgtc tcatgagcgg    6720
atacatattt gaatgtattt agaaaaataa acaaataggg gttccgcgca catttccccg    6780
aaaagtgcca cctgggtcct tttcatcacg tgctataaaa ataattataa tttaaatttt    6840
ttaatataaa tatataaatt aaaaatagaa agtaaaaaa gaaattaaag aaaaaatagt    6900
ttttgttttc cgaagatgta aaagactcta gggggatcgc caacaaatac tacctttat    6960 cttgctcttc ctgctctcag gtattaatgc cgaattgttt catcttgtct gtgtagaaga    7020
ccacacacga aaatcctgtg atttttacatt ttacttatcg ttaatcgaat gtatatctat    7080
ttaatctgct tttcttgtct aataaatata tatgtaaagt acgcttttg ttgaaatttt    7140 ttaaaccttt gttatttttt ttttcttcat tccgtaactc ttctaccttc tttatttact    7200
ttctaaaatc caaatacaaa acataaaaat aaataaacac agagtaaatt cccaaattat    7260
tccatcatta aaagatacga ggcgcgtgta agttacaggc aagcgatccg tcctaagaaa    7320
ccattattat catgacatta acctataaaa ataggcgtat cacgaggccc tttcgtc      7377
```

<210> SEQ ID NO 9
<211> LENGTH: 4887
<212> TYPE: DNA
<213> ORGANISM: Artificial Sequence
<220> FEATURE:
<223> OTHER INFORMATION: pRS316

<400> SEQUENCE: 9

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc ttttttttga tttcggtttc     240
```

```
tttgaaatttt ttttgattcg gtaatctccg aacagaagga agaacgaagg aaggagcaca    300
gacttagatt ggtatatata cgcatatgta gtgttgaaga aacatgaaat tgcccagtat    360
tcttaacccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttttccatg gagggcacag ttaagccgct aaaggcatta tccgccaagt    660
acaattttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta   1380
aattttttgtt aaatcagctc attttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt ttttgggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcca ccgcggtggc ggccgctcta gaactagtgg atcccccggg   2040
ctgcaggaat tcgatatcaa gcttatcgat accgtcgacc tcgaggggg gcccggtacc   2100
cagcttttgt tccctttagt gagggttaat tccgagcttg gcgtaatcat ggtcatagct   2160
gtttcctgtg tgaaattgtt atccgctcac aattccacac aacataggag ccggaagcat   2220
aaagtgtaaa gcctggggtg cctaatgagt gaggtaactc acattaattg cgttgcgctc   2280
actgcccgct ttccagtcgg gaaacctgtc gtgccagctg cattaatgaa tcggccaacg   2340
cgcggggaga ggcggtttgc gtattgggcg ctcttccgct tcctcgctca ctgactcgct   2400
gcgctcggtc gttcggctgc ggcgagcggt atcagctcac tcaaaggcgg taatacggtt   2460
atccacagaa tcaggggata acgcaggaaa gaacatgtga gcaaaaggcc agcaaaaggc   2520
caggaaccgt aaaaaggccg cgttgctggc gttttttccat aggctcggcc ccctgacga   2580
gcatcacaaa aatcgacgct caagtcagag gtggcgaaac ccgacaggac tataaagata   2640
```

```
ccaggcgttc cccctggaa gctccctcgt gcgctctcct gttccgaccc tgccgcttac    2700
cggatacctg tccgcctttc tcccttcggg aagcgtggcg ctttctcaat gctcacgctg    2760
taggtatctc agttcggtgt aggtcgttcg ctccaagctg ggctgtgtgc acgaaccccc    2820
cgttcagccc gaccgctgcg ccttatccgg taactatcgt cttgagtcca acccggtaag    2880
acacgactta tcgccactgg cagcagccac tggtaacagg attagcagag cgaggtatgt    2940
aggcggtgct acagagttct tgaagtggtg gcctaactac ggctacacta agggacagt    3000 atttggtatc tgcgctctgc tgaagccagt taccttcgga aaaagagttg gtagctcttg    3060
atccggcaaa caaccaccg ctggtagcgg tggttttttt gtttgcaagc agcagattac    3120
gcgcagaaaa aaaggatctc aagaagatcc tttgatcttt tctacggggt ctgacgctca    3180
gtggaacgaa aactcacgtt aagggatttt ggtcatgaga ttatcaaaaa ggatcttcac    3240
ctagatcctt ttaaattaaa aatgaagttt taaatcaatc taaagtatat atgagtaaac    3300
ttggtctgac agttaccaat gcttaatcag tgaggcacct atctcagcga tctgtctatt    3360
tcgttcatcc atagttgcct gactgcccgt cgtgtagata actacgatac gggagggctt    3420
accatctggc cccagtgctg caatgatacc gcgagaccca cgctcaccgg ctccagattt    3480
atcagcaata accagccag ccggaagggc cgagcgcaga agtggtcctg caactttatc    3540
cgcctccatc cagtctatta attgttgccg ggaagctaga gtaagtagtt cgccagttaa    3600
tagtttgcgc aacgttgttg ccattgctac aggcatcgtg gtgtcacgct cgtcgtttgg    3660
tatggcttca ttcagctccg gttcccaacg atcaaggcga gttacatgat cccccatgtt    3720
gtgaaaaaaa gcggttagct ccttcggtcc tccgatcgtt gtcagaagta agttggccgc    3780
agtgttatca ctcatggtta tggcagcact gcataattct cttactgtca tgccatccgt    3840
aagatgcttt tctgtgactg gtgagtactc aaccaagtca ttctgagaat agtgtatgcg    3900
gcgaccgagt tgctcttgcc cggcgtcaat acgggataat accgcgccac atagcagaac    3960
tttaaaagtg ctcatcattg gaaaacgttc ttcggggcga aaactctcaa ggatcttacc    4020
gctgttgaga tccagttcga tgtaacccac tcgtgcaccc aactgatctt cagcatcttt    4080
tactttcacc agcgtttctg ggtgagcaaa aacaggaagg caaaatgccg caaaaagggg    4140 ataagggcg acacggaaat gttgaatact catactcttc ctttttcaat attattgaag    4200
catttatcag ggttattgtc tcatgagcgg atacatattt gaatgtattt agaaaaataa    4260
acaaataggg gttccgcgca catttccccg aaaagtgcca cctgggtcct tttcatcacg    4320
tgctataaaa ataattataa tttaaatttt taatatataa tatataaatt aaaaatagaa    4380
agtaaaaaaa gaaattaaag aaaaaatagt ttttgttttc cgaagatgta aaagactcta    4440
gggggatcgc caacaaatac tacctttat cttgctcttc ctgctctcag gtattaatgc    4500
cgaattgttt catcttgtct gtgtagaaga ccacacacga aaatcctgtg attttacatt    4560
ttacttatcg ttaatcgaat gtatatctat ttaatctgct tttcttgtct aataaatata    4620
tatgtaaagt acgcttttg ttgaaatttt ttaaacctttt gtttattttt ttttcttcat    4680
tccgtaactc ttctaccttc tttatttact ttctaaaatc caaatacaaa acataaaaat    4740
aaataaacac agagtaaatt cccaaattat tccatcatta aaagatacga ggcgcgtgta    4800
agttacaggc aagcgatccg tcctaagaaa ccattattat catgacatta acctataaaa    4860
ataggcgtat cacgaggccc tttcgtc                                         4887
```

<210> SEQ ID NO 10

```
<211> LENGTH: 19
<212> TYPE: PRT
<213> ORGANISM: Artificial Sequence
<220> FEATURE:
<223> OTHER INFORMATION: MFalpha2 signal sequence

<400> SEQUENCE: 10

Met Lys Phe Ile Ser Thr Phe Leu Thr Phe Ile Leu Ala Ala Val Ser
1               5                   10                  15

Val Thr Ala

<210> SEQ ID NO 11
<211> LENGTH: 16
<212> TYPE: PRT
<213> ORGANISM: Artificial Sequence
<220> FEATURE:
<223> OTHER INFORMATION: PHO5 signal sequence

<400> SEQUENCE: 11

Met Phe Lys Ser Val Val Tyr Ser Ile Leu Ala Ala Ser Leu Ala Asn
1               5                   10                  15

<210> SEQ ID NO 12
<211> LENGTH: 515
<212> TYPE: PRT
<213> ORGANISM: Saccharomycopsis fibuligera

<400> SEQUENCE: 12

Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
                20                  25                  30

Ala Tyr Ser Gly Tyr Thr Val Ala Arg Ser Asn Phe Thr Gln Trp Ile
            35                  40                  45

His Glu Gln Pro Ala Val Ser Trp Tyr Tyr Leu Leu Gln Asn Ile Asp
        50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
                100                 105                 110

Phe Ser Asn Thr Thr Leu Ala Lys Val Val Glu Tyr Tyr Ile Ser Asn
            115                 120                 125

Thr Tyr Thr Leu Gln Arg Val Ser Asn Pro Ser Gly Asn Phe Asp Ser
        130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
    210                 215                 220

Ser Thr His Trp Ser Thr Ser Gly Phe Asp Leu Trp Glu Glu Asn Gln
225                 230                 235                 240
```

```
Gly Thr His Phe Phe Thr Ala Leu Val Gln Leu Lys Ala Leu Ser Tyr
            245                 250                 255

Gly Ile Pro Leu Ser Lys Thr Tyr Asn Asp Pro Gly Phe Thr Ser Trp
        260                 265                 270

Leu Glu Lys Gln Lys Asp Ala Leu Asn Ser Tyr Ile Asn Ser Ser Gly
    275                 280                 285

Phe Val Asn Ser Gly Lys Lys His Ile Val Glu Ser Pro Gln Leu Ser
290                 295                 300

Ser Arg Gly Gly Leu Asp Ser Ala Thr Tyr Ile Ala Ala Leu Ile Thr
305                 310                 315                 320

His Asp Ile Gly Asp Asp Thr Tyr Thr Pro Phe Asn Val Asp Asn
                325                 330                 335

Ser Tyr Val Leu Asn Ser Leu Tyr Tyr Leu Val Asp Asn Lys Asn
                340                 345                 350

Arg Tyr Lys Ile Asn Gly Asn Tyr Lys Ala Gly Ala Val Gly Arg
            355                 360                 365

Tyr Pro Glu Asp Val Tyr Asn Gly Val Gly Thr Ser Glu Gly Asn Pro
        370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
                405                 410                 415

Tyr Asp Leu Tyr Asn Ser Phe Ile Ala Asp Leu Ser Lys Ile Asp Ser
            420                 425                 430

Ser Tyr Ala Ser Lys Asp Ser Leu Thr Leu Thr Tyr Gly Ser Asp Asn
        435                 440                 445

Tyr Lys Asn Val Ile Lys Ser Leu Leu Gln Phe Gly Asp Ser Phe Leu
450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 13
<211> LENGTH: 516
<212> TYPE: PRT
<213> ORGANISM: Artificial Sequence
<220> FEATURE:
<223> OTHER INFORMATION: MFalpha2- Sf GA protein

<400> SEQUENCE: 13

Met Lys Phe Ile Ser Thr Phe Leu Thr Phe Ile Leu Ala Ala Val Ser
1               5                  10                  15

Val Thr Ala Val Pro Val Glu Leu Asp Lys Arg Asn Thr Gly His Phe
            20                  25                  30

Gln Ala Tyr Ser Gly Tyr Thr Val Ala Arg Ser Asn Phe Thr Gln Trp
        35                  40                  45

Ile His Glu Gln Pro Ala Val Ser Trp Tyr Tyr Leu Leu Gln Asn Ile
    50                  55                  60

Asp Tyr Pro Glu Gly Gln Phe Lys Ser Ala Lys Pro Gly Val Val Val
65                  70                  75                  80
```

-continued

```
Ala Ser Pro Ser Thr Ser Glu Pro Asp Tyr Phe Tyr Gln Trp Thr Arg
                 85                  90                  95
Asp Thr Ala Ile Thr Phe Leu Ser Leu Ile Ala Glu Val Glu Asp His
            100                 105                 110
Ser Phe Ser Asn Thr Thr Leu Ala Lys Val Val Glu Tyr Tyr Ile Ser
            115                 120                 125
Asn Thr Tyr Thr Leu Gln Arg Val Ser Asn Pro Ser Gly Asn Phe Asp
        130                 135                 140
Ser Pro Asn His Asp Gly Leu Gly Glu Pro Lys Phe Asn Val Asp Asp
145                 150                 155                 160
Thr Ala Tyr Thr Ala Ser Trp Gly Arg Pro Gln Asn Asp Gly Pro Ala
                165                 170                 175
Leu Arg Ala Tyr Ala Ile Ser Arg Tyr Leu Asn Ala Val Ala Lys His
            180                 185                 190
Asn Asn Gly Lys Leu Leu Leu Ala Gly Gln Asn Gly Ile Pro Tyr Ser
        195                 200                 205
Ser Ala Ser Asp Ile Tyr Trp Lys Ile Ile Lys Pro Asp Leu Gln His
    210                 215                 220
Val Ser Thr His Trp Ser Thr Ser Gly Phe Asp Leu Trp Glu Glu Asn
225                 230                 235                 240
Gln Gly Thr His Phe Phe Thr Ala Leu Val Gln Leu Lys Ala Leu Ser
                245                 250                 255
Tyr Gly Ile Pro Leu Ser Lys Thr Tyr Asn Asp Pro Gly Phe Thr Ser
            260                 265                 270
Trp Leu Glu Lys Gln Lys Asp Ala Leu Asn Ser Tyr Ile Asn Ser Ser
        275                 280                 285
Gly Phe Val Asn Ser Gly Lys Lys His Ile Val Glu Ser Pro Gln Leu
    290                 295                 300
Ser Ser Arg Gly Gly Leu Asp Ser Ala Thr Tyr Ile Ala Ala Leu Ile
305                 310                 315                 320
Thr His Asp Ile Gly Asp Asp Thr Tyr Thr Pro Phe Asn Val Asp
                325                 330                 335
Asn Ser Tyr Val Leu Asn Ser Leu Tyr Tyr Leu Leu Val Asp Asn Lys
            340                 345                 350
Asn Arg Tyr Lys Ile Asn Gly Asn Tyr Lys Ala Gly Ala Ala Val Gly
        355                 360                 365
Arg Tyr Pro Glu Asp Val Tyr Asn Gly Val Gly Thr Ser Glu Gly Asn
    370                 375                 380
Pro Trp Gln Leu Ala Thr Ala Tyr Ala Gly Gln Thr Phe Tyr Thr Leu
385                 390                 395                 400
Ala Tyr Asn Ser Leu Lys Asn Lys Asn Leu Val Ile Glu Lys Leu
                405                 410                 415
Asn Tyr Asp Leu Tyr Asn Ser Phe Ile Ala Asp Leu Ser Lys Ile Asp
            420                 425                 430
Ser Ser Tyr Ala Ser Lys Asp Ser Leu Thr Leu Thr Tyr Gly Ser Asp
        435                 440                 445
Asn Tyr Lys Asn Val Ile Lys Ser Leu Leu Gln Phe Gly Asp Ser Phe
    450                 455                 460
Leu Lys Val Leu Leu Asp His Ile Asp Asp Asn Gly Gln Leu Thr Glu
465                 470                 475                 480
Glu Ile Asn Arg Tyr Thr Gly Phe Gln Ala Gly Ala Val Ser Leu Thr
                485                 490                 495
Trp Ser Ser Gly Ser Leu Leu Ser Ala Asn Arg Ala Arg Asn Lys Leu
```

```
                500              505              510
Ile Glu Leu Leu
        515

<210> SEQ ID NO 14
<211> LENGTH: 514
<212> TYPE: PRT
<213> ORGANISM: Artificial Sequence
<220> FEATURE:
<223> OTHER INFORMATION: MFa1-Sf GA protein  sequence

<400> SEQUENCE: 14

Met Phe Lys Ser Val Val Tyr Ser Ile Leu Ala Ala Ser Leu Ala Asn
1               5                   10                  15

Ala Val Pro Val Glu Leu Asp Lys Arg Asn Thr Gly His Phe Gln Ala
            20                  25                  30

Tyr Ser Gly Tyr Thr Val Ala Arg Ser Asn Phe Thr Gln Trp Ile His
        35                  40                  45

Glu Gln Pro Ala Val Ser Trp Tyr Tyr Leu Leu Gln Asn Ile Asp Tyr
    50                  55                  60

Pro Glu Gly Gln Phe Lys Ser Ala Lys Pro Gly Val Val Ala Ser
65                  70                  75                  80

Pro Ser Thr Ser Glu Pro Asp Tyr Phe Tyr Gln Trp Thr Arg Asp Thr
                85                  90                  95

Ala Ile Thr Phe Leu Ser Leu Ile Ala Glu Val Glu Asp His Ser Phe
            100                 105                 110

Ser Asn Thr Thr Leu Ala Lys Val Val Glu Tyr Tyr Ile Ser Asn Thr
        115                 120                 125

Tyr Thr Leu Gln Arg Val Ser Asn Pro Ser Gly Asn Phe Asp Ser Pro
    130                 135                 140

Asn His Asp Gly Leu Gly Glu Pro Lys Phe Asn Val Asp Thr Ala
145                 150                 155                 160

Tyr Thr Ala Ser Trp Gly Arg Pro Gln Asn Asp Gly Pro Ala Leu Arg
                165                 170                 175

Ala Tyr Ala Ile Ser Arg Tyr Leu Asn Ala Val Ala Lys His Asn Asn
            180                 185                 190

Gly Lys Leu Leu Leu Ala Gly Gln Asn Gly Ile Pro Tyr Ser Ser Ala
        195                 200                 205

Ser Asp Ile Tyr Trp Lys Ile Ile Lys Pro Asp Leu Gln His Val Ser
    210                 215                 220

Thr His Trp Ser Thr Ser Gly Phe Asp Leu Trp Glu Glu Asn Gln Gly
225                 230                 235                 240

Thr His Phe Phe Thr Ala Leu Val Gln Leu Lys Ala Leu Ser Tyr Gly
                245                 250                 255

Ile Pro Leu Ser Lys Thr Tyr Asn Asp Pro Gly Phe Thr Ser Trp Leu
            260                 265                 270

Glu Lys Gln Lys Asp Ala Leu Asn Ser Tyr Ile Asn Ser Ser Gly Phe
        275                 280                 285

Val Asn Ser Gly Lys Lys His Ile Val Glu Ser Pro Gln Leu Ser Ser
    290                 295                 300

Arg Gly Gly Leu Asp Ser Ala Thr Tyr Ile Ala Leu Ile Thr His
305                 310                 315                 320

Asp Ile Gly Asp Asp Thr Tyr Thr Pro Phe Asn Val Asp Asn Ser
                325                 330                 335

Tyr Val Leu Asn Ser Leu Tyr Tyr Leu Leu Val Asp Asn Lys Asn Arg
```

```
          340                 345                 350
Tyr Lys Ile Asn Gly Asn Tyr Lys Ala Gly Ala Ala Val Gly Arg Tyr
            355                 360                 365

Pro Glu Asp Val Tyr Asn Gly Val Gly Thr Ser Glu Gly Asn Pro Trp
    370                 375                 380

Gln Leu Ala Thr Ala Tyr Ala Gly Gln Thr Phe Tyr Thr Leu Ala Tyr
385                 390                 395                 400

Asn Ser Leu Lys Asn Lys Lys Asn Leu Val Ile Glu Lys Leu Asn Tyr
                405                 410                 415

Asp Leu Tyr Asn Ser Phe Ile Ala Asp Leu Ser Lys Ile Asp Ser Ser
            420                 425                 430

Tyr Ala Ser Lys Asp Ser Leu Thr Leu Thr Tyr Gly Ser Asp Asn Tyr
        435                 440                 445

Lys Asn Val Ile Lys Ser Leu Leu Gln Phe Gly Asp Ser Phe Leu Lys
    450                 455                 460

Val Leu Leu Asp His Ile Asp Asp Asn Gly Gln Leu Thr Glu Glu Ile
465                 470                 475                 480

Asn Arg Tyr Thr Gly Phe Gln Ala Gly Ala Val Ser Leu Thr Trp Ser
                485                 490                 495

Ser Gly Ser Leu Leu Ser Ala Asn Arg Ala Arg Asn Lys Leu Ile Glu
            500                 505                 510

Leu Leu

<210> SEQ ID NO 15
<211> LENGTH: 7401
<212> TYPE: DNA
<213> ORGANISM: Artificial Sequence
<220> FEATURE:
<223> OTHER INFORMATION: MFa1-Sf GA

<400> SEQUENCE: 15
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accacgcttt tcaattcaat tcatcatttt ttttttattc ttttttttga tttcggtttc    240
tttgaaattt ttttgattcg gtaatctccg aacagaagga agaacgaagg aaggagcaca    300
gacttagatt ggtatatata cgcatatgta gtgttgaaga acatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga gcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
```

```
tctctacagg atctgacatt attattgttg gaagaggact atttgcaaag ggaagggatg    1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta acgttaata ttttgttaaa attcgcgtta     1380
aatttttgtt aaatcagctc attttttaac caataggccg aaatcggcaa aatcccttat    1440
aaatcaaaag aatagaccga datagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttgggt cgaggtgccg taaagcacta      1620
aatcggaacc ctaaagggag ccccgattt agagcttgac ggggaaagcc ggcgaacgtg     1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
gggttttccc agtcacgacg ttgtaaaacg acggccagtg aattgtaata cgactcacta    1980
tagggcgaat ggagctcca ccgcggtggc ggccgcctcg agatctcccc taaaccgtgg     2040
aatatttcgg atatccttt gttgtttccg ggtgtacaat atggacttcc tcttttctgg     2100
caaccaaacc catacatcgg gattcctata ataccttcgt tggtctccct aacatgtagg    2160
tggcggaggg gagatataca atagaacaga taccagacaa gacataatgg gctaaacaag    2220
actacaccaa ttacactgcc tcattgatgg tggtacataa cgaactaata ctgtagccct    2280
agacttgata gccatcatca tatcgaagtt tcactaccct ttttccattt gccatctatt    2340
gaagtaataa taggcgcatg caacttcttt tcttttttt tcttttctct ctccccgtt      2400 gttgtctcac catatccgca atgacaaaaa aatgatggaa gacactaaag gaaaaaatta    2460
acgacaaaga cagcaccaac agatgtcgtt gttccagagc tgatgggggg tatctcgaag    2520
cacacgaaac tttttccttc cttcattcac gcacactact ctctaatgag caacggtata    2580
cggccttcct tccagttact tgaatttgaa ataaaaaaag tttgctgtct tgctatcaag    2640
tataaataga cctgcaatta ttaatctttt gtttcctcgt cattgttctc gttccctttc    2700
ttccttgttt cttttttctgc acaatatttc aagctatacc aagcatacaa tcaactatct    2760
catatacaat gcaaccatcc actgctactg ctgcccccaaa ggaaaaaacc tcctctgaaa   2820
agaaagacaa tgttccagtt gaattggata agagaaacac cggtcatttc caagcttatt    2880
ctggttatac cgttgctaga tctaacttca cccaatggat tcatgaacaa ccagctgttt    2940
cttggtacta cttgttgcaa aacatcgatt acccagaagg tcaattcaaa tctgctaaac    3000
caggtgttgt tgttgcttct ccatctacat ctgaaccaga ttacttctac caatggacta    3060
gagataccgc tattaccttc ttgtccttga ttgctgaagt tgaagatcat tctttctcca    3120
acactacctt ggctaaggtt gtcgaatatt acatttccaa cacctacacc ttgcaaagag    3180
tttctaatcc atccggtaac ttcgattctc caaatcatga tggtttgggt gaacctaagt    3240
tcaacgttga tgatactgct tatacagctt cttgggggtag accacaaaat gatggtccag    3300 cttttgagagc ttacgctatt tctagatact tgaacgctgt tgctaagcac aacaacggta    3360
aattattatt ggccggtcaa aacggtatt cttattcttc tgcttccgat atctactgga     3420
```

```
agattattaa gccagacttg caacatgttt ctactcattg gtctacctct ggttttgatt    3480
tgtgggaaga aaatcaaggt actcatttct tcaccgcttt ggttcaattg aaggctttgt    3540
cttacggtat tccattgtct aagacctaca atgatccagg tttcacttct tggttggaaa    3600
aacaaaagga tgccttgaac tcctacatta actcttccgg tttcgttaac tctggtaaaa    3660
agcacatcgt tgaatctcca caattgtcat ctagaggtgg tttggattct gctacttata    3720
ttgctgcctt gatcacccat gatatcggtg atgatgatac ttacacccca ttcaatgttg    3780
ataactccta cgttttgaac tccttgtatt acctattggt cgacaacaag aacagataca    3840
agatcaacgg taactacaaa gctggtgctg ctgttggtag atatcctgaa gatgtttaca    3900
acggtgttgg tacttctgaa ggtaatccat ggcaattggc tactgcttat gctggtcaaa    3960
ctttttacac cttggcctac aattccttga agaacaagaa gaacttggtc atcgaaaagt    4020
tgaactacga cttgtacaac tccttcattg ctgatttgtc caagattgat tcttcctacg    4080
cttctaagga ttctttgact ttgacctacg gttccgataa ctacaagaac gttatcaagt    4140
ccttgttgca attcggtgac tcattcttga aggttttgtt ggatcacatc gatgacaacg    4200
gtcaattgac tgaagaaatc aacagataca ccggttttca agctggtgca gtttctttga    4260
cttggtcatc tggttctttg ttgtctgcta atagagccag aaaacaagttg atcgaattat    4320 tgtgtgttat tgcctaaaca ggccccttttt cctttgtcga tatcatgtaa ttagttatgt    4380
cacgcttaca ttcacgccct cctcccacat ccgctctaac cgaaaaggaa ggagttagac    4440
aacctgaagt ctaggtccct atttattttt ttatagttat gttagtatta agaacgttat    4500
ttatatttca aattttttctt ttttttctgt acaaacgcgt gtacgcatgt aacgggcaga    4560
cgaattcgat atcaagctta tcgataccgt cgacctcgag ggggggcccg gtaccagctt    4620
ttgttccctt tagtgagggt taattccgag cttggcgtaa tcatggtcat agctgtttcc    4680
tgtgtgaaat tgttatccgc tcacaattcc acacaacata ggagccggaa gcataaagtg    4740
taaagcctgg ggtgcctaat gagtgaggta actcacatta attgcgttgc gctcactgcc    4800
cgctttccag tcgggaaacc tgtcgtgcca gctgcattaa tgaatcggcc aacgcgcggg    4860
gagaggcggt ttgcgtattg ggcgctcttc cgcttcctcg ctcactgact cgctgcgctc    4920
ggtcgttcgg ctgcggcgag cggtatcagc tcactcaaag gcggtaatac ggttatccac    4980
agaatcaggg gataacgcag gaaagaacat gtgagcaaaa ggccagcaaa aggccaggaa    5040
ccgtaaaaag gccgcgttgc tggcgttttt ccataggctc ggcccccctg acgagcatca    5100
caaaaatcga cgctcaagtc agaggtggcg aaacccgaca ggactataaa gataccaggc    5160 gttccccccct ggaagctccc tcgtgcgctc tcctgttccg accctgccgc ttaccggata    5220
cctgtccgcc tttctccctt cgggaagcgt ggcgctttct caatgctcac gctgtaggta    5280
tctcagttcg gtgtaggtcg ttcgctccaa gctgggctgt gtgcacgaac cccccgttca    5340
gcccgaccgc tgcgccttat ccggtaacta tcgtcttgag tccaacccgg taagacacga    5400
cttatcgcca ctggcagcag ccactggtaa caggattagc agagcgaggt atgtaggcgg    5460
tgctacagag ttcttgaagt ggtggcctaa ctacggctac actagaagga cagtatttgg    5520
tatctgcgct ctgctgaagc cagttacctt cggaaaaaga gttggtagct cttgatccgg    5580
caaacaaacc accgctggta gcggtggttt ttttgtttgc aagcagcaga ttacgcgcag    5640
aaaaaaagga tctcaagaag atcctttgat cttttctacg gggtctgacg ctcagtggaa    5700
cgaaaactca cgttaaggga ttttggtcat gagattatca aaaaggatct tcacctagat    5760
ccttttaaat taaaaatgaa gttttaaatc aatctaaagt atatatgagt aaacttggtc    5820
```

-continued

```
tgacagttac caatgcttaa tcagtgaggc acctatctca gcgatctgtc tatttcgttc    5880
atccatagtt gcctgactgc ccgtcgtgta gataactacg atacgggagg gcttaccatc    5940 tggcccagt  gctgcaatga taccgcgaga cccacgctca ccggctccag atttatcagc    6000
aataaaccag ccagccggaa gggccgagcg cagaagtggt cctgcaactt tatccgcctc    6060
catccagtct attaattgtt gccgggaagc tagagtaagt agttcgccag ttaatagttt    6120
gcgcaacgtt gttgccattg ctacaggcat cgtggtgtca cgctcgtcgt ttggtatggc    6180
ttcattcagc tccggttccc aacgatcaag gcgagttaca tgatccccca tgttgtgaaa    6240
aaaagcggtt agctccttcg gtcctccgat cgttgtcaga agtaagttgg ccgcagtgtt    6300
atcactcatg gttatggcag cactgcataa ttctcttact gtcatgccat ccgtaagatg    6360
cttttctgtg actggtgagt actcaaccaa gtcattctga gaatagtgta tgcggcgacc    6420
gagttgctct tgcccggcgt caatacggga taataccgcg ccacatagca gaactttaaa    6480
agtgctcatc attggaaaac gttcttcggg gcgaaaactc tcaaggatct taccgctgtt    6540
gagatccagt tcgatgtaac ccactcgtgc acccaactga tcttcagcat ctttactttt    6600
caccagcgtt tctgggtgag caaaaacagg aaggcaaaat gccgcaaaaa agggaataag    6660
ggcgacacgg aaatgttgaa tactcatact cttcctttt  caatattatt gaagcattta    6720
tcagggttat tgtctcatga gcggatacat atttgaatgt atttagaaaa ataaacaaat    6780
aggggttccg cgcacatttc cccgaaaagt gccacctggg tccttttcat cacgtgctat    6840
aaaaataatt ataatttaaa ttttttaata taaatatata aattaaaaat agaaagtaaa    6900
aaaagaaatt aaagaaaaaa tagttttgt  tttccgaaga tgtaaaagac tctagggga    6960 tcgccaacaa atactacctt ttatcttgct cttcctgctc tcaggtatta atgccgaatt    7020
gtttcatctt gtctgtgtag aagaccacac acgaaaatcc tgtgatttta cattttactt    7080
atcgttaatc gaatgtatat ctatttaatc tgcttttctt gtctaataaa tatatatgta    7140
aagtacgctt tttgttgaaa ttttttaaac ctttgtttat ttttttttct tcattccgta    7200
actcttctac cttctttatt tactttctaa aatccaaata caaaacataa aaataaataa    7260
acacagagta aattcccaaa ttattccatc attaaaagat acgaggcgcg tgtaagttac    7320
aggcaagcga tccgtcctaa gaaaccatta ttatcatgac attaacctat aaaaataggc    7380
gtatcacgag gccctttcgt c                                             7401
```

MICROORGANISMS EXPRESSING MODIFIED GLUCOAMYLASE ENZYMES

CROSS-REFERENCE TO RELATED APPLICATIONS

This application is a Continuation of U.S. patent application Ser. No. 15/548,812, filed Aug. 4, 2017, and entitled MODIFIED GLUCOAMYLASE ENZYMES AND YEAST STRAINS HAVING ENHANCED BIOPRODUCT PRODUCTION, which is a national phase application of International Application No. PCT/US2016/016822, filed Feb. 5, 2016, and entitled MODIFIED GLUCOAMYLASE ENZYMES AND YEAST STRAINS HAVING ENHANCED BIOPRODUCT PRODUCTION, which claims the benefit of U.S. Provisional Patent Application No. 62/112,807, filed Feb. 6, 2015, entitled MODIFIED GLUCOAMYLASE ENZYMES AND YEAST STRAINS HAVING ENHANCED BIOPRODUCT PRODUCTION, each of which is hereby incorporated by reference in its entirety.

SEQUENCE LISTING

This application contains a Sequence Listing which has been submitted electronically in ASCII text file format, entitled "N00275_ST25.txt," created on Aug. 4, 2017, and having a size of 87 kilobytes, which is hereby incorporated by reference in its entirety.

FIELD OF THE INVENTION

The current invention relates to modified glucoamylase enzymes, microorganisms expressing these enzymes, and fermentations methods for producing ethanol.

BACKGROUND

Ethanol production by fermentation is a well know industrial process. However increasing ethanol yields can be technically difficult. There are various factors that make it challenging for microorganisms to grow in fermentation conditions designed for increased ethanol production. For example, the fermentation medium may have higher substrate concentrations to promote ethanol production, but these conditions can have a negative impact on cell growth. Also, increased ethanol concentration and accumulation of undesirable byproducts can also be detrimental to cell health. Yeast strains have been selected for tolerance to these conditions, which can result in improved ethanol yields. In particular, the ethanol tolerant strains of the yeast *Saccharomyces cerevisiae* have been used in industrial settings as a workhorse microorganism for producing ethanol.

Molecular techniques have led to the identification of genes that are associated with ethanol tolerance. For example, Kajiwara (Appl Microbiol Biotechnol. 2000; 53:568-74.) reports that overexpression of the OLE1 gene which is involved in unsaturated fatty acid (UFA) synthesis resulted in higher unsaturated fatty acid levels in the cell and higher ethanol production. Other research has found that accumulation of trehalose by disruption of the trehalose-hydrolyzing enzyme, acid trehalase (ATH) (Kim et al., Appl Environ Microbiol. 1996; 62:1563-1569) or accumulation of proline L-proline by a strain carrying a PRO1 gamma-glutamyl kinase mutation (Takagi, et al., Appl Environ Microbiol. 2005; 71:8656-8662.) improves ethanol tolerance in yeast. Ergosterol is closely associated with ethanol tolerance of *Saccharomyces cerevisiae* (Inoue, et al., Biosci Biotechnol Biochem. 2000; 64:229-236). While advancements have been made in this area, use of genetically modified strains that demonstrate ethanol tolerance may not alone be sufficient to provide desired levels of ethanol during a fermentation process.

In addition to the genetic profile of the fermentation microorganism, the components of the fermentation medium can have a significant impact on ethanol production. In fermentation processes, a carbohydrate or carbohydrate mixture is present in the medium. Starch is a widely available and inexpensive carbohydrate source. It is available from a wide variety of plant sources such as corn, wheat, rice, barley, and the like. Many organisms are not capable of metabolizing starch directly, or else metabolize it slowly and inefficiently.

Accordingly, it is common to treat starch before feeding it into the fermentation process, in order to break it down into monosaccharides that the organism can ferment easily. Usually, starch is hydrolyzed to form a mixture containing mainly glucose (i.e., dextrose). However, the pre-treatment of a starch composition in preparation for fermentation can be expensive and labor intensive as it commonly involves the addition of purified starch-degrading enzymes to the starch material and requires additional steps prior to carrying out fermentation. Further, complete hydrolysis to glucose adds significant cost, so most commercially available glucose products tend to contain a small amount of various oligomeric polysaccharides.

A significant portion of the cost to produce starch based ethanol is the enzymes that break down the starch into fermentable sugars. Various molecular techniques have been attempted in *Saccharomyces cerevisiae* to reduce or eliminate the need to add amylolytic enzymes to the fermentation medium, but these approaches have yielded varying degrees of success. A potential limiting factor affecting the commercial viability of engineered strains is the ability of *Saccharomyces cerevisiae* to secrete large amounts of foreign protein.

SUMMARY OF THE INVENTION

The invention relates to fermentation methods including non-natural yeast that provide high levels of glucoamylase activity in the fermentation medium. The current invention also relates to glucoamylase enzymes (E.C. 3.2.1.3) that are modified to partially or fully replace their natural secretion sequence with a heterologous secretion sequence. The invention also relates to genes encoding these secretion sequence-modified glucoamylase enzymes, as well as microorganisms expressing these genes. The invention also relates to methods of for producing bio-derived products (fermentation products) manufactured by the organism, such as ethanol. The invention also relates to fermentation coproducts which can be used for other types of compositions, such as animal feed compositions.

In experimental studies associated with the current application, it has been found that the *Saccharomyces cerevisiae* mating factor alpha 2 (ScMFα2) secretion signal and the *Saccharomyces cerevisiae* repressible acid phosphatase (ScPHO5) secretion signal, when attached to a glucoamylase enzyme and expressed in microbial cells, can promote high levels of ethanol production during fermentation. Surprisingly, it was found that adding a ScMFα2 secretion signal or ScPHO5 secretion signal to a naturally secreted yeast glucoamylase allowed cells expressing such a modified enzyme to generate substantially more ethanol in the fermentation medium. Some aspects of the invention uses a *Saccharo*

*mycopsis fibuligera* glucoamylase (herein "Sf GA"), of an amylolytically active portion thereof, such as a Sf GA having 90% or greater sequence identify to amino acids 27-515 of SEQ ID NO:1 for making the Sc MFα2 or Sc PHO5 secretion signal-glucoamylase.

Therefore, aspects of the invention provide a polypeptide comprising (a) a secretion signal amino acid sequence having 90% or greater identity to SEQ ID NO:3 (the Sc MFα2 secretion signal) or SEQ ID NO:5 (the Sc PHO5 secretion signal) and (b) a glucoamylase amino acid sequence from a yeast, fungal, or bacterial glucoamylase polypeptide, wherein the polypeptide has glucoamylase activity. In some aspects the glucoamylase amino acid sequence is based on a glucoamylase sequence from *Saccharomycopsis fibuligera*. In some aspects, the glucoamylase amino acid sequence has 90% or greater sequence identify to amino acids 27-515 of SEQ ID NO:1, which includes the amylolytically active portion of a Sf GA glucoamylase termed "Sf GA-1." In some aspects the polypeptide has 95% or greater sequence identity to SEQ ID NO:7 (Sc MFα2 SS-Sf GA-1) or has 95% or greater sequence identity to SEQ ID NO:9 (Sc PHO5 SS-Sf GA-1)

Aspects of the invention also provide a nucleic acid sequence that encodes a Sc MFα2 secretion signal—glucoamylase enzyme or a Sc PHO5 secretion signal—glucoamylase enzyme. Aspects include nucleic acids having 75% or greater identity to SEQ ID NO:8 (encoding Sc MFα2 SS-Sf GA-1) or having 75% or greater identity to SEQ ID NO:10 (encoding Sc PHO5 SS-Sf GA-1). These aspects include constructs wherein the nucleic acid is present on a vector construct, which may include one or more of the following sequences: a promoter sequence, a terminator sequence, a selectable marker sequence, a genomic integration sequence, and/or a replication origin sequence. The nucleic acid can be integrated into one or more locations of the hosts genomic DNA, or can be present within the cell but not integrated, such as on a plasmid or episomal construct. The invention also provides nucleic acids, such as DNA oligomers (e.g., single stranded DNA PCR primers, or longer linear DNA segments) that can be useful for the detection of the glucoamylase gene with the Sc MFα2 or Sc PHO5 secretion sequence in a cell.

Aspects of the invention also provide a host cell expressing the Sc MFα2 secretion signal—glucoamylase enzyme or a Sc PHO5 secretion signal—glucoamylase enzyme. Is some aspects, the host cell is capable of secreting the enzyme into medium in which the cell is present. The host cell can also be tolerant to a bio-derived product of the cell, such as ethanol or another product, derived from precursors resulting from the amylolytic activity of the enzyme. For example, the host cell can be a commercially available strain or one having one or more specific genetic modifications that provide an increase in tolerance to a bioderived product, such as increased ethanol tolerance. Exemplary host cells include fungal cells such as *Saccharomyces cerevisiae*.

Aspects of the invention also provide a method for producing a bio-derived product. The method comprises providing a fermentation medium comprising a host cell expressing the Sc MFα2 secretion signal—glucoamylase enzyme or a Sc PHO5 secretion signal—glucoamylase enzyme, wherein a bio-derived product is produced by a fermentation process. The bio-derived product can be one that is derived from enzymatic degradation of a product of a glucose polymer such as starch, amylose, or amylopectin. In an exemplary method, an alcohol (i.e. ethanol) is produced by a fermentation method. In another exemplary method, an organic acid (i.e. lactic acid) is produced by a fermentation method.

Aspects of the invention also provide a method for treating medium comprising a glucose polymer such as starch, amylase, or amylopectin. The method comprises providing medium comprising a glucose polymer and a host cell expressing the Sc MFα2 secretion signal—glucoamylase enzyme or a Sc PHO5 secretion signal—glucoamylase enzyme. In the method, the glucose polymer contacts the glucoamylase enzyme secreted from the cell and the glucose polymer is degraded to glucose. The treated medium can be used for a fermentation process using a different cell, or can be used for a non-fermentation process.

Another aspect of the invention is a fermentation method for producing a fermentation product. The method includes a step of fermenting a liquid medium comprising a starch material and a non-natural yeast comprising an exogenous nucleic acid encoding a polypeptide comprising an glucoamylase. The non-natural yeast provides the medium with an amount of glucoamylase activity of 2.25 U or greater per gram of biomass.

Aspects of the invention also provide a method for producing ethanol by fermentation, wherein the ethanol is present in the fermentation medium at a concentration of 90 g/L or greater. In the method, a liquid medium comprising a starch material and a non-natural yeast comprising a exogenous nucleic acid encoding polypeptide comprising a glucoamylase portion and a signal sequence heterologous to the glucoamylase is fermented. Fermentation can provide an ethanol concentration of about 90 g/L or greater in the liquid medium, such as in the range of about 90 g/L to about 170 g/L.

In another aspect, the invention provides methods and compositions that can be used to prepare feed compositions. The feed compositions include fermentation medium co-products obtained from a fermentation medium derived from the non-natural yeast of the disclosure. For example, after a fermentation process has been completed, some or all of a bioproduct can be removed from the fermentation medium to provide a refined composition comprising non-bioproduct solids. The non-bioproduct solids can include the non-natural yeast, feedstock material in the medium that is not utilized by the yeast, as well as fermentation by-products. The refined composition can be used to form a feed composition, such as a livestock feed composition. The refined composition comprising non-bioproduct solids can provide carbohydrate and protein supplements to improve the nutritional content of a feed composition.

BRIEF DESCRIPTION OF THE FIGURES

FIG. 1 is a picture of a protein gel comparing concentrated extracts from strains of the disclosure.

DETAILED DESCRIPTION

The aspects of the present invention described below are not intended to be exhaustive or to limit the invention to the precise forms disclosed in the following detailed description. Rather a purpose of the aspects chosen and described is so that the appreciation and understanding by others skilled in the art of the principles and practices of the present invention can be facilitated.

Aspects of the invention relate to glucoamylase genes that are modified to replace their natural secretion sequence with a heterologous secretion sequence that is either the *Saccha-*

*romyces cerevisiae* mating factor alpha 2 (Sc MFα2) secretion signal or the *Saccharomyces cerevisiae* repressible acid phosphatase (Sc PHO5) secretion signal. Nucleic acids capable of serving as templates for the expression of these enzymes are also aspects of the invention.

Aspects of the invention also relate to as microorganisms expressing these enzymes, in particular, fungal organisms such as yeast (e.g., *Saccharomyces cerevisiae*). Such organisms can express a glucoamylase enzyme with either a Sc MFα2 or a Sc PHO5 secretion signal. The glucoamylase enzyme can be secreted from the cell to a fermentation medium where the enzyme can have amylolytic activity on glucose polymers present in the fermentation medium. In turn, the enzyme can cause degradation of the glucose polymers to glucose, which can enter the cell and be used as a carbon source for the production of a target compound, such as ethanol.

The term "exogenous" as used herein, means that a molecule, such as a nucleic acid, or an activity, such as an enzyme activity, is introduced into the host organism. An exogenous nucleic acid can be introduced in to the host organism by well-known techniques and can be maintained external to the hosts chromosomal material (e.g., maintained on a non-integrating vector), or can be integrated into the host's chromosome, such as by a recombination event. An exogenous nucleic acid can encode an enzyme, or portion thereof, that is either homologous or heterologous to the host organism.

The term "heterologous" refers to a molecule or activity that is from a source that is different than the referenced molecule or organism. For example, in the context of the disclosure, a "heterologous signal sequence" refers to a signal sequence that is different from the referenced polypeptide or enzyme. Therefore, when a native signal sequence is removed from a glucoamylase enzyme and replaced with a signal sequence from a different polypeptide, the modified glucoamylase has a "heterologous signal sequence." Accordingly, a gene or protein that is heterologous to a referenced organism is a gene or protein not found in that organism. For example, a specific glucoamylase gene found in a first fungal species and exogenously introduced into a second fugal species that is the host organism is "heterologous" to the second fungal organism.

Glucoamylases (E.C. 3.2.1.3) are amylolytic enzymes that hydrolyze 1,4-linked a-D-glucosyl residues successively from the nonreducing end of oligo- and polysaccharide chains with the release of D-glucose Glucoamylases and can also cleave α-1,6 bonds on amylopectin branching points. As used herein, the term "amylolytic activity" with reference to the Sc MFα2 or Sc PHO5 secretion signal-glucocamylase pertains to these enzymatic mechanisms. A glucoamylase polypeptide can be a variant of a naturally occurring glucoamylase, or a portion of a naturally occurring glucoamylase (such as a glucoamylase that is truncated at its N-terminus, its C-terminus, or both), while the glucoamylase polypeptide retains amylolytic activity.

Alternative names for glucoamylases include amyloglucosidase; γ-amylase; lysosomal α-glucosidase; acid maltase; exo-1,4-α-glucosidase; glucose amylase; γ-1,4-glucan glucohydrolase; acid maltase; 1,4-α-D-glucan glucohydrolase.

Most glucoamylases are multidomain enzymes. Many glucoamylases include a starch-binding domain connected to a catalytic domain via an O-glycosylated linker region. The starch-binding domain may fold as an antiparallel beta-barrel and may have two binding sites for starch or beta-cyclodextrin. However, some glucoamylases do not include a starch binding domain (e.g., see Hostinova et al., Archives of Biochemistry and Biophysics, 411:189-195, 2003), or include a non-canonical starch binding domain. For example, the *Rhizopus oryzae* glucoamylase possesses a C-terminal raw starch binding domain, and the *Saccharomycopsis fibuligera* IFO 0111 glucoamylase lacks a clear starch binding domain (Hostinova et al., supra). Therefore, some aspects of the invention are directed to glucoamylases that do not include a starch binding domain and that have an N-terminus modified with the Sc MFα2 or Sc PHO5 secretion signal, and other aspects are directed to glucoamylases that include a starch binding domain and that have an N-terminus modified with the Sc MFα2 or Sc PHO5 secretion signal.

Glucoamylases may also have a catalytic domain having a configuration of a configured twisted (alpha/alpha)(6)-barrel with a central funnel-shaped active site. Glucoamylases may have a structurally conserved catalytic domain of approximately 450 residues. In some glucoamylases the catalytic domain generally followed by a linker region consisting of between 30 and 80 residues that are connected to a starch binding domain of approximately 100 residues.

Glucoamylase properties may be correlated with their structural features. A structure-based multisequence alignment was constructed using information from catalytic and starch-binding domain models (see, e.g., Coutinho, P. M., and Reilly, P. J., 1994. Protein Eng. 7:393-400 and 749-760). It has been shown that the catalytic and starch binding domains are functionally independent based on structure-function relationship studies, and there are structural similarities in microbial glucoamylases. From other studies, specific glucoamylase residues have been shown to be involved in directing protein conformational changes, substrate binding, thermal stability, and catalytic activity (see, for example, Sierks, M. R., et al. 1993. Protein Eng. 6:75-79; and Sierks, M. R., and Svensson, B. 1993. Biochemistry 32:1113-1117). Therefore, the correlation between glucoamylase sequence and protein function is understood in the art, and one of skill could design and express variants of amylolytically active glucoamylases having one or more amino acid deletion(s), substitution(s), and/or additions. For example, in some aspects, the glucoamylase portion of the Sc MFα2 or Sc PHO5 secretion signal-glucoamylase can contain a truncated version of a naturally occurring glucoamylase, the truncated version having, in the least, a catalytic and optionally a starch-binding domain having amylolytic activity as described herein.

Hostinova et al. (Archives of Biochemistry and Biophysics, 411:189-195, 2003) describes the nucleotide sequence of the glucoamylase gene Glm in the yeast strain *Saccharomycopsis fibuligera* IFO 0111 (referred to herein as "Sf GA-1"). According to Hostinova et al., the *Saccharomycopsis fibuligera* Glm gene is transcribed into a 1.7 kb RNA transcript that codes for a 515 amino acid protein, and is represented by SEQ ID NO:1. In the 515 amino acid-long polypeptide chain 26 N-terminal amino acid residues constitue the signal peptide and subsequent 489 amino acid residues constitute the mature protein. Mature Glm, which lacks the signal sequence and is 489 amino acids long, has a predicted molecular weight of 54,590 Da in deglycosylated form. In an alignment with other glucoamylases, Glm was shown to have homology in the catalytic domain.

Itoh et al. (J. Bacteriol. 169:4171-4176) describes the nucleotide sequence of another glucoamylase gene, GLU1, in the yeast *Saccharomycopsis fibuligera* (referred to herein as "Sf GA-2"). The *Saccharomycopsis fibuligera* GLU1 gene is transcribed into a 2.1 kb RNA transcript that codes for a 519 amino acid protein and has a molecular weight of 57,000 Da. GLU1 has four potential glycosylation sites (for asparagine-linked glycosides having a molecular weight of 2000 Da). GLU1 has four potential glycosylation sites (for asparagine-linked glycosides having a molecular weight of 2000 Da). GLU1 has a natural signal sequence for secretion that is cleaved off, likely during export of the protein. The cleaved site is preceded by the basic amino acids Lys-Arg, thought to be a proteolytic processing signal to yield mature protein.

Itoh et al. (supra) also describes alignment of amino acid sequences of glucoamylases from yeast and fungi. *Saccharomycopsis fibuligera, A. niger, Rhizopus oryzae,* and *Saccharomyces diastaticus,* and *Saccharomyces cerevisiae* were aligned showing five highly homologous segments (S1-S5). These parts of the respective conserved segments were shown to be conformationally similar to each other. The S5 segment, generally located at the carboxy termini, appears to be nonessential to amylolytic activities, since glucoamylases from *Saccharomyces* species lack this region.

In this regard, the invention also contemplates variants and portions of Sf GA having glucoamylase activity. Tables 1 and 2 present a list of various fungal and bacterial glucoamylase genes, including the amino acid location of the native signal sequence, and in some sequences, the propeptide, of the glucoamylase.

TABLE 1

Fungal Glucoamylases

| Name | Accession | Organism | Signal peptide | Pro-peptide | Chain |
|---|---|---|---|---|---|
| GAMP (AMYG_AMORE) | Q03045 | *Amorphotheca resinae* (Creosote fungus) (*Hormoconis resinae*) | 1-29 | | 30-616 |
| GLAA (AMYG_ASPNG) | P69328 | *Aspergillus niger* | 1-18 | 19-24 | 25-640 |
| STA1 (AMYH_YEASX) | P04065 | *Saccharomyces cerevisiae* | 1-21 | | 22-767 |
| STA2 (AMYI_YEASX) | P29760 | *Saccharomyces cerevisiae* | 1-21 | | 22-768 |
| GLAA (AMYG_ASPAW) | P69327 | *Aspergillus awamori* (Black koji mold) | 1-18 | 19-24 | 25-640 |
| glaA (AMYG_ASPOR) | P36914 | *Aspergillus oryzae* (strain ATCC 42149/ RIB 40) (Yellow koji mold) | 1-19 | 20-25 | 26-612 |
| GAA (AMYG_BLAAD) | P42042 | *Blastobotrys adeninivorans* (Yeast) (*Arxula adeninivorans*) | 1-18 | | 19-624 |
| GAM1 (AMYG_SCHOC) | P22861 | *Schwanniomyces occidentalis* (Yeast) (*Debaryomyces occidentalis*) | 1-22 | | 23-958 |
| gaI (AMYG_ASPKA) | P23176 | *Aspergillus kawachii* (White koji mold) (*Aspergillus awamori* var. *kawachi*) | 1-18 | 19-24 | 25-639 |
| glaA (AMYG_ASPSH) | P22832 | *Aspergillus shirousami* | 1-18 | 19-24 | 25-639 |
| GAM1 (AMYG_CANAL) | O74254 | *Candida albicans* (strain SC5314/ ATCC MYA-2876) | 1-20 | | 21-946 |
| AMYG_RHIOR | P07683 | *Rhizopus oryzae* (Mucormycosis agent) (*Rhizopus arrhizus* var. *delemar*) | 1-25 | | 26-604 |
| meu17 (mAMYG_SCHPO) | O60087 | *Schizosaccharomyces pombe* (strain 972/ ATCC 24843) (Fission yeast) | 1-16 | 17-28 | 29-450 |
| | I2K2N7 | *Brettanomyces bruxellensis* AWRI1499 | 1-21 | | 22-575 |
| SGA1 | A0A0H5C3I6 | *Cyberlindnera jadinii* (*Torula yeast*) (*Pichia jadinii*) | 1-16 | | 17-577 |
| GLA1 (AMYH_SACFI) ("Sf GA-3") | P26989 | *Saccharomycopsis fibuligera* (Hostinova et al. 2001) | 1-27 | | 28-519 |

TABLE 1-continued

Fungal Glucoamylases

| Name | Accession | Organism | Signal peptide | Pro-peptide | Chain |
|---|---|---|---|---|---|
| GLU1 AMYG_SACFI ("Sf GA-2") | P08017.1 | *Saccharomycopsis fibuligera* (Itoh et al. 1987) | 1-27 | | 28-519 |
| Glm ("Sf GA-1") | CAC83969 | *Saccharomycopsis fibuligera* IFO 0111 (Hostinova et al. 2003) | 1-26 | | 27-515 |

TABLE 2

Bacterial Glucoamylases

| Amylase gene | Accession | Organism | Signal peptide | Pro-peptide | Chain |
|---|---|---|---|---|---|
| SusB (SUSB_BACTN) | G8JZS4 | *Bacteroides thetaiotaomicron* (strain ATCC 29148/ DSM 2079/NCTC 10582/E50/VPI-5482) | 1-21 | | 22-738 |
| cga (AMYG_CLOS0) | P29761 | *Clostridium* sp. (strain G0005) | 1-21 | | 22-702 |

As noted herein and in Tables 1 and 2, glucoamylases enzymes from various fungal and bacterial species also generally include a native "signal sequence." Various other terms may be used to indicate a "signal sequence" as known in the art, such as where the word "signal" is replaced with "secretion" or "targeting" or "localization" or "transit" or "leader," and the word "sequence" is replaced with "peptide" or "signal." Generally, a signal sequence is a short amino acid stretch (typically in the range of 5-30 amino acids in length) that is located at the amino terminus of a newly synthesized protein. Most signal peptides include a basic N-terminal region (n-region), a central hydrophobic region (h-region) and a polar C-terminal region (c-region) (e.g., see von Heijne, G. (1986) Nucleic Acids Res. 14, 4683-4690). A signal sequence can target the protein to a certain part of the cell, or can target the protein for secretion from the cell. For example, it has been shown that the native N-terminal signal sequence of the *S. diastaticus* Glucoamylase STAI gene can target it to the endoplasmic reticulum of the secretory apparatus (for example, see Yamashita, I. et al., (1985) J. Bacteriol. 161, 567-573).

In one aspect, the current invention provides the partial or full replacement of the native signal sequence of a glucoamylase enzyme with the Sc MFα2 or Sc PHO5 secretion signal. In another aspect, the current invention provides addition of the Sc MFα2 or Sc PHO5 secretion signal to a glucoamylase enzyme, in addition to its native secretion signal. In view of the addition of the heterologous secretion signal, the proteins may be referred to as "fusion proteins," and annotated as follows: [Sc MFα2-SS]-[GA] and [Sc PHO5-SS]-[GA].

The *Saccharomyces cerevisiae* mating factor alpha 2 (Sc MFα2) secretion signal is described in U.S. Pat. No. 4,546,082 (Kurj an et al.). The Sc MFα2 SS sequence is as follows: MKFISTFLTFILAAVSVTA (SEQ ID NO. 10). The Sc MFα2 sequence is from the gene YGL089C (YGL089C), whereas MFα1 is coded by the gene YPL187W MFα1 and MFα2 are pheromones secreted by MATa cells. In one aspect, a glucoamylase fusion protein comprises a secretion signal sequence that has 90% or greater identity to SEQ ID NO: 10. For example, one amino acid of SEQ ID NO: 10 can be substituted with an amino acid, such as a conservative amino acid.

The *Saccharomyces cerevisiae* repressible acid phosphatase (Sc PHO5) secretion signal is described in U.S. Pat. No. 5,521,086 (Scott et al.) and Meyhack et al. (EMBO J. 6:675-680, 1982). The Sc PHO5 SS sequence is as follows: MFKSVVYSILAASLANA (SEQ ID NO. 11). The Sc PHO5 sequence is from PHO5 which is a structural gene that encodes a *S. cerevisiae* acid phosphatase, which is regulated by the concentration or inorganic phosphate ($P_i$) in the medium. In one aspect, a glucoamylase fusion protein comprises a secretion signal sequence that has 90% or greater identity to SEQ ID NO. 11. For example, one amino acid of SEQ ID NO. 11 can be substituted with an amino acid, such as a conservative amino acid.

Molecular techniques can be performed to create a nucleic acid sequence that is a template for the expression of the Sc MFα2 SS or the Sc PHO5 SS-glucoamylase gene (if the glucoamylase protein/nucleotide sequences are known in the art). As a general matter, a nucleic acid is prepared to encode a protein comprising the Sc PHO5 SS- or Sc MFα2 SS sequence and a glucoamylase sequence.

Any sequence encoding a functional glucoamylase polypeptide can be used. In some aspects, the glucoamylase sequence can be a native ("wild type") sequence of a glucoamylase gene, where the sequence of the glucoamylase portion of the Sc MFα2 SS or the Sc PHO5 SS-glucoamylase gene does not differ from the native sequence at any amino acid position. In other aspects, the sequence of the glucoamylase portion of the Sc MFα2 SS or the Sc PHO5 SS-glucoamylase gene differs from the native sequence at one or more amino acid position(s). The difference can be, for example, (a) the removal of one or more amino acids from the wild type sequence, (b) the addition of one or more amino acids to the wild type sequence, (c) the substitution of the wild type sequence, a combination of (a) and (c), or a combination of (b) and (c).

For example, in one aspect the native sequence of the glucoamylase can be altered at its N-terminus prior to adding the Sc MFα2 SS or the Sc PHO5 SS sequence. In some aspects, all or a portion of the native glucoamylase signal sequence is removed prior to attaching the Sc MFα2 SS or the Sc PHO5 SS sequence. For example, a portion of a native leader sequence of the glucoamylase can be altered by deletion of one or more, but not all, amino acids of the native secretion signal (e.g., deletion of up to 50%, 60%, 70%, 80, 90%, or 95% of the native leader sequence). Such deletion of a portion of the native leader sequence may cause the native glucoamylase leader to lose its native functionality, which is replaced with the functionality provided by the Sc MFα2 or Sc PHO5 secretion signal. In other aspects, all of the native secretion signal can be removed from the glucoamylase and replaced with the Sc MFα2 SS or the Sc PHO5 SS sequence.

For example, and with reference to Table 1, in preparing a fusion protein construct the first 18 amino acids of the *S. fibuligera* IFO 0111 glucoamylase (Sf GA-1), which corresponds to the predicted leader sequence using the CBS prediction server (i.e., amino acids 1-18 of SEQ ID NO:12), is removed. Therefore, a portion of the *S. fibuligera* glucoamylase native secretion signal is replaced with the Sc MFα2 SS sequence (SEQ ID NO:10; 19 amino acids) or with the Sc PHO5 SS sequence (SEQ ID NO:11; 17 amino acids) which can then be attached directly or indirectly to the remaining portion of the *S. fibuligera* glucoamylase polypeptide (e.g., amino acids 19-515 of SEQ ID NO:1). This provides a Sc MFα2 SS-Sf GA of 516 amino acids (SEQ ID NO:13) or a Sc PHO5 SS-Sf GA of 514 amino acids (SEQ ID NO:14).

As another example, one or more amino acids of a native leader sequence of the glucoamylase can be altered by substitution, which is the replacement of the native amino acid at a particular location in the native glucoamylase leader with an amino acid that is different than the native amino acid. For example, a portion of a native leader sequence of the glucoamylase can be altered by substitution of one or more amino acids of the native secretion signal (e.g., up to 50%, 60%, 70%, 80%, 90%, or 95% of the native leader sequence amino acids can be substituted). Substitution of one or more amino acids may cause the native glucoamylase leader to lose its native functionality, which is replaced with the functionality provided by the Sc MFα2 or Sc PHO5 secretion signal.

In other aspects, the fusion polypeptide comprising the Sc PHO5 SS- or Sc MFα2 SS sequence and a glucoamylase sequence optionally comprises additional sequence that is not present in the native glucoamylase polypeptide, or either Sc PHO5 SS- or Sc MFα2 SS sequence. The additional sequence can provide functionality to the secretion signal-modified glucoamylase that is not present in the native polypeptide. Additional functionalities include, for example, protease sites or binding sites for other proteins or materials.

An example of an additional sequence that may not be present in the native glucoamylase polypeptide, or either the Sc PHO5 SS- or Sc MFα2 SS sequences, but that can be added is a linker or spacer sequence. A linker sequence can be located between the Sc PHO5 SS- or Sc MFα2 SS sequence and the glucoamylase sequence. Such fusion polypeptides [secretion signal modified polypeptide] can be annotated as follows: [Sc MFα2-SS]-[L]-[GA] and [Sc PHO5-SS]-[L]-[GA], wherein "L" denotes one or more amino acids that link the signal sequence to the glucoamylase. Exemplary linkers include up to 5, 10, 15, 20, 25, 30, 35, or 40 amino acids. A linker can include amino acids that cause the linker to be rigid and prevent interactions between the secretion signal and other portions of the glucoamylase. Rigid linkers may include residues such as Pro, Arg, Phe, Thr, Glu, and Gln. Alternatively, the fusion polypeptide can include a flexible linker. Flexible linkers can include glycine residues and connect the signal sequence to the glucoamylase portion of the fusion protein without interfering with their respective functions. In some aspects the polypeptide includes a linker having a protease cleavage sequence. Exemplary protease cleavage sequences include those for thrombin, factor Xa, rhinovirus 3C, TEV protease, Ssp DnaB, intein, Sce VMA1 intein, enterokinase, and KEX2 (see, for example, Waugh, D. S., Protein Expr Purif. 80(2): 283-293, 2011; Zhou et al., Microbial Cell Factories 13:44, 2014; and Bourbonnais et al., J. Bio. Chem. 263(30):15342, 1988)

Another example of an additional sequence that may not be present in the native glucoamylase polypeptide, or either the Sc PHO5 SS- or Sc MFα2 SS sequences, but that can be added, is a tag sequence. A tag sequence can be located at the C-terminus of the glucoamylase sequence, and such proteins can be annotated as follows: [Sc MFα2-SS]-[GA]-[T] and [Sc PHO5-SS]-[GA]-[T], wherein "T" denotes one or more amino acids that provide the tag sequence. Exemplary peptide tags include up to 5, 10, 15, or 20 amino acids. The peptide tag can be useful for any one or more of a variety of purposes. For example, the tag can allow purification of the enzyme from the medium by the ability of a tag-binding member to specifically interact with the tag. The tag can also allow detection or identification of the protein using a tag-binding member with a detectable label. Exemplary short peptide tags are poly-Arg, FLAG, poly-His, c-myc, S, and Strep II.

Secretion signal modified polypeptides of the disclosure can also have deletions to one or more regions of the native glucoamylase polypeptide other than the native secretion sequence, wherein the deletions do not affect the polypeptides' amylolytic activity. The deletions can be based on known information regarding the structure and function of native glucoamylases, including mutational studies and sequence alignments (e.g., see Coutinho, supra, and Sierks, supra.). In some aspects the secretion signal modified polypeptides have up to 1%, up to 2%, up to 4%, up to 6%, up to 8%, up to 10%, up to 12%, up to 14%, up to 16%, up to 18%, up to 20%, or up to 25% of the glucoamylase polypeptide's sequence is deleted. In some aspects, the secretion signal modified polypeptides of the disclosure have a deletion of a portion of the C-terminus corresponding to the native glucoamylase polypeptide.

Truncated forms of glucoamylase have been generated and have been shown to have enzymatic activity. For example Evans et al. (Gene, 91:131; 1990) generated a series of truncated forms of glucoamylase to investigate how much of the O-glycosylated region was necessary for the activity or stability of GAII, a fully active form of the enzyme lacking the raw starch-binding domain. It was found that a significant portion of the C-terminus could be deleted from GAII with insignificant effect on activity, thermal stability, or secretion of the enzyme.

Various amino acids substitutions associated with causing a change in glucoamylase activity are also known in the art. Substitution(s) of amino acid(s) at various locations in the glucoamylase sequence have been shown to affect properties such as thermo stability, starch hydrolysis activity, substrate usage, and protease resistance. As such, the current disclosure contemplates use of the Sc MFα2 or Sc PHO5 secretion signal with a glucoamylase sequence that includes one or more amino acids substitution(s) in the glucoamylase portion of the polypeptide, wherein the substitutions differ from the wild type sequence of the glucoamylase.

For example, U.S. Pat. No. 8,809,023 describes a method for reducing the ratio between isomaltose synthesis and starch hydrolysis activity (IS/SH ratio) during the hydrolysis of starch. In particular a *Trichoderma reesei* glucoamylase (Tr GA) is described (total length of 632 amino acids having an N-terminal having a signal peptide) that is modified at with amino acid positions as follows: D44R and A539R; or D44R, N61I, and A539R. This glucoamylase variant is reported to exhibit a reduced IS/SH ratio compared to said parent glucoamylase during the hydrolysis of starch. As an example, the current disclosure contemplates the replacement of the native leader sequence of a desired glucoamylase (e.g., Sf GA with the Sc MFα2 or Sc PHO5 secretion signal, wherein the desired glucoamylase further has amino acid substitutions corresponding to the D44R and A539R; or D44R, N61I and A539R substitutions of the modified Tr GA. In a broader sense, the Sc MFα2 or Sc PHO5 secretion signal could be used with a glucoamylase variant having amino acid substitutions: D44R and A539R; or D44R, N61I and A539R, the positions corresponding to the respective position in the TrGA sequence, wherein said glucoamylase variant has at least 90% amino acid sequence identity to the entire length of the TrGA sequence. The corresponding "respective position" of a template glucoamylase sequence to the TrGA sequence can be understood by a sequence alignment of, for example, known glucoamylase polypeptide sequences (the template for construction of a Sc PHO5 SS- or Sc MFα2 SS glucoamylase fustion), to the TrGA sequence.

As another example, U.S. Pat. No. 8,592,194 describes glucoamylase variants with increased thermo stability compared to wild type glucoamylase variants. Also described in this disclosure is the *Trichoderma reesei* glucoamylase but instead one or more amino acid substitutions to the native Tr GA sequence at positions 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 236, 239, 240, 241, 242, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, and 418. As an example, the current disclosure contemplates the replacement of the native leader sequence of Sf GA with the Sc MFα2 or Sc PHO5 secretion signal, wherein the Sf GA further has any one or more of the amino acid substitutions that are demonstrated in providing increased thermostability. In a broader sense, the Sc MFα2 or Sc PHO5 secretion signal could be used with a glucoamylase variant having amino acid substitutions providing increased thermostability, the positions corresponding to the respective position in the TrGA sequence.

The determination of "corresponding" amino acids from two or more glucoamylases can be determined by alignments of all or portions of their amino acid sequences. Sequence alignment and generation of sequence identity include global alignments and local alignments, which typically use computational approaches. In order to provide global alignment, global optimization forcing sequence alignment spanning the entire length of all query sequences is used. By comparison, in local alignment, shorter regions of similarity within long sequences are identified.

As used herein, an "equivalent position" means a position that is common to the two sequences (e.g., a Sf GA sequence and a GA sequence having the desired substitution(s)) that is based on an alignment of the amino acid sequences of one glucoamylase or as alignment of the three-dimensional structures. Thus either sequence alignment or structural alignment, or both, may be used to determine equivalence.

In some modes of practice, the BLAST algorithm is used to compare and determine sequence similarity or identity. In addition, the presence or significance of gaps in the sequence which can be assigned a weight or score can be determined. These algorithms can also be used for determining nucleotide sequence similarity or identity. Parameters for to determine relatedness are computed based on art known methods for calculating statistical similarity and the significance of the match determined. Gene products that are related are expected to have a high similarity, such as greater than 50% sequence identity. Exemplary parameters for determining relatedness of two or more sequences using the BLAST algorithm can be as follows In some modes of practice, an alignment is performed using BLAST (National Center for Biological Information (NCBI) Basic Local Alignment Search Tool) version 2.2.29 software with default parameters. A sequence having an identity score of XX % (for example, 80%) with regard to a reference sequence using the BLAST version 2.2.29 algorithm with default parameters is considered to be at least XX % identical or, equivalently, have XX % sequence identity to the reference sequence. A global alignment can align sequences with significant identity to, for example, the *S. fibuligera* glucoamylase in order to determine which corresponding amino acid position(s) in the target sequence (e.g., a glucoamylase ortholog) can be substituted with the one or more of the amino acid if a glucoamylase variant is used.

Nucleic acids sequences encoding the Sc MFα2 SS or the Sc PHO5 SS-glucoamylase polypeptide, as well as any regulatory sequence (e.g., terminator, promoter, etc.) and vector sequence (e.g., including a selection marker, integration marker, replication sequence, etc.) can, in some modes of practice, be prepared using known molecular techniques. General guidance for methods for preparing DNA constructs (e.g., for the DNA constructs including the Sc MFα2 SS or the Sc PHO5 SS-glucoamylase gene) can be found in Sambrook et al Molecular Cloning, A Laboratory Manual, Cold Spring Harbor Laboratory Press, Cold Spring Harbor, N.Y., 1989; and Ausubel et al. Current Protocols in Molecular Biology, Greene Publishing and Wiley-Interscience, New York, N.Y., 1993.

When small amounts of glucoamylase template DNA are used as starting material in PCR, primers that include the MFα2 SS or the Sc PHO5 SS sequences and a portion of the glucoamylase sequence that is 3' to its native signal sequence can be used to generate relatively large quantities of a specific DNA fragment that includes the MFα2 SS or the Sc PHO5 SS sequences and the glucoamylase gene.

PCR techniques can be used for modifying a native glucoamylase nucleic acid sequence to add the Sc MFα2 SS or the Sc PHO5 SS sequences, or to introduce one or more mutations in the glucoamylase nucleic acid sequence to provide a variant. PCR techniques are described in, for example, Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. The techniques may optionally include site-directed (or oligonucleotide-mediated) mutagenesis, PCR mutagenesis, and cassette mutagenesis of an earlier prepared DNA encoding a glucoamylase polypeptide.

Alternatively, nucleic acid molecules can be generated by custom gene synthesis providers such as DNA2.0 (Menlo Park, Calif.) or GeneArt (Life Technologies, Thermo Fisher Scientific).

An expression vector can be constructed to include the Sc MFα2 SS or the Sc PHO5 SS-glucoamylase nucleic acid sequence operably linked to expression control sequences functional in the host organism. Expression vectors applicable for use in the host organisms include, for example, plasmids, episomes and artificial chromosomes. The vectors can include selection sequences or markers operable for stable integration into a host chromosome. Additionally, the vectors can include one or more selectable marker genes and appropriate expression control sequences. Selectable marker genes also can be included that, for example, provide resistance to antibiotics or toxins, complement auxotrophic deficiencies, or supply critical nutrients not in the culture medium. Expression control sequences can include constitutive and inducible promoters, transcription enhancers, transcription terminators, and the like which are well known in the art.

In some aspects, the nucleic acid can be codon optimized. The nucleic acid template that is used for the glucoamylase portion of the Sc MFα2 SS or the Sc PHO5 SS-glucoamylase can be the native DNA sequence that codes for the glucoamylase, or the template can be a codon-optimized version that is optimized for expression in a desired host cell. Databases that provide information on desired codon uses in particular host organisms are known in the art.

According to one aspect of the disclosure, a DNA construct comprising a Sc MFα2 SS or the Sc PHO5 SS-glucoamylase is operably linked to a promoter sequence, wherein the promoter sequence is functional in a host cell of choice. In some aspects, the promoter shows transcriptional activity in a fungal host cell and may be derived from genes encoding proteins either homologous or heterologous to the host cell. In some aspects the promoter is useful for expression in S. cerevisaie. Examples of well-known constitutive promoters include, but are not limited to the cytochrome c promoter (pCYC), translational elongation factor promoter (pTEF), the glyceraldehyde-3-phosphate dehydrogenase promoter (pGPD), the phosphoglycerate kinase promoter (PGK), and the alcohol dehydrogenase promoter (pADH). Optionally, an additional factor that controls expression such as an enhancer or the like may also be included on the vector.

The expression vector including the Sc MFα2 SS or the Sc PHO5 SS-glucoamylase gene can also include any termination sequence functional in the host cell. For example, the termination sequence and the promoter sequence can be from the same cell, or the termination sequence is homologous to the host cell. The termination sequence can correspond to any promoter that is used.

The DNA construct may be introduced into a host cell using a vector. The vector may be any vector which when introduced into a host cell is stably introduced. In some aspects, the vector is integrated into the host cell genome and is replicated. Vectors include cloning vectors, expression vectors, shuttle vectors, plasmids, phage particles, cassettes and the like. In some aspects, the vector is an expression vector that comprises regulatory sequences operably linked to the glucoamylase coding sequence.

The DNA construct comprising a Sc MFα2 SS or the Sc PHO5 SS-glucoamylase gene can further include a selectable marker, thereby facilitating the selection in a host cell.

For example, the selectable marker can be for transformed yeast. Examples of yeast selectable marker include markers commonly used for selecting for transformed yeast cells. Auxotrophic markers can be used using a gene that controls an auxotrophy, meaning that the gene enables yeast to produce a nutrient required for the growth of the yeast. Examples genes that control auxotrophies include leucine auxotrophy (LEU2), histidine auxotrophy (HIS3), uracil auxotrophy (URA3, URA5), and tryptophan auxotrophy (TRP1).

The DNA construct may be one which is integrated into the genome and replicated together with the chromosome(s) into which it has been integrated. For example, a fungal cell may be transformed with the DNA construct encoding the glucoamylase, and integrating the DNA construct, in one or more copies, in the host chromosome(s). This integration is generally considered to be an advantage, as the DNA sequence is more likely to be stably maintained. Integration of the DNA constructs into the host chromosome may be performed according to conventional methods, such as by homologous or heterologous recombination.

The non-natural yeast can also include one or other genetic modifications that are different than the modification of the glucoamylase with heterologous signal sequence. For example, one or more additional modifications can include those that provide a different polysaccharide-degrading enzyme, such as an exogenous or modified alpha-amylase, beta-amylase, pullulanase, isoamylase, or cyclodextrin glycosyltransferases; an exogenous or modified sugar transporter gene (such as an isomaltose transporter); and/or an exogenous or modified gene that converts a low molecular weight non-glucose sugar to glucose, such as an isomaltase.

Various host cells can be transformed with a nucleic acid including the Sc MFα2 SS or the Sc PHO5 SS-glucoamylase gene. In some aspects the nucleic acid including the Sc MFα2 SS or the Sc PHO5 SS-glucoamylase gene is present in a bacterial cell. The bacterial cell can be used, for example, for propagation of the nucleic acid sequence or for production of quantities of the polypeptide.

In other aspects, the host cell is a eukaryotic cell, such as a fungal cell.

In some aspects the host cell is has tolerance to a higher amount of a bioderived product, such as ethanol, in the fermentation medium. In some aspects, the host cell is an "industrial yeast" which refers to any yeasts used conventionally in ethanol fermentation. Examples include sake yeasts, shochu yeasts, wine yeasts, beer yeasts, baker's yeasts, and the like. Sake yeasts demonstrate high ethanol fermentability and high ethanol resistance and genetic stability. Typically, an industrial yeast has high ethanol resistance and preferably is viable at ethanol concentrations of 10% or greater.

In exemplary aspects, the host cell is S. cerevisiae. Some S. cerevisiae have high tolerance to ethanol. Various strains of ethanol tolerant yeast are commercially available, such as RED STAR® and ETHANOL RED® yeast (Fermentis/Lesaffre, USA), FALI (Fleischmann's Yeast, USA), SUPERSTART and THERMOSACC® yeast (Ethanol Technology, Wis., USA), BIOFERM AFT and XR (NABC—North American Bioproducts Corporation, GA, USA), GERT STRAND (Gert Strand AB, Sweden), and FERMIOL (DSM Specialties).

Industrial yeasts are typically prototrophic and therefore do not have an auxotrophic marker suitable for selecting for a transformant. If the host cell does not have the genetic background that would otherwise facilitate retention of the Sc MFα2 SS or the Sc PHO5 SS-glucoamylase gene within the cell upon transformation, the host cell can be engineered to introduce one or more genetic mutation(s) to establish use of a marker gene in association with and to maintain the Sc MFα2 SS or the Sc PHO5 SS-glucoamylase gene in the cell. For example, a commercially available ethanol tolerant yeast cell can be genetically modified prior to introducing the Sc MFα2 SS or the Sc PHO5 SS-glucoamylase gene in the cell.

A marker for a different auxotrophy can be provided by disrupting the gene that controls the auxotrophy. In one mode of practice, an ethanol tolerant strain of yeast is engineered to disrupt copies of one or more genes that control auxotrophies, such as LEU2, HIS3, URA3, URA5, and TRP1. In the case of providing uracil auxotrophy, for example, a normal ura3 gene of an ethanol tolerant yeast can be replaced with an ura3⁻ fragment obtained from a uracil auxotrophic mutant (for example, a *Saccharomyces cervisiae* MT-8 strain) to disrupt the normal ura3 gene. In the case of a ura3 gene-disrupted strain, the presence/absence of a marker can be easily identified or selected by taking advantage of the fact that a ura3 gene-disrupted strain is able to grow in a medium containing 5-fluoroorotic acid (5-FOA) while a normal ura3 strain (wild-type yeast or usual industrial yeast) is not able to grow. In the case of a lys2 gene-disrupted strain, the presence/absence of a marker can be easily identified or selected by taking advantage of the fact that a lys2 gene-disrupted strain is able to grow in a medium containing α-aminoadipic acid while a normal lys2 strain (wild-type yeast or usual industrial yeast) is not able to grow. Methods for disrupting an auxotrophy-controlling gene and for selectively separating auxotrophy-controlling gene mutants may be used depending on the auxotrophy employed. Alternatively, one can employ dominant selection markers, such as the amdS from *Aspergillus nidulans* (U.S. Pat. No. 5,876,988), which allows for growth on acetamide as the sole nitrogen source; or ARO4-OFP, which allows for growth in the presence of fluoro-phenylalanine (Fukuda et. al.). These markers can be used repeatedly using the recyclable cre-loxP system, or alternatively can be used to create auxotrophic strains that allow additional markers to be utilized.

After the host cell has been engineered to provide a desired genetic background for introduction of the Sc MFα2 SS or the Sc PHO5 SS-glucoamylase gene, the gene construct is introduced into a cell to allow for expression. Methods for introducing a gene construct into a host cell include transformation, transduction, transfection, co-transfection, electroporation. In particular, yeast transformation can be carried out suing the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein.

The transformation of exogenous nucleic acid sequences including the Sc MFα2 SS or the Sc PHO5 SS-glucoamylase gene can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The non-natural yeast of the disclosure can be provided in any suitable form. In some aspects, the non-natural yeast is dehydrated to form a dry yeast composition. The dry yeast composition can have increased shelf life over wet compositions.

Fermentation using a host cell expressing the Sc MFα2 SS or the Sc PHO5 SS-glucoamylase gene can be performed in the presence of a starch and/or sugar containing plant material, referring to a starch and/or sugar containing plant material derivable from any plant and plant part, such as tubers, roots, stems, leaves and seeds. Starch and/or sugar comprising plant material can be obtained from cereal, such as barley, wheat, maize, rye, sorghum, millet, barley, potatoes, cassava, or rice, and any combination thereof. The starch- and/or sugar comprising plant material can be processed, such as by methods such as milling, malting, or partially malting. In some aspects, the starch material is from corn flour, milled corn endosperm, sorghum flour, soybean flour, wheat flour, biomass derived starch, barley flour, and combinations thereof.

In some aspects, the fermentation medium includes a treated starch. For example, the fermentation medium can include a partially hydrolyzed starch. The partially hydrolyzed starch can include high molecular weight dextrins and high molecular weight maltodextrins. In some modes of practice, a partially hydrolyzed starch product having a dextrose equivalent ("DE") in the range of about 5 to about 95 or more preferably about 45 to about 65, is used in the fermentation medium. Partially hydrolyzed starches and preparation thereof are well known in the art. Partially hydrolyzed starches can be prepared by heating the starch with an acid such as hydrochloric or sulfuric acid at a high temperature and then neutralizing the hydrolysis mixture with a suitable base such as sodium carbonate. Alternatively, partially hydrolyzed starches can be prepared by an enzymatic process, such as by adding alpha-amylase to a starch preparation. An alpha amylase can cause the endohydrolysis of (1→4)-alpha-D-glucosidic linkages in polysaccharides containing three or more (1→4)-alpha-linked D-glucose units. A partially hydrolyzed starch product can be used that have amounts of starch and starch degradation products within desired ranges.

In aspects of the disclosure, given production and secretion of the glucoamylase from the engineered yeast into the fermentation medium, the fermentation method may omit addition of purified or enriched commercial glucoamylase into the medium, or at least allow significantly less commercial glucoamylase to be used in a fermentation method. For example, the engineered yeast of the disclosure can allow addition of commercial glucoamylase to be eliminated or at least reduced by about 50%, 60%, 70%, 80%, 90%, or 95%. Typically amounts of glucoamylase in the range of about 7 units to about 50 units per liter would be used in fermentation methods that do not use a glucoamylase-secreting engineered yeast.

The fermentation broth includes water and preferably includes nutrients, such as a nitrogen source (such as proteins), vitamins and salts. A buffering agent can also be present in the fermentation medium. Other components may also be present in the fermentation broth after a period of fermentation, such as fermentation products which can accumulate as the fermentation progresses, and other metabolites. Optionally, the fermentation broth can be buffered with a base such as calcium hydroxide or calcium carbonate, ammonia or ammonium hydroxide, sodium hydroxide, or potassium hydroxide in order to maintain a pH at which the organism functions well.

The engineered yeast of the current disclosure can also be described in terms of the engineered yeast's specific growth rate. Specific growth rate is measured in units of hours$^{-1}$ measured using techniques known in the art.

The fermentation is carried out under conditions so that fermentation can occur. Although conditions can vary depending on the particular organism and desired fermentation product, typical conditions include a temperature of about 20° C. or greater, and more typically in the range of about 30° C. to about 50° C. During fermentation the reaction mixture can be mixed or agitated. In some modes of practice, the mixing or agitation can occur by the mechanical action of sparging gas to the fermentation broth. Alternatively direct mechanical agitation such as by an impellor or by other means can be used during fermentation.

The non-natural yeast can have an increased tolerance to growth at temperatures that greater than those in which yeast, such *Saccharomyces cerevisiae*, typically grow at. For example, *S. cerevisiae* typically have optimal growth in the temperature range of 30° C.-33° C. In some aspects, the non-natural yeast of the disclosure display improved tolerance to growth at temperatures in the range of 34° C.-40° C.

For example, as compared to reference yeast without the genetic modification, the non-natural yeast of the disclosure can have a specific growth rate at a temperature in the range of 34° C.-40° C., that is 10%, 20%, 30%, 40%, or 50% greater than the growth rate of a reference yeast without the genetic modification.

In some cases fermentation is carried out in industrial capacity fermenters in order to achieve commercial scale economic benefits and control. In an aspect, the fermentation is carried out in a fermenter that has a capacity of about 10,000 liters or more.

The pH of the fermentation medium can be adjusted to provide optimal conditions for glucoamylase activity, cell growth, and fermentation activity to provide a desired product, such as ethanol. For example, pH of the solution can be adjusted to in the range of 3 to 5.5. In one mode of practice, the pH of the fermentation medium is in the range of 4 to 4.5.

As noted above, the present fermentation process using genetically modified microorganisms expressing the Sc MFα2 SS or the Sc PHO5 SS-glucoamylase gene and capable of secreting the enzyme produced into the fermentation medium. These enzymes are therefore directly exposed to the broth conditions and affect the carbohydrate composition in the fermentation medium. In the fermentation medium the glucoamylase can cause hydrolysis and release of D-glucose from the non-reducing ends of the starch or related oligo- and polysaccharide molecules by cleaving alpha-(1,4) and alpha-(1,6) glucosidic bonds.

Starch may also be acted on by one or more other amylases (e.g., alpha-amylase) present in the fermentation medium. For example, if alpha-amylase is present in the fermentation medium it can cause partial hydrolysis of precursor starch and cause a partial breakdown of the starch molecules by hydrolyzing internal alpha-(1,4)-linkages.

In some modes of practice, the fermentation is carried out as a single batch until completion.

In other modes of practice, the fermentation is carried out as a fed batch fermentation process. In this mode of practice, a first portion of a total amount of starch material to be fermented is added to the fermentation medium wherein the glucoamylase enzyme acts on the starch to cause formation of glucose to be used as a substrate for fermentation. Additional starch material is added in one or more portions to provide more substrate for the glucoamylase enzyme in the medium. The addition of starch can be regulated and the formation of glucose can be monitored to provide efficient fermentation.

Preferably, the fermentation is carried out in a continuous mode of operation. In this mode, multiple fermenters operate in series in which a starch hydrolysate is supplied in the first fermenter, which is fed to second fermenter and so on until the starch hydrolysate is converted to ethanol. Continuous operation can be operated using between 2-7 fermenters.

In some modes of practice, a portion of the total amount of starch material is added to the fermentation broth using a variable rate addition system. Examples of such systems include a variable speed pump or a metering valve (such as a throttle valve) operably connected to a pump, which pump or valve can be utilized to vary the amount of starch material introduced into the fermentation broth over time. In an some modes of practice, during the addition of a portion of the starch material, glucose concentration is monitored by a real-time monitoring system.

Real-time monitoring systems include systems that directly monitor glucose concentration and systems that indirectly monitor glucose concentration. Examples of real-time monitoring systems that typically directly monitor glucose concentration include systems based on infrared (IR) spectroscopy, near-infrared (NIR) spectroscopy systems, Fourier transform infrared (FTIR) systems, systems based on refractive index, automated enzyme based measurement systems such as a YSI 2950 Biochemistry Analyzer sold by YSI Life Sciences systems, high performance liquid chromatography (HPLC) based systems, gas chromatography (GC) based systems, and other real-time monitoring systems known to one of skill in the art. Additionally real-time monitoring systems that indirectly monitor/measure the glucose concentration of a fermentation process can be developed by determining the typical carbon distribution in a particular fermentation process and correlating the glucose concentration present in the fermentation broth to another parameter exhibited by the fermentation, such as, for example, a correlation of the glucose level present in the fermentation broth with a measurement of the carbon dioxide evolution rate and the amount of carbon dioxide present in an off-gas stream from the fermentation vessel. The carbon dioxide can be readily measured through use of a mass spectrometer or other suitable instrumental technique for measuring the components of the off-gas stream. In a preferred aspect, the glucose concentration is monitored by a real-time monitoring system using infrared spectroscopy. In another one aspect, the glucose concentration is monitored by a real-time monitoring system using near-infrared spectroscopy. The real time monitoring systems interface with equipment that controls the introduction of starch material into the fermentation broth to modulate the formation of glucose to a desired concentration in the fermentation broth.

During the fermentation process a sample of the fermentation medium can be taken to determine the amount of glucoamylase activity in the medium. The amount of glucoamylase activity in the medium can be referred to as extracellular glucoamylase activity as it corresponds to glucoamylase secreted from the engineered yeast. In some modes of measuring, the amount of glucoamylase activity in the medium can be determined by the amount of glucoamylase activity per amount of biomass per volume of medium.

As used herein "biomass" refers to the weight of the engineered yeast, which can be measured in grams of dried cell weight per liter of medium (DCW/L).

A unit (U) of GA activity can be defined as the amount of enzyme that catalyzes the release of 1 mg glucose/min from starch. Glucoamylase activity can be measured in concentrated broth by coupling starch hydrolysis to a HXK/G6PDH reaction mix (Sigma G3293) in a two-step end point assay. Broth can be concentrated from a predetermined amount of cells grown using a non-glucose carbon source (i.e. raffinose) to avoid interference with the assay.

The specific activity is equal to the activity in a given volume of broth divided by the wet weight of cells in the same volume of broth. Specific activity has the following units, U of GA activity per gram of biomass (U/g biomass). The amount of biomass used in the assay can be measured by determining the wet cell weight after removing the broth, either by filtration or centrifugation.

A starch solution is prepared by dissolving 1.1 g of corn starch (S4126, Sigma) in 50 mL of near boiling water, then adding 1 mL of 3M sodium acetate pH 5.2. A volume of concentrated broth ($V_b$), typically in the range of 1-20 ul (prepared by using a 10 Kb Kd cutoff column, Millipore # UFC901008) is added to the starch slurry ($V_s$), in a total volume of 200 ul, and allowed to incubate at 37° C. for a specific period of time (T), typically between 5-60 minutes. Parameters are selected such that the glucose formation is linear within a desired time. 20 μL of each sample is added to 2 μL 0.6N NaOH and mixed well. 200 μL of the HXK/G6PDH mix is then added and incubated at 30° C. for 30 minutes. The absorbance at 340 nm is measured using a spectrophotometer (SpectraMax™ M2). Regression analysis using known glucose standards is used to calculate the amount of glucose released in each sample. The specific enzyme activity per gram of biomass (U/g biomass) can be calculated by obtaining the weight in grams of the sample used prior to concentration. Unit of activity=(mg glucose/T)*(($V_b+V_s$)/($V_b$))*(222/20). Specific activity=Unit of activity/g biomass.

In some aspects, in the fermentation method the medium has an amount of glucoamylase activity of 2.25 U or greater per gram of biomass. In some aspects the medium has an amount of glucoamylase activity of about 2.3 U or greater, about 2.35 U or greater, about 2.4 U or greater, about 2.45 U or greater, about 2.5 U or greater, about 2.6 U or greater, about 2.7 U or greater, about 2.8 U or greater, about 2.9 U or greater, about 3 U or greater, about 3.5 U or greater, about 4 U or greater, about 4.5 U or greater, about 5 U or greater, about 5.5 U or greater, about 6 U or greater, about 6.5 U or greater, about 7 U or greater, about 7.5 U or greater, or about 8 U or greater per gram of biomass. In some aspects the medium has an amount of glucoamylase activity in the range of about 2.3 U to about 15 U, about 2.4 U to about 15 U, about 2.5 U to about 15 U, about 3 U to about 15 U, about 3.5 U to about 15 U, about 4 U to about 15 U, about 4.5 U to about 15 U, about 5 U to about 15 U, about 5.5 U to about 15 U, about 6 U to about 15 U, about 6.5 U to about 15 U, about 7 U to about 15 U, about 7.5 U to about 15 U, or about 8 U to about 15 U per gram of biomass.

In other aspects, an amount of glucoamylase activity in a fermentation medium provided by a non-natural yeast of the disclosure can be described relative to a reference yeast. For example, the amount of glucoamylase activity that a non-natural yeast expressing an exogenous glucoamylase having a heterologous signal sequence (e.g., having 90% or greater identity to SEQ ID NO:10 or SEQ ID NO:11) can be compared to an otherwise identical yeast expressing the exogenous glucoamylase with its native signal sequence.

In some aspects, the non-natural yeast expressing an exogenous glucoamylase having a heterologous signal sequence provides an amount of glucoamylase activity in the fermentation medium that is at least 1.125 times greater (12.5% greater) than a reference yeast. In some aspects the amount of glucoamylase activity is at least 1.15 times greater, at least 1.175 times greater, at least 1.225 times greater, at least 1.25 times greater, at least 1.3 times greater, at least 1.35 times greater, at least 1.4 times greater, at least 1.45 times greater, at least 1.5 times greater, at least 1.75 times greater, at least 2 times greater, at least 2.25 times greater, at least 2.5 times greater, at least 2.75 times greater, at least 3 times greater, at least 3.25 times greater, at least 3.5 times greater, at least 3.75 times greater, or at least 4 times greater in the non-natural yeast over the reference yeast. In some aspects the glucoamylase activity provided by non-natural yeast over the reference yeast in an amount in the range of about 1.15 to about 7.5 times greater, about 1.175 to about 7.5 times greater, about 1.225 to about 7.5 times greater, about 1.25 to about 7.5 times greater, about 1.3 to about 7.5 times greater, about 1.35 to about 7.5 times greater, about 1.4 to about 7.5 times greater, about 1.45 to about 7.5 times greater, about 1.5 to about 7.5 times greater, about 1.75 to about 7.5 times greater, about 2 to about 7.5 times greater, about 2.25 to about 7.5 times greater, about 2.5 to about 7.5 times greater, about 2.75 to about 7.5 times greater, about 3 to about 7.5 times greater, about 3.25 to about 7.5 times greater, about 3.5 to about 7.5 times greater, about 3.75 to about 7.5 times greater, or about 4 to about 7.5 times greater in the non-natural yeast over the reference yeast.

Measurement of glucoamylase activity in the fermentation medium can be performed at a desired time point during fermentation. For example, a sample from the fermentation media can be taken about $\frac{1}{10}^{th}$, about $\frac{2}{10}^{th}$, about $\frac{3}{10}^{th}$, about $\frac{4}{10}^{th}$, about $\frac{5}{10}^{th}$, about $\frac{6}{10}^{th}$, about $\frac{7}{10}^{th}$, about $\frac{8}{10}^{th}$, about $\frac{9}{10}^{th}$ of the way through the fermentation process, or at the end of the fermentation process, and the sample can be tested for glucoamylase activity.

In some modes of practice, the fermentation period is about 30 hours or greater, about 40 hours or greater, about 50 hours or greater, or about 60 hours or greater, such as a period of time in the range of about 40 to about 120 hours, or 50 to about 110 hours.

The fermentation product (also referred to herein as a "bio-derived product" or "bioproduct") can be any product that can be prepared by enzymatic degradation of a starch material by the glucoamylase, formation of glucose, and fermentation of glucose. In aspects, In an embodiment, the fermentation product is selected from the group consisting of: amino acids, organic acids, alcohols, diols, polyols, fatty acids, fatty acid alkyl esters (such as fatty acid methyl or ethyl esters (for example C6 to C12 fatty acid methyl esters (preferably C8 to C10 fatty acid methyl esters))), monacyl glycerides, diacyl glycerides, triacyl glycerides, and mixtures thereof. Preferred fermentation products are organic acids, amino acids, fatty acid alkyl esters (such as fatty acid methyl esters (for example C8 to C12 fatty acid methyl esters (preferably C8 to C10 fatty acid methyl esters))), and their salts thereof, and especially where the organic acid is selected from the group consisting of hydroxyl carboxylic acids (including mono-hydroxy and di-hydroxy mono-, di-, and tri-carboxylic acids), monocarboxylic acids, dicarboxylic acids, and tricarboxylic acids and mixtures thereof. Examples of fermentation products that are prepared by the present process are organic acids or amino acids such as lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, acetic acid, methyl hexanoate, methyl octanoate, methyl nonanoate, methyl decanoate, methyl dodecanoate, ethyl hexanoate, ethyl octanoate, ethyl nonanoate, ethyl decanoate, ethyl dodecanoate, and mixtures thereof and derivatives thereof and salts thereof. In a preferred aspect, a fermentation method of the disclosure produces ethanol as the bioproduct.

The fermentation product is recovered from the fermentation broth. The manner of accomplishing this will depend on the particular product. However, in some modes of practice, the organism is separated from the liquid phase, typically via a filtration step or centrifugation step, and the product recovered via, for example, distillation, extraction, crystallization, membrane separation, osmosis, reverse osmosis, or other suitable technique.

The present process provides the ability to make fermentation products on a production scale level with excellent yields and purity. In an aspect, the process is carried out in fermentation broth quantities of at least 25,000 gallons. In an aspect, the batch process is carried out in to produce batches of at least 25,000 gallons of final fermentation broth. Add continuous process, vessels of at least 200,000 gallons.

A composition comprising a Sc MFα2 SS or the Sc PHO5 SS-glucoamylase can optionally be used in combination with any one or in any combination with the following enzymes that are different than the glucoamylase. Exemplary other enzymes include alpha amylases, beta-amylases, peptidases (proteases, proteinases, endopeptidases, exopeptidases), pullulanases, isoamylases, cellulases, hemicellulases, endo-glucanases and related beta-glucan hydrolytic accessory enzymes, xylanases and xylanase accessory enzymes, acetolactate decarboxylases, cyclodextrin glycotransferases, lipases, phytases, laccases, oxidases, esterases, cutinases, granular starch hydrolyzing enzymes and other glucoamylases.

In some aspects, a Sc MFα2 SS or the Sc PHO5 SS-glucoamylase can be used for starch conversion processes, such as for the production of dextrose for fructose syrups, specialty sugars and in alcohol and other end-product (e.g., organic acid, ascorbic acid, and amino acids). Production of alcohol from the fermentation of starch substrates using glucoamylases of the disclosure can include the production of fuel alcohol or potable alcohol.

The production of alcohol can be greater when a Sc MFα2 SS or the Sc PHO5 SS-glucoamylase of used under the same conditions as compared to the parent or wild-type glucoamylase. For example, the increase in alcohol production using the glucoamylases of the disclosure can be 1.1× or greater, 1.2× or greater, 1.3× or greater, 1.4× or greater, 1.5× or greater, 1.6× or greater, 1.7× or greater, 1.7× or greater, 1.8× or greater, 1.9× or greater, 2.0× or greater, 2.1× or greater, 2.2× or greater, 2.3× or greater, 2.4× or greater, or 2.5× or greater that alcohol production in a wild type strain.

In some aspects, the disclosure provides a method for producing ethanol by fermentation, wherein the ethanol is present in the fermentation medium at a concentration of 90 g/L or greater. In the method, a liquid medium comprising a starch material and a non-natural yeast comprising a exogenous nucleic acid encoding polypeptide comprising a glucoamylase portion and a signal sequence heterologous to the glucoamylase is fermented. Fermentation can provide an ethanol concentration of about 90 g/L or greater in the liquid medium, such as in the range of about 90 g/L to about 170 g/L, in the range of about 110 g/L to about 170 g/L, in the range of about 125 g/L to about 170 g/L, or in. in the range of about 140 g/L to about 170 g/L.

The method includes fermenting a liquid medium comprising a starch material and a non-natural yeast comprising a exogenous nucleic acid encoding polypeptide comprising a glucoamylase portion and a signal sequence heterologous to the glucoamylase, wherein said fermenting provides an ethanol concentration of 90 g/L or greater in the liquid medium.

Use of the non-natural yeast of the current disclosure may also provide benefits with regards to increased titers, reduced volatile organic acids (VOCs), and reduced fusel oil compounds (volatile organic acids, higher alcohols, aldehydes, ketones, fatty acids and esters).

The fermentation product may be first treated with one or more agents a treatment system. The treated fermentation product can then be sent to a distillation system. In the distillation system, the fermentation product can be distilled and dehydrated into ethanol. In some aspects, the components removed from the fermentation medium include water, soluble components, oil and unfermented solids. Some of these components can be used for other purposes, such as for an animal feed product. Other co-products, for example, syrup can be recovered from the stillage.

The present disclosure also provides a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a composition as described herein. In another aspect, the invention also relates to a kit comprising a glucoamylase of the current disclosure, or a composition as contemplated herein; and instructions for use of said glucoamylase or composition. The invention also relates to a fermented beverage produced by a method using the glucoamylase.

After the fermentation process is complete, materials present in the fermentation medium can be of use. In some aspects, after a fermentation process has been completed, or while a fermentation process is ongoing, some or all of a bioproduct can be removed from the fermentation medium to provide a refined composition comprising non-bioproduct solids. The non-bioproduct solids the non-natural yeast, feedstock material in the medium that is not utilized by the yeast, as well as fermentation co-products. These materials can provide sources of carbohydrates and proteins that are useful as supplements to improve the nutritional content of a feed composition. The feed material can be a co-product from a fermentation process such as stillage (whole stillage, thin stillage, etc.) or composition prepared therefrom including dried distillers grains (DDG), distillers dry grains with solubles (DDGS), distillers wet grains (DWG), and distillers solubles (DS).

A fermentation medium, optionally with some or all of the target bioproduct removed, can be further treated, such as to remove water, or to cause precipitation or isolation of the non-bioproduct solids from the medium. In some cases the medium is treated by freeze drying or oven drying. After treatment the refined composition may be in the form of, for example, a liquid concentrate, a semi-wet cake, or a dry solid. The refined composition can be used as a feed composition itself, or an ingredient in the preparation of a feed composition. In preferred preparations, the feed composition is a livestock feed composition such as for sheep, cattle, pigs, etc.

The solids in the fermentation medium can provide a source of one or more amino acids. Introduced into an animal feed, the fermentation co-product can provide an enhanced amino acid content with regard to one or more essential amino acids. Essential amino acids can include histidine, isoleucine, lysine, methionine, phenylalanine, threonine, and tryptophan. These amino acids can be present in the feed composition as free amino acids or can be derived from proteins or peptides rich in the amino acids. The solids in the fermentation medium can provide a source of one prebiotics, which are nondigestible food substances, such as nondigestible oligosaccharides, that selectively stimulate the growth of favorable species of bacteria in the gut, thereby benefiting the host. The solids in the fermentation medium can provide a source of phytases, β-glucanases, proteases, and xylanases.

The feed composition can be used in aquaculture, is the farming of aquatic organisms such as fish, shellfish, or plants. Aquaculture includes the cultivation of both marine and freshwater species and can range from land-based to open-ocean production.

A feed composition, in addition to material obtained from the fermentation media, can include one or more feed additives. Feed additives can be used, for example, to help provide a balanced diet (e.g., vitamins and/or trace minerals), to protect the animals from disease and/or stress (e.g., antibiotics, probiotics) and/or to stimulate or control growth and behavior (e.g., hormones). Additive product ingredients may include, for example: growth promoters, medicinal substances, buffers, antioxidants, enzymes, preservatives, pellet-binding agents, direct-fed microbials, etc. Additive product ingredients may also include, for example, ionophores (e.g. monesin, lasalocid, laidlomycin, etc.), β-agonist (zilpaterol, ractompamine, etc.), antibiotics (e.g., chlortetracycline (CTC), oxytetracycline, bacitrain, tylosin, aureomycin), probiotics and yeast cultures, coccidiostats (e.g., amprollium, decoquinate, lasalocid, monensin), and hormones (e.g., growth hormones or hormones that inhibit estrus and/or ovulation such as melengestrol acetate), pheromones, nutraceuticals, pharmaceuticals, flavanoids, nutritive and non-nutritive supplements, detoxicants, etc. Some commercially available additives are sold under the trade names Rumensin®, Bovatec®, Deccox®, Tylan®, Optaflexx®, and MGA®.

Example 1

Generation of Amylolytic *Saccharomyces cerevisiae* Strains

Strain 1-3: ura3Δ *Saccharomyces cerevisiae* Base Strain

Strain 1 is transformed with SEQ ID NO 1 (pAV18). SEQ ID NO 1 contains the following elements: i) an expression cassette for a mutant version of a 3-deoxy-D-arabino-heptulosonate-7-phosphate (DAHP) synthase gene from *Saccharomyces cerevisiae* (ARO4-DFP) corresponding to nucleotides 479-2647; ii) loxP sequence corresponding to nucleotides 445-478 and 2648-2681, and iii) flanking DNA for targeted chromosomal integration into integration locus A (URA3) where nucleotides 1-436 correspond to the URA3 5' flanking region and nucleotides 2691-3182 correspond to the URA3 3' flanking region. Transformants are selected on synthetic complete medium containing 3.5 g/L of p-fluorophenylalanine, and 1 g/L L-tyrosine (ScD-PFP). Resulting transformants are streaked for single colony isolation on ScD-PFP. A single colony is selected. Correct integration of SEQ ID NO: 1 into one allele of locus A is verified by PCR in the single colony. A PCR verified isolate is designated Strain 1-1.

Strain 1-1 is transformed with SEQ ID NO 2 (pCM520a). SEQ ID NO 2 contains the following elements: i) a codon optimized expression cassette for a acetamidase (amdS) gene from *Aspergillus nidulans* corresponding to nucleotides 638-2284 with a TEF1 promoter corresponding to nucleotides 2285-2740 and a TEF1 terminator corresponding to nucleotides 478-637; ii) loxP sequence corresponding to nucleotides 444-477 and 2741-2774, and iii) flanking DNA for targeted chromosomal integration into integration locus A (URA3) where nucleotides 1-435 correspond to the URA3 5' flanking region and nucleotides 2783-3275 correspond to the URA3 3' flanking region. Transformants are selected on Yeast Nitrogen Base (without ammonium sulfate or amino acids) containing 80 mg/L uracil and 1 g/L acetamide as the sole nitrogen source. Resulting transformants are streaked for single colony isolation on Yeast Nitrogen Base (without ammonium sulfate or amino acids) containing 80 mg/L uracil and 1 g/L acetamide as the sole nitrogen source. A single colony is selected. Correct integration of SEQ ID NO 2 into the second allele of locus A is verified by PCR in the single colony. A PCR verified isolate is designated Strain 1-2.

Strain 1-2 is co-transformed with SEQ ID NO 3 and SEQ ID NO 4. SEQ ID NO 3 contains the following elements: i) an open reading frame for a cre recombinase from P1 bacteriophage corresponding to nucleotides 53-1084, and ii) flanking DNA homologous to SEQ ID NO 4 corresponding to nucleotides 1-47 and 1086-1132. SEQ ID NO 4 contains the following elements: i) a 2μ origin of replication corresponding to nucleotides 2195-3350; ii) a URA3 selectable marker from *Saccharomyces cerevisiae* corresponding to nucleotides 3785-4901; and iii) flanking DNA containing a PGK promoter corresponding to nucleotides 5791-6376 and CYC1 terminator corresponding to nucleotides 10-199 from *Saccharomyces cerevisiae*. For the remaining part of SEQ ID NO 4, a pUC origin of replication corresponds to nucleotides 386-1053; and an ampicillin resistance gene corresponds to nucleotides 1204-2061. Transformants are selected on synthetic dropout medium lacking uracil (ScD-Ura). ScD-Ura agar plates contain: 20 g/L agar, 6.7 g/L Yeast Nitrogen Base, 2 g Synthetic complete drop-out mix lacking uracil, and 20 g/L dextrose. Resulting transformants are streaked for single colony isolation on ScD-Ura. A single colony is selected. The isolated colony is screened for growth on ScD-PFP and Yeast Nitrogen Base (without ammonium sulfate or amino acids) containing 80 mg/L uracil and 1 g/L acetamide as the sole nitrogen source. Loss of the ARO4-OFP and amdS genes is verified by PCR. The PCR verified isolate is streaked to YNB containing 5-FOA to select for loss of the 2μ plasmid. The PCR verified isolate is designated Strain 1-3.

Strain 1-4: *Saccharomyces cerevisiae* Expressing *Saccharomycopsis fibuligera* Glucoamylase Strain 1-3 is transformed with SEQ ID NO 5. SEQ ID NO 5 contains the following elements: 1) an expression cassette for a glucoamylase gene from *Saccharomycopsis fibuligera* corresponding to nucleotides 2769-4316, including an ADH1 promoter corresponding to nucleotides 2022-2768 and a CYC1 terminator corresponding to nucleotides 4318-4540, 2) a centromere to allow for stable replication corresponding to nucleotides 6798-7316, and 3) an expression cassette for an orotidine-5'-phosphate decarboxylase (URA3) corresponding to nucleotides 195-1292. Transformants are selected on ScD-Ura. Resulting transformants are streaked for single colony isolation on ScD-Ura. A single colony is selected. Presence of the plasmid is verified by PCR. The PCR verified isolate is designated Strain 1-4a, b, c, Strain 1-5: *Saccharomyces cerevisiae* Expressing a Modified *Saccharomycopsis fibuligera* Glucoamylase Containing an N-Terminal Secretion Leader from Alpha Mating Factor 1 (MFα1)

Strain 1-3 is transformed with SEQ ID NO 6. SEQ ID NO 6 contains the following elements: 1) an expression cassette for a modified glucoamylase gene from *Saccharomycopsis fibuligera* containing an N-terminal secretion leader from alpha mating factor 1 (MFα1) corresponding to nucleotides 2769-4319, including an ADH1 promoter corresponding to nucleotides 2023-2768 and a CYC1 terminator corresponding to nucleotides 4320-4543, 2) a centromere to allow for stable replication (CEN6) corresponding to nucleotides 6801-7319, and 3) an expression cassette for an orotidine-5'-phosphate decarboxylase (URA3) corresponding to nucleotides 195-1292. SEQ ID NO 6 also includes an ampicillin resistance gene corresponding to nucleotides 5809-6669. Transformants are selected on ScD-Ura. Resulting transformants are streaked for single colony isolation on ScD-Ura. A single colony is selected. Presence of the plasmid is verified by PCR. The PCR verified isolate is designated Strain 1-5a, b, c.

Strain 1-6: *Saccharomyces cerevisiae* Expressing a Modified *Saccharomycopsis fibuligera* Glucoamylase Containing an N-Terminal Secretion Leader from Alpha Mating Factor 2(MFα2)

Strain 1-3 is transformed with SEQ ID NO 7. SEQ ID NO 7 contains the following elements: 1) an expression cassette for a modified glucoamylase gene from *Saccharomycopsis fibuligera* containing an N-terminal secretion leader from alpha mating factor 2 (MFα2) corresponding to nucleotides 2769-4319, including an ADH1 promoter corresponding to nucleotides 2022-2768 and a CYC1 terminator corresponding to nucleotides 4320-4543, 2) a centromere to allow for stable replication (CEN6) corresponding to nucleotides 6801-7319, and 3) an expression cassette for an orotidine-5'-phosphate decarboxylase (URA3) corresponding to nucleotides 195-1229 SEQ ID NO 7 also includes an ampicillin resistance gene corresponding to nucleotides 5809-6669. Transformants are selected on ScD-Ura. Resulting transformants are streaked for single colony isolation on ScD-Ura. A single colony is selected. Presence of the plasmid is verified by PCR. The PCR verified isolate is designated Strain 1-6 a, b, c.

Strain 1-7: *Saccharomyces cerevisiae* Expressing a Modified *Saccharomycopsis fibuligera* glucoamylase Containing an N-Terminal Secretion Leader from Acid Phosphatase (PHO5)

Strain 1-3 is transformed with SEQ ID NO 8. SEQ ID NO 8 contains the following elements: 1) an expression cassette for a modified glucoamylase gene from *Saccharomycopsis fibuligera* containing an N-terminal secretion leader from *Saccharomyces cerevisiae* acid phosphatase (PHO5) corresponding to nucleotides 2769-4313, including an ADH1 promoter corresponding to nucleotides 2023-2768 and a CYC1 terminator corresponding to nucleotides 4314-4537, 2) a centromere to allow for stable replication (CEN6) corresponding to nucleotides 6795-7313, and 3) an expression cassette for an orotidine-5'-phosphate decarboxylase (URA3) corresponding to nucleotides 195-1292. SEQ ID NO 8 also includes an ampicillin resistance gene corresponding to nucleotides 5803-6663. Transformants are selected on ScD-Ura. Resulting transformants are streaked for single colony isolation on ScD-Ura. A single colony is selected. Presence of the plasmid is verified by PCR. The PCR verified isolate is designated Strain 1-7 a, b, c.

Strain 1-8: *Saccharomyces cerevisiae* Plasmid Control

Strain 1-3 is transformed with SEQ ID NO 9. SEQ ID NO 9 contains the same elements as SEQ ID NO 5-8, with the exception that it lacks an expression cassette for a glucoamylase. Transformants are selected on ScD-Ura. Resulting transformants are streaked for single colony isolation on ScD-Ura. A single colony is selected. Presence of the plasmid is verified by PCR. The PCR verified isolate is designated Strain 1-8 a, b, c Strain 1-9: *Saccharomyces cerevisiae* Expressing a Modified *Saccharomycopsis fibuligera* Glucoamylase Containing an N-Terminal Secretion Leader from a Mating Factor 1 (MFa1)

Strain 1-3 is transformed with SEQ ID NO 15. SEQ ID NO 15 contains the following elements: 1) an expression cassette for a modified glucoamylase gene from *Saccharomycopsis fibuligera* containing an N-terminal secretion leader from a mating factor 1 (MFα1) corresponding to nucleotides 2769-4337, including an ADH1 promoter corresponding to nucleotides 2023-2768 and a CYC1 terminator corresponding to nucleotides 4338-4561, 2) a centromere to allow for stable replication (CEN6) corresponding to nucleotides 6819-7337, and 3) an expression cassette for an orotidine-5'-phosphate decarboxylase (URA3) corresponding to nucleotides 195-1292. SEQ ID NO 15 also includes an ampicillin resistance gene corresponding to nucleotides 5827-6687. Resulting transformants are streaked for single colony isolation on ScD-Ura. A single colony is selected. Presence of the plasmid is verified by PCR. The PCR verified isolate is designated Strain 1-9 a, b, c.

TABLE 3

Description of Engineered Yeast

| Strain | Description | Parent |
| --- | --- | --- |
| Strain 1 | *Saccharomyces cerevisiae* (Lasaffre, Ethanol Red) | N/A |
| Strain 1-1 | ura3Δ/URA3, ARO4-OFP+ | Strain 1 |
| Strain 1-2 | ura3Δ, ARO4-OFP+, amdS+ | Strain 1-1 |
| Strain 1-3 | ura3Δ | Strain 1-2 |
| Strain 1-4 a, b, c | *Saccharomycopsis fibuligera* GLA1+ | Strain 1-3 |
| Strain 1-5 a, b, c | *Saccharomycopsis fibuligera* GLA1+ (w/MFα1 leader) | Strain 1-3 |
| Strain 1-6 a, b, c | *Saccharomycopsis fibuligera* GLA1+ (w/ MFα2 leader) | Strain 1-3 |
| Strain 1-7 a, b, c | *Saccharomycopsis fibuligera* GLA1+ (w/PHO5 leader) | Strain 1-3 |
| Strain 1-8 a, b, c | Vector control | Strain 1-3 |
| Strain 1-9 a, b, c | *Saccharomycopsis fibuligera* GLA+ (w/MFa1 leader) | Strain 1-3 |

Example 2

Evaluation of Amylolytic *Saccharomyces cerevisaie* Strains in Simultaneous Saccharification and Fermentation Shake Flask Assays Shake Flask Evaluation Using Partially Hydrolyzed Corn Starch (AV_2014-08-20, Changing the Secretion Signal of the Sf GA)

A subset of strains listed in Table 3 are streaked out on a ScD-Ura plate and incubated at 30° C. until single colonies are visible (1-2 days). Cells from the ScD-Ura plate are scraped into sterile shake flask medium and the optical density ($OD_{600}$) is measured. Optical density is measured at wavelength of 600 nm with a 1 cm path length using a model Genesys20 spectrophotometer (Thermo Scientific).

A shake flask is inoculated with the cell slurry to reach an initial $OD_{600}$ of 0.1-0.3. Immediately prior to inoculating, 50 mL of shake flask medium is added to a 250 mL non-baffled shake flask (Corning 4995-250) fitted with a screw cap containing a gas-permeable seal (corning 1395-45LTMC) The shake flask medium consists of 850 g partially hydrolyzed corn starch (% DS 30-37, DE 5-15), 150 g filtered light steep water, 25 g glucose, and 1 g urea (Sigma U6504).

The inoculated flask is incubated at 30° C. with shaking in an orbital shake at 100 rpm for 72 hours. Samples are taken and analyzed for ethanol concentrations in the broth during fermentation by high performance liquid chromatography with refractive index detector.

The results of the shake flask, shown in Table 4, demonstrate an improvement in ethanol titer in strains expressing either the MFα2 or PHO5 leader sequence on the *Saccharomycopsis fibuligera* glucoamylase relative to strains expressing the native *Saccharomycopsis fibuligera* glucoamylase.

TABLE 4

Ethanol titers for strains expressing the *Saccharomycopsis fibuligera* glucoamylase with and without altered leader sequence.

| Strain | Description | Ethanol Titer at 72 Hours (g/L) |
|---|---|---|
| Strain 1-4a, b, c | *Saccharomycopsis fibuligera* GLA1+ | 83.6, 89.2, 81.6 |
| Strain 1-5a | *Saccharomycopsis fibuligera* GLA1+ (w/MFα1 leader) | 25.6, 25.5, 25.1 |
| Strain 1-6a, b, c | *Saccharomycopsis fibuligera* GLA1+ (w/ MFα2 leader) | 156.3, 158.7, 158.5 |
| Strain 1-7a, b, c | *Saccharomycopsis fibuligera* GLA1+ (w/PHO5 leader) | 156.7, 156.8, 157.1 |
| Strain 1-8a, b, c | Vector control | 25.6, 25.8, 25.6 |
| Strain 1-9a, b, c | *Saccharomycopsis fibuligera* GLA1+ (w/MFa1 leader) | 26.4, 26.5, 26.3 |

Example 3

Enzyme Production by Amylolytic *Saccharomyces cerevisaie* Strains

Shake Flask Evaluation Using Raffinose Grown Cells to Evaluate Enzyme Production A subset of strains listed in Table 3 are streaked out on a ScD-Ura plate and incubated at 30° C. until single colonies are visible (1-2 days). Cells from the ScD-Ura plate are scraped into sterile shake flask medium and the optical density ($OD_{600}$) is measured. Optical density is measured at wavelength of 600 nm with a 1 cm path length using a model Genesys20 spectrophotometer (Thermo Scientific).

A shake flask is inoculated with the cell slurry to reach an initial $OD_{600}$ of 0.1-0.3. Immediately prior to inoculating, 100 mL of shake flask medium is added to a 500 mL baffled shake flask. The shake flask medium consists of 5% Raffinose (Sigma R0250), 6.7 g Yeast Nitrogen Base (Difco 291940), and 1.9 g synthetic complete amino acid dropout mix (MP Biomedicals 4410-622).

The inoculated flask is incubated at 30° C. with shaking in an orbital shake at 250 rpm for 24 hours. Samples are taken and analyzed for $OD_{600}$ and cell dry weight. Cells were removed by centrifugation and 90 mls of broth was concentrated to 1.0 ml using a 10K MWCO column (Millipore UFC901024) and frozen prior to analysis.

Glucoamylase activity was measured in the concentrated broth by coupling starch hydrolysis to HXK/G6PDH reactions in a two-step end point assay (Sigma G3293). A unit (U) of GA activity can be defined as the amount of enzyme that catalyzes the release of 1 mg glucose/min from starch. Glucoamylase activity can be measured in concentrated broth by coupling starch hydrolysis to a HXK/G6PDH reaction mix (Sigma G3293) in a two-step end point assay. Broth can be concentrated from a predetermined amount of cells grown using a non-glucose carbon source (i.e. raffinose) to avoid interference with the assay.

The specific activity is equal to the activity in a given volume of broth divided by the wet weight of cells in the same volume of broth. Specific activity has the following units, U of GA activity per gram of biomass (U/g biomass). The amount of biomass used in the assay can be measured by determining the wet cell weight after removing the broth, either by filtration or centrifugation.

A starch solution is prepared by dissolving 1.1 g of corn starch (S4126, Sigma) in 50 mL of near boiling water, then adding 1 mL of 3M sodium acetate pH 5.2. A volume of concentrated broth ($V_b$), typically in the range of 1-20 ul (prepared by using a 10 Kb Kd cutoff column, Millipore # UFC901008) is added to the starch slurry ($V_s$), in a total volume of 200 ul, and allowed to incubate at 37° C. for a specific period of time (T), typically between 5-60 minutes. Parameters are selected such that the glucose formation is linear within a desired time. 20 μL of each sample is added to 2 μL 0.6N NaOH and mixed well. 200 μL of the HXK/G6PDH mix is then added and incubated at 30° C. for 30 minutes. The absorbance at 340 nm is measured using a spectrophotometer (SpectraMax™ M2). Regression analysis using known glucose standards is used to calculate the amount of glucose released in each sample. The specific enzyme activity per gram of biomass (U/g biomass) can be calculated by obtaining the weight in grams of the sample used prior to concentration. Unit of activity=(mg glucose/T)*(($V_b+V_s$)/($V_b$))*(222/20). Specific activity=Unit of activity/g biomass.

Protein concentrations were determined using Advanced Protein Assay Reagent (Cytoskeleton ADV01). A standard denaturing SDS-PAGE protein gel was run using 16 μl of concentrated broth combined with 4 μl of loading buffer from strains 1-4a 1-4b, 1-6a, 1-6b, 1-7a, 1-7b, 1-8a and 1-8b.

The results of the shake flask, shown in Table 5 and FIG. 1, demonstrate the beneficial effect of the MFα2 and the PHO5 leader sequence on *Saccharomycopsis fibuligera* glucoamylase secretion and activity.

TABLE 5

Enzyme production for strains expressing the *Saccharomycopsis fibuligera* glucoamylase with and without altered leader sequence.

| Strain | Description | Extracellular Enzyme activity (U/g biomass) | Extracellular protein (mg/mL) |
| --- | --- | --- | --- |
| Strain 1-4a, b | *Saccharomycopsis fibuligera* GLA1+ | 2.06, 1.91 | 0.06, 0.06 |
| Strain 1-5a, b | *Saccharomycopsis fibuligera* GLA1+ (w/MFα1 leader) | n.d. | n.d. |

TABLE 5-continued

Enzyme production for strains expressing the *Saccharomycopsis fibuligera* glucoamylase with and without altered leader sequence.

| Strain | Description | Extracellular Enzyme activity (U/g biomass) | Extracellular protein (mg/mL) |
| --- | --- | --- | --- |
| Strain 1-6a, b | *Saccharomycopsis fibuligera* GLA1+ (w/ MFα2 leader) | 7.33, 8.24 | 0.15, 0.21 |
| Strain 1-7a, b | *Saccharomycopsis fibuligera* GLA1+ (w/PHO5 leader) | 7.96, 10.5 | 0.21, 0.19 |
| Strain 1-8a, b | Vector control | −0.04, −0.01 | 0.02, 0.07 |

What is claimed is:

1. A host cell comprising a heterologous nucleic acid encoding for a polypeptide comprising (a) a secretion signal amino acid sequence having 90% or greater identity to SEQ ID NO:10 or SEQ ID NO:11 and (b) a glucoamylase amino acid sequence comprising amino acids 19-515 of SEQ ID NO:12, wherein the polypeptide has glucoamylase activity.

2. The host cell of claim 1, wherein the polypeptide is SEQ ID NO:13.

3. The host cell of claim 1, wherein the polypeptide is SEQ ID NO:14.

4. The host cell of claim 1, wherein the polypeptide encoded by the heterologous nucleic acid further comprises a third sequence that is different than SEQ ID NO:10, SEQ ID NO:11, or the glucoamylase amino acid sequence, wherein the third sequence is positioned between SEQ ID NO:10 and the glucoamylase amino acid sequence, or SEQ ID NO:11 and the glucoamylase amino acid sequence.

5. The host cell of claim 1, which is a species of *Saccharomyces*.

6. The host cell of claim 1, which is *Saccharomyces cerevisiae*.

7. The host cell of claim 1, which is tolerant to growth in a fermentation medium having a concentration of ethanol of greater than 90 g/L.

8. The host cell of claim 1, which is tolerant to growth at temperatures of greater than 33° C.

9. The host cell of claim 1, which is tolerant to growth at temperatures in the range of 34-40° C.

* * * * *